United States Patent [19]
Kim et al.

[11] Patent Number: 5,696,265
[45] Date of Patent: Dec. 9, 1997

[54] VINYL ETHERS OF NUCLEOSIDE ANALOGS

[75] Inventors: Choung Un Kim, Madison, Conn.; John C. Martin, San Carlos, Calif.; Bing Uh Luh, Killingworth; Peter F. Misco, Durham, both of Conn.

[73] Assignees: Institute of Organic Chemistry and Biochemistry of the Academy of Sciences of the Czech Republic, Czech Rep.; Rega Stichting v.z.w., Belgium

[21] Appl. No.: 488,340

[22] Filed: Jun. 7, 1995

Related U.S. Application Data

[62] Division of Ser. No. 391,312, Feb. 17, 1995, which is a continuation of Ser. No. 765,774, Sep. 26, 1991, abandoned, which is a continuation-in-part of Ser. No. 481,569, Feb. 22, 1990, abandoned, which is a continuation-in-part of Ser. No. 352,303, May 15, 1989, abandoned.

[51] Int. Cl.$^6$ .................. A61K 31/52; C07D 473/18; C07D 473/34; C07D 473/30
[52] U.S. Cl. .................. 544/264; 544/243; 544/244; 544/265; 544/267; 544/276; 544/277; 544/314; 544/318; 546/118
[58] Field of Search ............. 544/264, 265, 544/267, 276, 277, 314, 318; 546/118

[56] References Cited

U.S. PATENT DOCUMENTS

| | | | |
|---|---|---|---|
| 3,457,255 | 7/1969 | Jones et al. | 260/211.5 |
| 4,724,233 | 2/1988 | De Clercq et al. | 514/81 |
| 4,808,716 | 2/1989 | Holy et al. | 544/244 |
| 4,977,144 | 12/1990 | Fujimoto et al. | 514/46 |
| 5,066,654 | 11/1991 | Taylor, Jr. et al. | 514/256 |
| 5,142,051 | 8/1992 | Holy et al. | 544/243 |
| 5,223,499 | 6/1993 | Greenlee et al. | 514/234 |
| 5,470,857 | 11/1995 | Borcherding et al. | 514/258 |

FOREIGN PATENT DOCUMENTS

| | | |
|---|---|---|
| 0.044.527 A1 | 7/1981 | European Pat. Off. |
| 0 269 947 B1 | 6/1988 | European Pat. Off. |
| 0 398 231 A2 | 11/1990 | European Pat. Off. |
| 0.479.640 A2 | 9/1991 | European Pat. Off. |
| 2134907 | 8/1984 | United Kingdom |
| WO 84/04748 | 12/1984 | WIPO |
| WO 89/12061 | 12/1989 | WIPO |

OTHER PUBLICATIONS

Borthwick et al, Tet Lett, 31: 767 (1990).
Kowollik et al., "Ungesattigte Halogenzucker–Nucleoside Des Thymins (1)," Tet Lett 22:1737–1740 (structures only) (1971).
Spector et al., "Conversion of 2,6–Diamino–9–(2–Hydroxyethoxymethyl)Purine to Acyclovir as Catalyzed by Adenosine Deaminase", Biochem Pharm 32(17):2505–2509 (1983).
Townsend (Ed.), "Chemistry of Nucleosides & Nucleotides," 1:241, 242, 279 and 159 (1988).
Townsend (Ed.), "Chemistry of Nucleosides & Nucleotides," 3:318, 319, 416 (1994).

(List continued on next page.)

*Primary Examiner*—Mark L. Berch
*Attorney, Agent, or Firm*—Max D. Hensley

[57] ABSTRACT

Provided are compounds of the following formulae:

A phosphonomethoxymethyoxymethyl purine/pyrimidine derivative of the formula

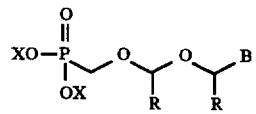

wherein X and X' are the same or different and are hydrogen or alkyl.

R and R' are the same or different and are hydrogen, alkyl, hydroxyalkyl or alkanoyl and B is a purine or pyrimidine base.

A 4'-phosphonomethoxytetrahydrofuranyl-1'-purine-pyrimidine of the formula

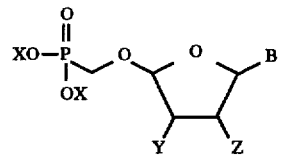

wherein X and X' are the same or different and are hydrogen or alkyl, Y and Z are the same or different and are hydrogen, hydroxyl or alkyl or Y+Z is an alkenyl, an epoxide or cyclopropyl, and B is a purine or pyrimidine base.

A compound of the formula (V)

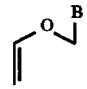

wherein B is cytosine, 5-ethylcytosine, 5-methylcytosine, thymine, uracil, 5-chlorouracil, 5-bromouracil, 5-ethyluracil, 5-iodouracil, 5-propyluracil, 5-vinyluracil, hypoxanthine, xanthine, guanine, 8-bromoguanine, 8-chloroguanine, 8-methylguanine, 8-thioguanine, 3-deazaguanine, purine, 2-aminopurine, 2,6-diaminopurine, adenine, 3-deazaadenine, 8-aminoguanine, 8-hydrazinoguanine, 8-hydroxyguanine, or 2-acetamido-6-diphenylcarbamoylpurine;

and the pharmaceutically acceptable salts thereof.

5 Claims, No Drawings

OTHER PUBLICATIONS

Bronson et al., "Synthesis and Antiviral Activity of Phosphonylmethoxyethyl Derivatives of Purine and Pyrimidine Bases," J 72–87 (1989) in Nucleoside Analogs.

Chow et al., "Stereospecific Vorbrüggen–like Reactions of 1,2–Anhydro Sugars—An Alternative Route to the Synthesis of Nucleosides," J Org Chem 55:4211–4214 (1990).

Chu et al, "Chemistry and Antiviral Activities of Acyclonucleosides," J Het Chem 23:289–319 (1986).

De Clercq et al, "A novel selective broad–spectrum anti–DNA virus agent," Nature 323:464–467 (1986).

Dvorakova, "Synthesis and Biological Effects of 9–(3–Hydroxy–2–Phosphonomethoxypropyl) Derivatives of Deazapurine Bases," Collect Czech Chem Commun 58:1403–1418 (1993).

Dvorakova et al, "Synthesis and Biological Effects of N–(2–Phosphonomethoxyethyl) Derivatives of Deazapurine Bases," Collect Czech Chem Commun 58:1419–1429 (1993).

Foguet et al., "Process for the Preparation of 9–(2–Hydroxyethoxymethyl) guanine, used as an Antiviral Agent," Chem Ab 107:236377g (1989).

Ho et al., "Cellular Metabolism and Enzymatic Phosphorylation of (2R,5R)–9–[2,5–Dihydro–5–(phosphonomethoxy)–2–furanyl]adenine (D4AMPI), An Anti–HIV Agent," Antiviral Res 17:66 (1992).

Holy et al., "3'–0–Phosphonylmethyl–9–(S)–(2,3–dihydroxypropyl)adenine novel type of biologically active nucleotide analogue," Nuc Acids Res 14:277–278 (1984).

Holy et al., "Phosphonylmethyl Ethers of Nucleosides and Their Acyclic Analogues," Am Chem Soc Symposium Series, 401 4:51–71.

Kaneko, Y., "Light Fading Inhibitor for Color Photographic Material," Chem Ab 111:205325s (1989).

Kim et al, "A new class of acyclic phosphonate nucleotide analogues: phosphonate isosteres of acyclovir and ganciclovir monophosphates as antiviral agents," J Med Chem 34(7):2286–2294 (1991).

Kim et al, "Regiospecific and Highly Stereoselective Electrophilic Addition to Furanoid Glycals: Synthesis of Phosphonate Nucleotide Analogues with Potent Activity against HIV," J Org Chem 56:2642–2647 (1991).

Kim et al, "Synthesis of a phosphonate isostere of acyclovir monophosphate: a herepesvirus active phosphonate nucleotide analogue," Heterocycles 31(9):1571–1574 (1990).

Kim et al, "Synthesis of a phosphonate isostere of ganciclovir monophosphate: a highly cytomegalovirus active phosphonate nucleotide analogue," Tet Lett 31:3257 (1990).

Kim et al., "Synthesis and anti–HIV Activity of 9[(2R, 5R)–2,5–Dihydro–5–(Phosphonomethoxy)–2–Furanyl]2, 6–Diaminopurine," Bioorg Med Chem Lett 2:307–310 (1992).

Kim et al., "Synthesis and HIV Activity of Phosphonate Isosteres of D4T Monophosphate," Bioorg Med Chem Lett 2:367–370 (1992).

Prisbe et al., "Synthesis and Antiherpes Virus Activity of Phosphate and Phosphonate Derivatives of 9–[1,3–Dihydroxy–2–propoxy)methyl]guanine," J Med Chem 29:671–675 (1986).

Robins et al., "Synthesis, Transformation Chemistry, and Biological Activity of Guanine Nucleosides and Analogues," Nucls & Nuclt 8:725–741 (1989).

Rosenberg et al, "Phosphonylmethoxyalkyl and Phosphonylalkyl Derivatives of Adenine," Collect Czech Chem Commun 53:2753–2777 (1988).

Sergheraert et al., "Synthesis and Anti–HIV Evaluation of D4T and D4T 5'–Monophosphate Prodrugs," J Med Chem 36:826–830 (1993).

Yokota et al, "Inhibitory effects of acyclic nucleoside phosphonate analogues on hepatitis B virus DNA synthesis in HB611 cells," Antiviral Chem & Chemo 5(2):57–63 (1994).

Zemlicka et al., "Nucleosides. XV. Decarboxylative Elimination of 2'–Deoxynucleoside Uronic Acids," J Am Chem Soc 94:3213–3218 (1972).

VINYL ETHERS OF NUCLEOSIDE ANALOGS

This is a divisional of application(s) Ser. No. 08/391,312 filed on Feb. 17, 1995 which is a continuation of U.S. Ser. No. 07/765,774, filed Sep. 26, 1991, now abandoned, which is a continuation-in-part of U.S. Ser. No. 07/481,569, filed Feb. 22, 1990; now abandoned, which is a continuation-in-part of U.S. Ser. No. 07/352,303, filed May 15, 1989, now abandoned.

BACKGROUND OF THE INVENTION

1. Field of the Invention

The present invention concerns nucleotide analogs and their compositions and use. In particular, the invention concerns antiviral (including antiretroviral) and antitumor phosphonomethoxy-methyloxymethyl purine/pyrimidine derivatives and 4'-phosphonomethyl-oxymethoxytetrahydrofuranyl-1'-purine/pyrimidine derivatives.

2. Background Information

Infectious viral diseases are recognized as an important medical problem. Progress against infectious viral disease requires the development of drugs with selective antiviral activity while remaining benign to normal cell lines. A number of antiviral agents currently under study which seem to possess some selectivity are nucleoside analogs. In general, these compounds are structural analogs of the naturally occurring nucleosides. Structural modification in either the purine or pyrimidine base nucleus and/or the saccharide component results in a synthetically modified nucleoside derivative which, when incorporated into a viral nucleic acid forming process, acts to disrupt further synthesis of viral nucleic acid. Effectiveness of these antiviral agents depends on selective conversion by viral enzymes, but not by host enzymes, to the corresponding nucleotide analog which is then converted to the triphosphate and incorporation into viral nucleic acid occurs. A problem with this antiviral strategy has been the emergence of certain viral strains whose enzymes poorly promote phosphorylation of the nucleoside analogs. To circumvent this problem, intact nucleotide analogs appear to be potentially quite useful as antivirals for incorporation into viral nucleic acid.

Reist and Strum in PCT/US 84/00737, published Dec. 6, 1984, disclosed new phosphonic acid analogs of nucleoside phosphates which are useful as antivirals for incorporation into viral DNA. The structural formula for these compounds is shown below as 1':

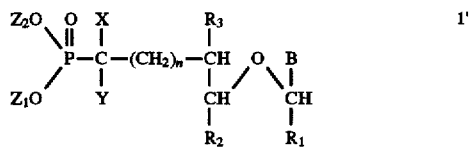

In the Reist and Sturm compounds, B is a purine or pyrimidine base: $R_1$ and $R_2$ together complete a β-pentofuranose sugar or $R_1$ is H and $R_2$ is H or hydroxmethyl; $R_3$ is H or OH: X is H, OH or together with Y is carbonyl oxygen and Y can also be H; $Z_1$ and $Z_2$ are H or alkyl.

Similarly, the synthesis and anti-Herpes-Virus activity of phosphate and phosphonate derivatives of 9-[(1,3-dihydroxy-2-propoxy)methyl]guanine (Formula 2' were disclosed by Prisbe, et al., in *J. Med. Chem.*, 1986, 29, 671.

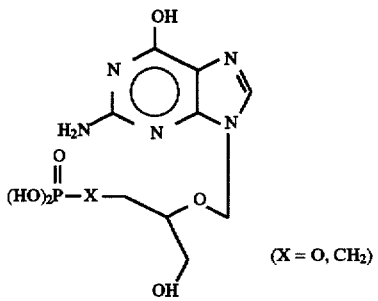

Other phosphonate nucleotide analogs of the Formula 2' type wherein $X=CH_2$ have been described by R. M. Riggs et al., Nucleosides and Nucleotides, 8(5&6), 1119–1120 (1989); D. H. R. Bouton, et al., Tetrahedron Letters, 30, No. 37, 4969–4972 (1972); and H. Tanaka, et al., Tetrahedron Letters, 30, 2567–2570 (1989).

Adenine phosphonic analogs (Formula 3') and their syntheses are disclosed in the UK Patent Application of Holy, et al., GB 2,134,907A published Aug. 22, 1984.

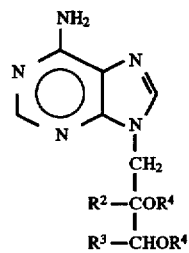

In formula 3', $R_2$ and $R_3$ are H or together complete a ribonucleoside ring; and both $R_4$ are alternately a hydrogen and $-CH_2P(O)(OH)_2$ group.

A preferred example of one of these compounds, known as (S)—HPMPA (Formula 4') was disclosed by DeClercq, et al., in *Nature*, 1986, 323, pp. 464–467 and earlier by Holy, et al., *Nucleic Acids Research*, Symposium Series No. 14, 1984, pp. 277–278. Phosphonate compounds which are HPMPA analogs are described in South African Patent 1987/8607. In applicant's hands, (S)—HPMPA is only slightly active in mice inoculated with *Herpes simplex* virus-2. In a 21 day protocol 30% of a group of animals treated i.p. with 50 mg/kg/day of (S)—HPMPA survived.

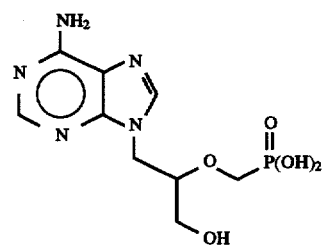

There is no teaching contained in these references, or a combination thereof, which would make obvious the compounds, compositions, and uses involved in the present invention.

SUMMARY OF THE INVENTION

Phosphonomethoxymethoxymethyl purine and pyrimidine derivatives, 4'-phosphonomethoxytetrahydro-2-furyl-9-purine and 1-pyrimidine derivatives, phosphonomethoxymethoxymethyl-9-purine and 1-pyrimidine derivatives having a cyclic phosphonate group and 4'-phosphonomethoxytetrahydro-2-furyl-9-purine and 1-pyrimidine derivatives having a cyclic phosphonate group have been synthesized and found to possess useful antiviral and antitumor activity.

The present invention concerns a phosphonomethoxymethoxymethyl purine/pyrimidine derivative of the formula:

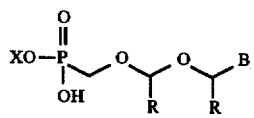   (I)

wherein X and X' are the same or different and are hydrogen or alkyl having 1 to 6 carbon atoms, R and R' are the same or different and are hydrogen, alkyl having 1 to 6 carbon atoms, hydroxyalkyl with 1 to 6 carbon atoms, alkanoyl having 2 to 7 carbon atoms, and B is a 9-substituted purine or 1-substituted pyrimidine base selected from the group consisting of xanthine, substituted xanthine, for example, hypoxanthine, guanine, substituted guanine, for example, 8-bromoguanine, 8-chloroguanine, 8-aminoguanine, 8-hydrazinoguanine, 8-hydroxyguanine, 8-methylguanine, 8-thioguanine and 3-deazaguanine, purine, substituted purine, for example, 2-aminopurine, 2,6-diaminopurine, cytosine, substituted cytosine, for example, 5-ethylcytosine and 5-methylcytosine, thymine, uracil, 5-substituted uracil, for example, 5-chlorouracil, 5-bromouracil, 5-ethyluracil, 5-iodouracil, 5-propyluracil and 5-vinyluracil, adenine and substituted adenine, for example, 3-deazaadenine, and pharmaceutically acceptable salts thereof.

The present invention also concerns a 4'-phosphonomethoxytetrahydro (or -dihydro-)-fur-2-yl-purine or pyrimidine derivative of the formula:

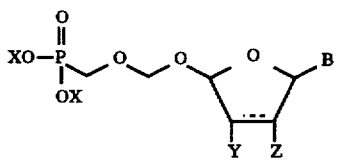   (II)

wherein X and X' are the same or different and are hydrogen or alkyl having 1 to 6 carbon atoms, the broken line represents an optional bond,

- Y and Z are the same or different and are unsubstituted or halogen-, hydroxy-, amino- or azido substituted alkyl with 1 to 6 carbon atoms or together they constitute an oxygen atom or methylene group in which event the broken line is absent, and
- B is a 9-substituted purine or a 1-substituted pyrimidine base selected from the group consisting of xanthine, substituted xanthine, for example, hypoxanthanine, guanine, substituted guanine, for example, 8-bromoguanine, 8-chloroguanine, 8-methylguanine and 8-thioguanine and 3-deazaguanine, purine, substituted purine, for example, 2-aminopurine, 2,6-diaminopurine, cytosine, substituted cytosine, for example, 5-ethylcytosine and 5-methylcytosine, thymine, uracil, 5-substituted uracil, for example, 5-chlorouracil, 5-bromouracil, 5-ethyluracil, 5-iodouracil, 5-propyluracil and 5-vinyluracil, adenine and substituted adenine, for example, 3-deazaadenine, and pharmaceutically acceptable salts thereof.

The invention also concerns a 4'-phosphonomethoxytetrahydrofur-2-yl-purine or pyrimidine derivative having a cyclic phosphonate group of the formula:

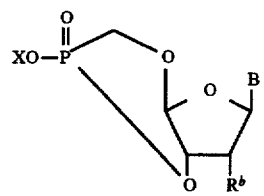   (III)

wherein X is hydrogen or alkyl with 1 to 6 carbon atoms, $B^6$ is H or OH and B is a 9-substituted purine or a 1-substituted pyrimidine base selected from the group consisting of xanthine, substituted xanthine, for example, hypoxanthine, guanine, substituted guanine, for example, 8-bromoguanine, 8-chloroguanine, 8-aminoguanine, 8-hydrazinoguanine, 8-hydroxyguanine, 8-methylguanine, 8-thioguanine and 3-deazaguanine, purine, substituted purine, for example, 2-aminopurine, 2,6-diaminopurine, cytosine, substituted cytosine, for example, 5-ethylcytosine and 5-methylcytosine, thymine, uracil, 5-substituted uracil, for example, 5-chlorouracil, 5-bromouracil, 5-ethyluracil, 5-iodouracil, 5-propyluracil and 5-vinyluracil, adenine and substituted adenine, for example, 3-deazaadenine, and pharmaceutically acceptable salts thereof.

The invention is further directed to a phosphonomethoxymethoxymethyl-9-substituted purine or 1-substituted pyrimidine derivatives having a cyclic phosphonate group of the formula:

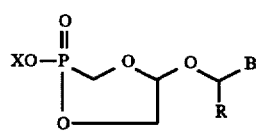   (IV)

wherein X is hydrogen, alkyl with 1 to 6 carbon atoms,

R is hydrogen, alkyl with 1 to 6 carbon atoms or alkanoyl having 2 to 7 carbon atoms, and B is a purine or pyrimidine base selected from the group consisting of xanthine, substituted xanthine, for example, hypoxanthine, guanine, substituted guanine, for example, 8-bromoguanine, 8-chloroguanine, 8-aminoguanine, 8-hydrazinoguanine, 8-hydroxyguanine, 8-methylguanine, 8-thioguanine and 3-deazaguanine, purine, substituted purine, for example, 2-aminopurine, 2,6-diaminopurine, cytosine, substituted cytosine, for example, 5-ethylcytosine and 5-methylcytosine, thymine, uracil, 5-substituted uracil, for example, 5-chlorouracil, 5-bromouracil, 5-ethyluracil, 5-iodouracil, 5-propyluracil and 5-vinyluracil, adenine and substituted adenine, for example, 3-deazaadenine, and pharmaceutically acceptable salts thereof.

The present invention also concerns the following intermediates:

   (V)

wherein B is a 9-substituted purine or a 1-substituted pyrimidine base selected from the group consisting of xanthine, substituted xanthine, for example, hypoxanthine, guanine, substituted guanine, for example, 8-bromoguanine, 8-chloroguanine, 8-aminoguanine, 8-hydrazinoguanine, 8-hydroxyguanine, 8-methylguanine, 8-thioguanine and 3-deazaguanine, purine, substituted purine, for example, 2-aminopurine, 2,6-diaminopurine, cytosine, substituted cytosine, for example, 5-ethylcytosine and 5-methylcytosine, thymine, uracil, 5-substituted uracil, for example, 5-chlorouracil, 5-bromouracil, 5-ethyluracil, 5-iodouracil, 5-propyluracil and 5-vinyluracil, adenine and substituted adenine, for example, 3-deazaadenine;

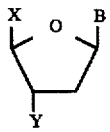 (VI)

wherein X is a halogen, for example, chlorine, bromine, iodine or fluorine,

Y is phenylthio, phenylseleno or a halogen atom, for example, chlorine, bromine, iodine or fluorine, and B is a 9-substituted purine or 1-substituted pyrimidine base selected from the group consisting of xanthine, substituted xanthine, for example, hypoxanthine, guanine, substituted guanine, for example, 8-bromoguanine, 8-chloroguanine, 8-aminoguanine, 8-hydrazinoguanine, 8-hydroxyguanine, 8-methylguanine, 8-thioguanine and 3-deazaguanine, purine, substituted purine, for example, 3-aminopurine, 2,6-diaminopurine, cytosine, substituted cytosine, for example, 5-ethylcytosine and 5-methylcytosine, thymine, uracil, 5-substituted uracil, for example, 5-chlorouracil, 5-bromouracil, 5-ethyluracil, 5-iodouracil, 5-propyluracil and 5-vinyluracil, adenine and substituted adenine, for example, 3-deazaadenine;

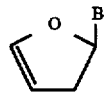 (VII)

wherein B is guanine, substituted guanine, for example, 8-bromoguanine, 8-chloroguanine, 8-aminoguanine, 8-hydrazinoguanine, 8-hydroxyguanine, 8-methylguanine, 8-thioguanine and 3-deazaguanine, cystosine or substituted cytosine, for example, 5-ethylcytosine and 5-methylcytosine; adenine and substituted adenine and,

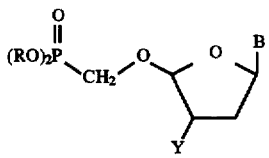 (VIII)

wherein Y is a halogen, for example chlorine, fluorine, bromine or iodine, phenylthio, or phenylseleno, R is hydrogen or alkyl with 1 to 6 carbon atoms and B is a purine or pyrimidine base selected from the group consisting of xanthine, substituted xanthine, for example, hypoxanthine, guanine, substituted guanine, for example, 8-bromoguanine, 8-chloroguanine, 8-aminoguanine, 8-hydrazinoguanine, 8-hydroxyguanine, 8-methylguanine, 8-thioguanine and 3-deazaguanine, purine, substituted purine, for example, 2-aminopurine, 2,6-diaminopurine, cytosine, substituted cytosine, for example, 5-ethylcytosine and 5-methylcytosine, thymine, uracil, 5-substituted uracil, for example, 5-chlorouracil, 5-bromouracil, 5-ethyluracil, 5-iodouracil, 5-propyluracil and 5-vinyluracil, adenine and substituted adenine, for example, 3-deazaadenine.

The present invention further relates to the following processes:

(R1)

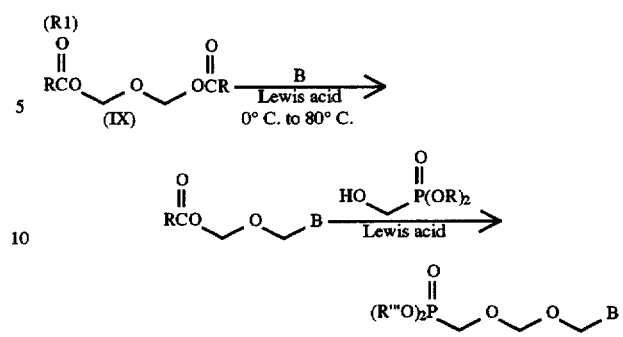

wherein R'' is an alkyl having 1 to 6 carbon atoms or an unsubstituted aryl or an aryl substituted by a substituent such as a halogen, e.g., bromine or chlorine, nitro, alkyl having 1 to 6 carbon atoms or an alkoxy having 1 to 6 carbon atoms, B is a silylated purine or pyrimidine base, and R is hydrogen or alkyl with 1 to 6 carbon atoms; preferably the molar ratio of compound (IX) to B is 1:1;

(R2)

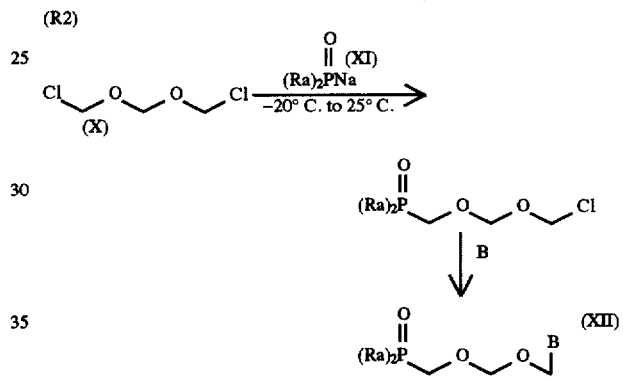

wherein R is an alkyl having 1 to 6 carbon atoms and B is a purine or pyrimidine base; preferably compound (X) is 5 to 10 times in excess of compounds (XI) and the preferred molar ratio of compound (XII) to B is 1:1;

(R3)

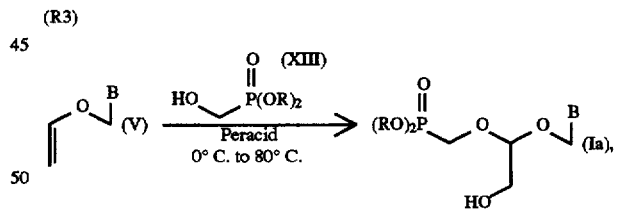

wherein compound (XIII) is preferably in a 5 to 10 times excess of compound (V);

(R4)

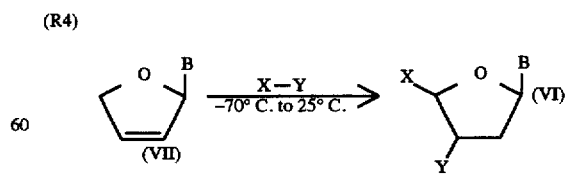

wherein X—Y is a halogen, e.g., $Br_2$, $Cl_2$, phenyl-Se—Z, phenyl-S—Z (wherein Z=halogen) and B is a purine or pyrimidine base; preferably the molar ratio of compound (VII) to X—Y is 1:1;

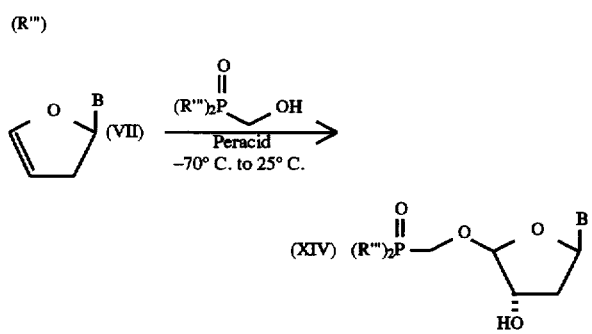

wherein R is hydrogen or alkyl with 1 to 6 carbon atoms; preferably compound (XIV) is 5 to 10 times in excess of compound (VII).

DETAILED DESCRIPTION OF THE INVENTION

The compounds of the present invention can exist as optical isomers. Both the racemic and diasteromeric mixtures of these isomers which may exist for certain compounds, as well as the individual optical isomers, are all within the scope of the present invention. While the racemic mixtures can be separated into their individual isomers through well-known techniques such as, for example, the separation of diastereomeric salts formed with optically active adjuncts, e.g., acids or bases followed by conversion back to the optically active substrates, in most instances, for the compounds of the present invention, the preferred optical isomer can be synthesized by means of stereospecific reactions, beginning with the appropriate stereoisomer of the desired starting material.

As indicated above, the present invention also pertains to pharmaceutically acceptable non-toxic salts of these compounds, containing, for example, $Na^+$, $Li^+$, $K^+$, $Ca^{++}$ and $Mg^{++}$. Such salts may include those derived by combination of appropriate cations such as alkali and alkaline earth metal ions or ammonium and quaternary amino ions with the acid anion moiety of the phosphonic acid group. Metal salts can be prepared by reacting the metal hydroxide with a compound of this invention. Examples of metal salts which can be prepared in this way are salts containing $Li^+$, $Na^+$, and $K^+$. A less soluble metal salt can be precipitated from the solution of a more soluble salt by addition of the suitable metal compound. In addition, salts may be formed from acid addition of certain organic and inorganic acids, e.g., HCl, HBr, $H_2SO_4$ or organic sulfonic acids, with basic centers of the purine, specifically guanine, or pyrimidine base. Finally, it is to be understood that compounds of the present invention in their unionized, as well as zwitterionic form, and/or in the form, of solvates are also considered part of the present invention.

Compounds of the present invention also exist in subclasses, with two broad subclasses being those wherein B is either a purine or a pyrimidine base. Of these broad subclasses there are preferred classes wherein the purine base is a guanine or a substituted guanine moiety and where the pyrimidine bases are either thymine or cytosine. The most preferred class of compounds are those wherein B is guanine or substituted guanine.

Compounds of the present invention may also be subclassed according to the structure of the phosphonate moiety. These classes are comprised of the diester, the monoester, and the diacid. Preferred subclasses of the phosphonate moiety are the monoester and the diacid.

The compounds of this invention, including the physiologically acceptable salts thereof, have desirable antiviral and antitumor activity. They exhibit activity against viruses, for example, Herpes Simplex virus I ("HSV-1"), Herpes Simplex virus II ("HSV-2"), cytomegalo-virus ("CMV"), Varicella Zoster virus ("VZV"), influenza virus, vaccinia, polio, rubella, small pox, cowpox, Epstein-Barr virus ("EBV"), measles virus, human respiratory virus, hepatitis virus e.g., Hepatitis B, papillomavirus and sinbis virus, just to mention a few. The compounds also are active against retroviruses, for example, human immunodeficiency virus ("HIV"). The inventive compounds also have an antitumor effect. They are active against murine leukemia P388 and other experimental tumors.

As mentioned above, the compounds of the present invention are useful active ingredients in human and veterinary medicine for the treatment and prophylaxis of diseases caused by retroviruses. Examples of fields of indication in human medicine regarding retroviruses are as follows:

(1) the treatment or prophylaxis of human retrovirus infections;

(2) the treatment or prophylaxis of diseases caused by HIV (virus of human immune deficiency; previously called HTLV III/LAV or AIDS) and the stages associated therewith such as "ARC" (AIDS related complex) and "LAS" (lymph adenopathy syndrome) and the immune weakness and encephalopathy caused by this retrovirus;

(3) the treatment or prophylaxis of HTLV I infection or HTLV II infection;

(4) the treatment or prophylaxis of the AIDS carrier state (AIDS transmitter state); and (5) the treatment or prophylaxis of diseases caused by hepatitis B virus.

Examples of indications in veterinary medicine are as follows:

(1) Maedivisna (in sheep and goats),
(2) progressive pneumonia virus (PPV) (in sheep and goats),
(3) caprine arthritis encephalitis virus (in sheep and goats),
(4) Zwoegerziekte virus (in sheep),
(5) infectious virus of anemia (of the horse), and
(6) infections caused by cat leukemia virus.

For use against viral infections and against tumors, the compounds of this invention can be formulated into pharmaceutical preparations. Such preparations are composed of one or more of the inventive compounds in association with a pharmaceutically acceptable carrier. The reference *Remington's Pharmaceutical Sciences*, 17th Edition by A. R. Gennaro (Mack Publishing Company, 1985) discloses typical carriers and methods of preparation. For antiviral purposes, the compounds may be administered topically or systemically to warm blooded animals, e.g., humans. For antitumor use, systemic, and preferably, parenteral administration is employed. By systemic administration is intended, oral, rectal, and parenteral (i.e., intramuscular, intravenous, subcutaneous and nasal) routes. Generally, it will be found that when a compound of the present invention is administered orally, a larger quantity of the reactive agent is required to produce the same effect as the smaller quantity given parenterally. In accordance with good clinical practice, it is preferred to administer the instant compounds at a concentration level that will produce effective antiviral or antitumor effect without causing any harmful or untoward side effects.

Therapeutically and prophylactically the instant compounds are given as pharmaceutical compositions comprised of an effective antiviral or antitumor amount of a compound according to the invention or a pharmaceutically acceptable salt thereof and a pharmaceutically acceptable carrier, as stated hereinabove. Pharmaceutical compositions for effecting such treatment will contain a major or minor amount, e.g., from 95 to 0.5% of at least one compound of the present invention in combination with a pharmaceutical carrier, the carrier comprising one or more solid, semi-solid, or liquid diluents, fillers and formulation adjuvants which are non-toxic, inert and pharmaceutically acceptable. Such pharmaceutical compositions are preferably in dosage unit form; i.e., physically discrete units containing a predetermined amount of the drug corresponding to a fraction or multiple of the dose which is calculated to produce the desired therapeutic response. Other therapeutic agents can also be present. Pharmaceutical compositions providing from about 1 to 50 mg of the active ingredient per unit dose are preferred and are conventionally prepared as tablets, lozenges, capsules, powders, aqueous or oily suspensions, syrups, elixirs, and aqueous solutions. Preferred oral compositions are in the form of tablets or capsules and may contain conventional excipients such as binding agents, (e.g., syrup, acacia, gelatin, sorbitol, tragacanth or polyvinylpyrrolidone), fillers (e.g., lactose, sugar, corn starch, calcium phosphate, sorbitol, or glycine), lubricants (e.g., magnesium stearate, talc, polyethylene glycol or silica), disintegrants (e.g., starch) and wetting agents (e.g., sodium lauryl sulfate). Solutions or suspensions of an inventive compound with conventional pharmaceutical vehicles are employed for parenteral compositions, such as an aqueous solution for intravenous injection or an oily suspension for intramuscular injection. Such compositions having the desired clarity, stability and adaptability for parenteral use are obtained by dissolving from 0.1% to 10% by weight of an active inventive compound in water or a vehicle comprising a polyhydric aliphatic alcohol such as glycerine, propylene glycol, and polyethylene glycol or mixtures thereof. The polyethylene glycols comprise a mixture of non-volatile, usually liquid, polyethylene glycols which are soluble in both water and organic liquids and have molecular weights from about 200 to 1500.

Considering the biological activities possessed by the compounds of the instant invention, it can be seen that these compounds have antitumor and antiviral properties, particularly suited to their use in combating viral infections or tumors. Thus, another aspect of the instant invention concerns a process for treating viral (including retroviral) infections or tumors in a mammal in need of such treatment which comprises systemic or topical administration to such mammal of an effective dose of an inventive compound or a pharmaceutically acceptable salt thereof. On the basis of testing, an effective dose could be expected to be from about 0.01 to about 30 mg/kg body weight with about 1 to about 20 mg/kg body weight a preferred dosage range. It is envisioned that for clinical antiviral application compounds of the instant invention will be administered in the same manner as for the reference drug acyclovir. For clinical applications, however, the dosage and dosage regimen, in each case, must be carefully adjusted, utilizing sound professional judgment and consideration of the age, weight and condition of the recipient, the route of administration and the nature and gravity of the illness. Generally a daily oral dose will comprise from about 150 to about 750 mg, preferably 250–500 mg of an inventive compound administered from one to three times a day. In some instances, a sufficient therapeutic effect can be obtained at lower doses, while in others, larger doses will be required.

In the reaction (process) (R1) described above, non-limiting examples of Lewis acids include BF$_3$.etherate, TiCl$_4$ and BCl$_3$.

In the reactions (processes) (R3) and (R5) described above, non-limiting examples of peracids include the following: m-chloroperbenzoic acid, trifluoroperacetic acid and perbenzoic acid.

The reactions (processes) (R1) to (R5) described above are preferably conducted at atmospheric pressure and preferably conducted in the presence of a solvent, e.g., CH$_3$CN, CH$_2$Cl$_2$, ClCH$_2$CH$_2$Cl, CHCl$_3$, THF, dioxane, diethylether, benzene or toluene.

DESCRIPTION OF THE SPECIFIC EMBODIMENTS

The compounds which constitute this invention and their methods of preparation will appear more fully from a consideration of the following examples which are given for the purpose of illustration only and are not to be construed as limiting the invention in sphere or scope. In addition to the compounds described in the following examples, further compounds encompassed by the present invention are as follows:

9-[(2-Hydroxy-1-phosphonomethoxyethoxy)methyl] adenine disodium salt:

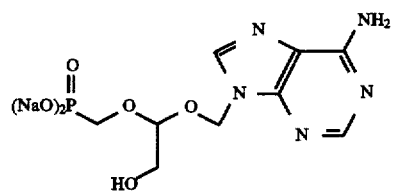

9-[(2-Hydroxy-1-phosphonomethoxyethoxy)methyl] cytosine disodium salt:

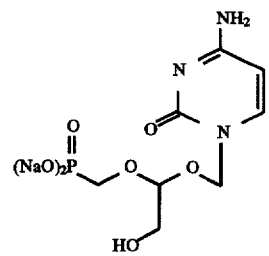

9-[(2-Hydroxy-1-phosphonomethoxyethoxymethyl] thymine disodium salt:

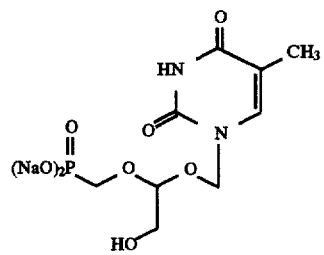

In the following examples, all temperatures are understood to be in degrees C when not specified. The nuclear magnetic resonance (NMR) spectral characteristics refer to chemical shifts (δ) expressed in parts per million (ppm) versus tetramethylsilane (TMS) as a reference standard, unless stated otherwise. The relative area reported for the various shifts in the proton NMR spectral data corresponds to the number of hydrogen atoms of a particular functional type in the molecule. The nature of the shifts as to multiplicity is reported as broad singlet (bs), singlet (s), multiplet (m), doublet (d), doublet of doublets (dd), triplet (t) or quartet (q).

Abbreviations employed are:

ACV (acyclovir)
BID (twice a day)
$CDCl_3$ (deuterochloroform)
DMF (dimethylformamide)
DMSO-$d_6$ (perdeuterodimethylsulfoxide)
EMEM (Earle's Minimum Essential medium)
Et (ethyl)
HIV (human immune deficiency)
HSV (Herpes simplex virus)
MuLV (murine leukemia virus)
NOE (Nuclear Overhauser Effect)
PFU (plaque forming units)
φ (phenyl)
TMS (trimethylsilyl)
Me (methyl)
Ac (acetyl)
Pv (pivaloyl)
Ph (phenyl)

All compounds gave satisfactory elemental analyses.

The invention will now be described with reference to the following non-limiting examples.

EXAMPLES

Example 1

Bisbenzoyloxymethyl ether (1)

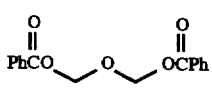

To a suspension of sodium benzoate (5.0 g, 34.7 mmol) in DMF (70 mL) was added bischloromethyl ether (20 g, 17.3 mmol) and the mixture was heated at 70° C. for 16 hr. The insoluble material was removed by filtration. The filtrate was concentrated in vacuo to give a white crystal which was recrystallized from ether-pentane: yield 4.5 g (91%); m.p. 39° C.

Analysis: Calcd. for $C_{16}H_{14}O_5$: C, 67.12; H, 4.92. Found: C, 66.87; H, 4.94.

$^1$H-NMR (200 MHz, $CDCl_3$): δ5.66 (s, 4H), 7.75–8.05 (m, 10H).

Example 2

1-[(Benzoyloxymethoxy)methyl]thymine (2)

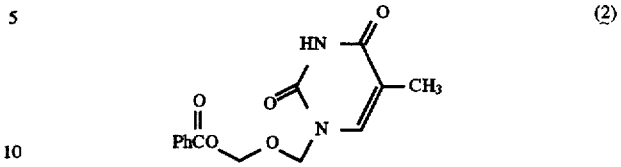

A. A suspension of thymine (12.6 g, 0.1 mole), ammonium sulfate (300 mg) and trimethylsilyl chloride (2.5 mL) in hexamethyldisilazane (150 mL) was heated at 140° C. for 16 hr under nitrogen. The volatiles were removed in vacuo at 50° C. and the residual oil was dissolved in xylene (30 mL) and concentrated to dryness.

B. To a solution of the silylated thymine in $CH_2Cl_2$ (200 mL) was added bisbenzoyloxymethyl ether (30 g, 0.1 mol) and trimethylsilyl trifluoromethanesulfonate (50 mL). The solution was stirred for 8 hr at 25° C. under nitrogen. The reaction was diluted with ethyl acetate (400 mL) and washed with aqueous sodium carbonate, brine, dried ($MgSO_4$), filtered and concentrated in vacuo. The crude oily material was purified by silica gel column chromatography using $CH_2Cl_2$/5% MeOH as eluent to give the title compound as white crystals: yield 14.5 g (50%); m.p. 141°–143° C.

Analysis: Calcd. for $C_{14}H_{14}N_2O_5$: C, 57.93; H, 4.82; N, 9.65. Found: C, 57.59; H, 4.90; N, 9.52.

$^{13}$C-NMR (50.3 MHz, DMSO-$d_6$): δ70.779, 72.477, 72.915, 73.349, 82.985, 105.563, 123.376, 124.076, 124.368, 128.383, 134.397, 146.260, 159.451, 160.211.

$^1$H-NMR ($CDCl_3$): δ1.82 (s, 3H), 5.38 (s, 2H), 5.62 (s, 2H), 7.10 (s, 1H), 7.4–8.0 (m, 5H).

Example 3

1-[(Diethylphosphonomethoxy)methoxymethyl]thymine (3)

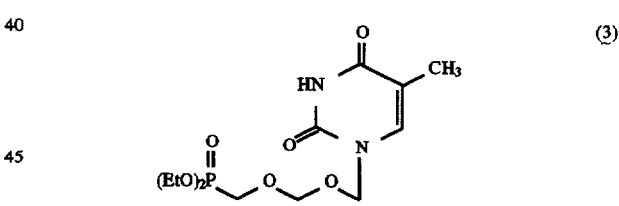

To a solution of 1-[(benzoyloxy)methoxymethyl]thymine (2.9 g, 10 mmol) and diethyl phosphonomethanol (1.85 g, 11 mmol) in benzene (180 mL) was added trimethylsilyl trifluoromethanesulfonate (0.05 mL) via a syringe under nitrogen. The solution was heated at 85° C. for 20 min. After cooling to room temperature, ethyl acetate (50 mL) was added and washed with aqueous bicarbonate, brine dried ($MgSO_4$), filtered and concentrated in vacuo. The resultant yellow oil was purified by silica gel column chromatography using $CH_2Cl_2$/5% MeOH as an eluent to give the title compound as a white oil: yield 980 mg (30%).

$^1$H-NMR (200 MHz, $CDCl_3$): δ1.39 (t, J=6.6 Hz, 6H), 1.98 (s, 3H), 3.85 (d, J=9.9 Hz, 2H), 4.1–4.3 (m, 4H), 4.82 (s, 2H), 5.20 (s, 2H), 7.20 (s, 1H), 9.0 (bs, 1H).

Example 4

1-[3-(Ethylphosphonomethoxy)methyloxymethyl)]thymine sodium salt (4)

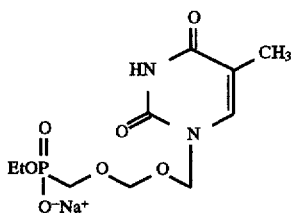

(4)

A solution of 1-[(diethylphosphonomethoxy) methoxymethyl]thymine (400 mg, 1.2 mmol) in 1N NaOH (8 mL) was stirred for 3 hr at 25° C. The solution was concentrated in vacuo and the resultant solid was purified by $C_{18}$ reverse phase column chromatography using water as an eluent under 8 psi pressure. The fractions having ultraviolet absorption were checked with HPLC, combined and lyophilized to give the title compound as a white amorphous powder: yield 220 mg (55%).

Analysis: Calcd. for $C_{10}H_{16}N_2O_7PNa \cdot H_2O$: C, 34.48; H, 5.17; N, 8.05. Found: C, 34.92; H, 5.37; N, 8.35.

$UV_{max\ (H_2O)}$: 226 nm ($\epsilon$=6966).

$^{13}$C-NMR (50.3 MHz, $D_2O$): δ11.451, 15.843, 61.067, 61.826, 63.585, 75.247, 94.631, 111.049, 141.277, 155.20, 170.907.

$^1$H-NMR (200 MHz, $D_2O$): δ1.19 (t, J=6.8 Hz, 3H), 1.81 (s, 3H), 3.62 (d, J=8.9 Hz, 2H), 3.8–4.1 (m, 2H), 3.62 (s, 2H), 4.78 (s, 2H), 5.20 (s, 2H), 7.45 (s, 1H).

Example 5

1-[(Phosphonomethoxy)methoxymethyl]thymine disodium salt (5)

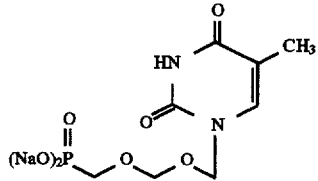

(5)

To a solution of 1-[3-(ethylphosphonomethoxy) methoxymethyl]thymine sodium salt (300 mg, 0.9 mmol) in dry DMF (5 mL) was added bromotrimethylsilane (1.5 mL) under nitrogen. After stirring 3 hr at 25° C., volatiles were removed in vacuo and the residue was dissolved in aqueous saturated bicarbonate and re-evaporated in vacuo to a solid foam. Purification of this material by a $C_{18}$ reverse phase column chromatography using water as eluent under 8 psi pressure and lyophilization of combined fractions gave the title compound as a white amorphous foam: Yield 140 mg (48%).

Analysis: Calcd. for $C_8H_{11}N_2O_7PNa_2$: C, 29.64; H, 3.42; N, 8.64. Found: C, 29.91; H, 3.61; N, 9.16.

$UV_{max}$ ($H_2O$): 266 nm ($\epsilon$=8100).

$^1$H-NMR (200 MHz, $D_2O$): δ1.75 (s, 3H), 3.27 (d, J=8.5 Hz, 2H), 4.71 (s, 2H), 5.11 (s, 2H), 7.74 (s, 1H).

Example 6

2-Amino-6-chloro-9-[(diethylphosphonomethoxy) methoxymethyl]purine (6)

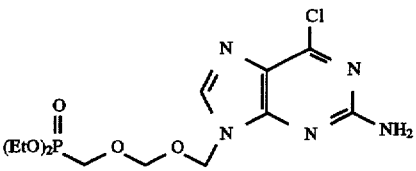

(6)

To a suspension of 60% sodium hydride in mineral oil (1.4 g, 34.5 mmol) in n-pentane (100 mL) at 0° C. was added dropwise diethyl phosphate (4.4 mL, 34.5 mmol) under nitrogen. After stirring for 1 hr at 0° C., a solution of bis(chloromethoxy)methane (25 g, 172 mmol) [prepared according to the literature procedure: P. R. Strapp, J. Org. Chem., 34, 1143 (1969)] in n-pentane (50 mL) was added at −70° C. The mixture was stirred for 90 min at 0° C. and then the solvent was evaporated under reduced pressure. The residual oil was dissolved in xylene and volatiles were removed in vacuo to give crude chloromethoxy (diethoxyphosphonomethoxy)methane. Without further purification, this material was used for the next reaction.

To a suspension of 60% sodium hydride in mineral oil (1.4 g, 34.5 mmol) in DMF (100 mL) was added 2-amino-6-chloropurine (5.78 g, 34.2 mmol) and the mixture was stirred for 1 hr at 25° C. To the resulting yellow solution was added dropwise a solution of above chloromethoxy (diethylphosphonomethoxy)methane in DMF (20 mL) under nitrogen. After stirring 15 hr at 25° C., volatiles were removed in vacuo. The residual oil was suspended in ethyl acetate (100 mL), washed with water (30 mL), brine and dried ($MgSO_4$). The solvent was removed under reduced pressure, and the residual oil was chromatographed on silica gel using $CH_2Cl_2$/3% MeOH as eluent to give the title compound as a colorless oil: yield 3.0 g (23%).

$^1$H-NMR (300 MHz, $CDCl_3$): δ1.395 (t, J=6.9 Hz, 6H), 3.850 (d, J=9.0 Hz, 2H), 4.05–4.20 (m, 4H), 4.697 (s, 2H), 5.323 (bs, 2H), 5.578 (s, 2H), 7.889 (s, 1H).

Example 7

9-[(Methylphosphonomethoxy)methoxymethyl]guanine sodium salt (7)

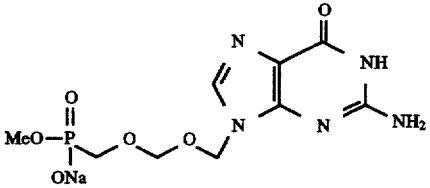

(7)

To a solution of 2-amino-6-chloro-9-[3-(diethylphosphonomethoxy)methoxymethyl] purine (325 mg, 0.84 mmol) in methanol (5 mL) was added 1N sodium methoxide in methanol (10 mL). The solution was heated at 80° C. for 1 hr under nitrogen. Volatiles were removed under reduced pressure. The residual oil was then dissolved in water (10 mL) and the solution was heated at 100° C. for 1 hr. The pH of the solution was carefully adjusted to 8.0 at 0° C. by dropwise addition of 1N HCl. Water was then evaporated in vacuo and the residual oil was purified by a $C_{18}$ reverse phase column using water as eluent to give the title compound as a white solid: yield 185 mg (60%).

$UV_{max}$ ($H_2O$): 254 nm ($\epsilon$=14,372), 274 nm ($\epsilon$=9,788).

$^{13}$C-NMR (75.47 MHz, $D_2O$): δ51.875, 60.464, 63.627, 70.005, 94.711, 94.952, 116.171, 139.925, 151.665, 154.428, 159.278.

$^1$H-NMR (300 MHz, D$_2$O): δ3.677 (d, J=10.3 Hz, 3H), 3.620 (d, J=9.0 Hz, 2H), 4.817 (s, 2H), 5.539 (s, 2H), 7.882 (s, 2H).

Example 8

9-[3-(Phosphonomethoxy)methoxymethyl]guanine disodium salt (8)

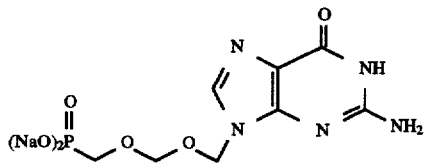
(8)

To a solution of 9-[(methylphosphonomethoxy)methoxymethyl]guanine (1.5 g, 4.4 mmol) in DMF (5 mL) was added bromotrimethylsilane (5 mL) under nitrogen. After stirring 3 hr at 25° C., the volatiles were removed in vacuo and the residue was neutralized to pH 8.0 by addition of aqueous saturated sodium bicarbonate. Water was then evaporated in vacuo, and the residue was purified by a C$_{18}$ reverse phase column using water as eluent under 8 psi pressure to give the title compound as a white powder: yield 900 mg (59%).

UV$_{max}$ (H$_2$O): 252 nm (ε=12,113), 274 nm (ε=8,201).

$^{13}$C-NMR (75.47 MHz, D$_2$O): δ67.016, 69.018, 70.746, 95.680, 95.831, 118.192, 141.812, 153.576, 157.386, 162.493.

$^1$H-NMR (300 MHz, D$_2$O): δ3.525 (d, J=8.9 Hz, 2H), 4.766 (s, 2H), 5.539 (s, 2H), 7.892 (s, 1H).

Example 9

9-[(Diethylphosphonomethoxy)methoxymethyl]adenine (9)

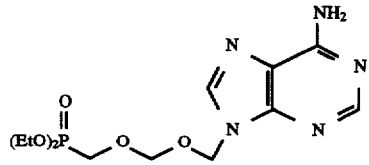
(9)

To a suspension of 60% sodium hydride in mineral oil (1.4 g, 34.5 mmol) in DMF (100 mL) was added adenine (4.7 g, 34.5 mmol) and the mixture was stirred at 80° C. for 1 hr. To the resulting yellow solution was added dropwise a solution of chloromethoxy(diethoxyphosphinomethoxy)methane [(prepared from diethylphosphate (4.4 mL, 34.5 mmol) and bis(chloromethoxy)methane (25 g, 172 mmol)] in DMF (20 mL) under nitrogen. After stirring at 25° C. for 15 hr, volatiles were removed in vacuo, and the resulting oily residue was purified by silica gel column chromatography using CH$_2$Cl$_2$/10% MeOH as eluent to obtain the title compound as a colorless oil: yield 6.0 g (50%).

$^1$H-NMR (300 MHz, CDCl$_3$): δ1.390, (t, J=6.7 Hz, 6H), 3.821 (d, J=9.2 Hz, 2H), 4.05–4.18 (m, 4H), 4.785 (s, 2H), 5.690 (s, 2H), 6.20 (bs, 2H), 7.921 (s, 1H), 8.295 (s, 1H).

Example 10

9-[3-(Phosphonomethoxy)methoxymethyl]adenine disodium salt (10)

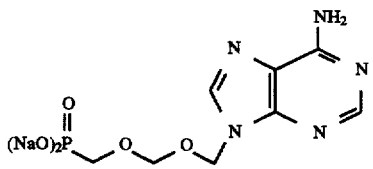
(10)

To a solution of 9-[(diethylphosphonomethoxy)methoxymethyl]adenine (600 mg, 1.7 mmol) in DMF (4 mL) was added bromotrimethylsilane (5 mL) under nitrogen. After stirring 3 hr at 25° C. the volatiles were removed in vacuo and the residue was neutralized to pH 8.0 by addition of aqueous saturated sodium bicarbonate. Water was then evaporated in vacuo, and the residue was purified by a C$_{18}$ reverse phase column using water as eluent under 8 psi pressure to give the title compound as a white powder: yield 280 mg (50%).

Analysis: Calcd. for C$_8$H$_{10}$N$_5$O$_5$PNa$_2$ (3H$_2$O+0.2 mol NaCl): C, 22.08; H, 4.72; N, 16.10. Found: C, 22.15; H, 4.64; N, 16.26.

UV$_{max}$ (H$_2$O): 260 nm (ε=12,016)

$^{13}$C-NMR (75.47 MHz, D$_2$O): δ66.913, 68.917, 71.033, 95.729, 95.940, 120.228, 144.611, 150.754, 154.766, 157.370.

$^1$H-NMR (300 MHz, D$_2$O): δ3.486 (d, J=8.9 Hz, 2H), 4.779 (s, 2H), 5.710 (s, 2H), 8.177 (s, 1H), 8.226 (s, 1H).

Example 11

1-[(Diethylphosphonomethoxy)methoxymethyl]cytosine (11)

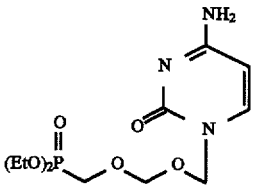
(11)

To a suspension of 60% sodium hydride in mineral oil (700 mg, 17 mmol) in DMF (50 mL) was added cytosine (1.9 g, 17 mmol) and the mixture was heated at 80° C. for 2 hr under nitrogen. To the resulting yellow solution was added dropwise a solution of chloromethoxy (diethylphosphonomethoxy)methane [prepared from diethylphosphate (2.4 g, 17 mmol) and bis-(chloromethoxy) methane (1.25 g, 86 mmol)] in DMF (10 mL) under nitrogen. After stirring 15 hr at 25° C., the volatiles were removed in vacuo. The residue was dissolved in ethyl acetate (120 mL) and water (30 mL). The organic phase was washed with brine and dried (MgSO$_4$). After removal of the solvent in vacuo, the residual oil was chromatographed on silica gel using CH$_2$Cl$_2$/10% MeOH as eluent to give the title compound as a white oil: yield 1.2 g (22%).

$^1$H-NMR (300 MHz, CDCl$_3$): δ1.390 (t, J=6.9 Hz, 6H), 1.90 (bs, 2H), 3.815 (d, J=9.0 Hz, 2H), 4.05–4.20 (m, 4H), 4.752 (s, 2H), 5.20 (s, 1H), 5.853 (d, J=7.4 Hz, 1H), 7.312 (d, J=7.4 Hz, 1H).

Example 12

1-[(Phosphonomethoxy)methoxymethyl]cytosine disodium salt (12)

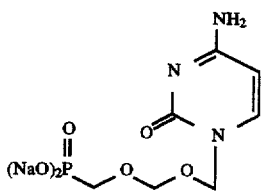

To a solution of 1-[diethylphosphonomethoxy) methoxymethyl]cytosine (1.2 g, 3.7 mmol) in DMF (5 mL) was added bromotrimethylsilane (5 mL) under nitrogen. After stirring 3 hr at 25° C., the volatiles were removed in vacuo and the residue was neutralized to pH of 8.0 by the addition of aqueous saturated sodium bicarbonate. Water was then evaporated in vacuo and the residue was purified by a $C_{18}$ reverse phase column using water as eluent under 8 psi pressure to give the title compound as a white solid: yield 460 mg (47%).

Analysis: Calcd. for $C_7H_{11}N_3O_6PNa_2$ (3 $H_2O+5\%$ NaCl); C, 21.99; H, 4.22; N, 10.99. Found: C, 21.72; H, 4.65; N, 10.78.

$UV_{max}$ ($H_2O$): 268 nm ($\epsilon=8,245$)

$^{13}$C-NMR (75.47 MHz, $D_2O$): $\delta$66.876, 68.873, 77.710, 96.141, 96.284, 98.178, 148.355, 160.409, 162.543.

$^1$H-NMR (300 MHz, $D_2O$): $\delta$3.560 (d, J=9.0 Hz, 2H), 4.849 (s, 2H), 5.313 (s, 2H), 6.03 (d, J=7.3 Hz, 1H), 7.714 (d, J=7.3 Hz, 1H).

Example 13

[2-(Phenylselenyl)ethoxy]methyl chloride (13)

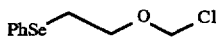

To a solution of 2-(phenylselenyl)ethanol (4.0 g, 20 mmol) [prepared according to the literature procedure: P. Rollin, V. V. Bencomo, P. Sinay, Synthesis, 13 (1984)] in $CH_2Cl_2$ (15 mL) was added paraformaldehyde (620 mg, 20 mmol). HCl gas was then bubbled into the solution at 5° C. for 2 hr. The solution was dried ($MgSO_4$), and the solvent was removed under reduced pressure to give the title compound as a colorless oil in a quantitative yield.

$^1$H-NMR (300 MHz, $CDCl_3$: $\delta$3.059 (t, J=7.0 Hz, 2H), 3.882 (t, J=7.0 Hz, 2H), 5.449 (s, 2H), 7.2–7.5 (m, 5H).

Example 14

2-Amino-6-chloro-9-[(2-phenylselenyl)ethoxymethyl] purine (14)

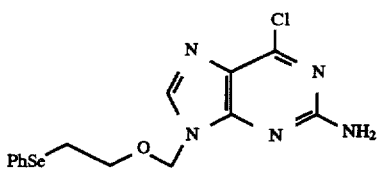

A mixture of 2-amino-6-chloropurine (20 g, 118 mmol) and ammonium sulfate (400 mg) in hexamethyldisilazane (400 mL) and chlorotrimethylsilane (6 mL) was heated at 145° C. for 5 hr under nitrogen. Volatiles were removed in vacuo and the residue was evaporated with xylene twice, and further dried in vacuo for 3 hr. The crude silylated 2-amino-6-chloropurine (15 g, 72 mmol) and mercuric cyanide (15 g, 59 mmol) in benzene (900 mL) was heated at reflux for 30 min, then a solution of 2-(phenylselenyl) ethoxymethylchloride (17 g, 68 mmol) in benzene (100 mL) was added. The mixture was refluxed for 3 hr, and then allowed to stir for 15 hr at 25° C. The reaction was diluted with $CH_2Cl_2$ (300 mL), and quenched with aqueous saturated bicarbonate (2 L). The organic phase was washed with 2N potassium iodide (200 mL), dried ($MgSO_4$), and the solvents were removed in vacuo. The residual oil was chromatographed on silica gel using $CH_2Cl_2/5\%$ MeOH as eluent to provide the title compound as a slightly yellow foam: yield 15.0 g (63%).

Analysis: Calcd. for $C_{14}H_{14}N_5OClSe.1/2 H_2O$; C, 42.93; H, 3.86; N, 17.88. Found: C, 42.92: H, 3.80: N, 17.59

$^1$H-NMR (300 MHz, $CDCl_3$): $\delta$2.961 (t, J=6.9 Hz, 2H), 3.704 (t, J=6.9 Hz, 2H), 5.196 (bs, 2H), 5.420 (s, 2H), 7.1–7.4 (m, 5H), 7.806 (s, 1H).

$^{13}$C-NMR (75.47 MHz, $CDCl_3$): $\delta$26.041, 69.144, 72.710, 127.206, 128.653, 128.846, 131,232, 136.062, 144.946, 151.190, 151.833, 152.298.

Example 5

2-Acetamido-6-chloro-9-[(2-(phenylselenyl)ethoxymethyl] purine (15)

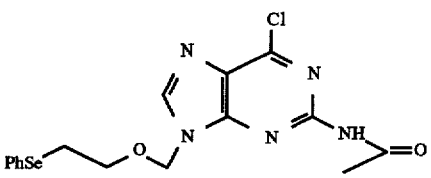

A solution of 2-amino-6-chloro-9-[(2-phenylselenyl) ethoxymethyl]purine (8 g, 21 mmol) in acetic anhydride (80 mL) was heated at 55° C. for 40 hr. Volatiles were removed in vacuo and the residual oil was purified by silica gel column chromatography using $CH_2Cl_2/40\%$ EtOAc as eluent to give the title compound as a yellow powder: yield 5.8 g (65%).

Analysis: Calcd. for $C_{16}H_{16}N_5O_2ClSe$: C, 45.25: H, 3.80; N, 16.49. Found: C, 45.12; H, 3.90; N, 16.47.

$^1$H-NMR (300 MHz, $CDCl_3$): $\delta$2.49 (s, 3H), 2.961 (t, J=6.9 Hz, 2H), 3.756 (t, J=6.9 Hz, 2H), 5.541 (s, 2H), 7.2–7.4 (m, 5H), 8.063 (s, 1H).

Example 16

2-Acetamido-6-chloro-9-(vinyloxymethyl)purine (16)

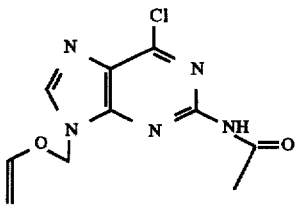

To a solution of 2-acetamido-6-chloro-9-[(2-(phenylselenyl)ethoxymethyl]purine (424 mg, 1 mmol) in methanol (20 mL) was added sodium bicarbonate (92 mg, 1.1 mmol) and sodium periodate (320 mg, 1.5 mmol). After stirring at 25° C. for 30 min the mixture was filtered and evaporated to dryness. The residue was dissolved in dioxane (20 mL) and the solution was heated at 80° C. for 20 min under nitrogen. The solution was evaporated in vacuo and the residual oil was chromatographed on silica gel using $CH_2Cl_2/20\%$ MeOH as eluent to give the title compound as a slightly yellow foam: yield 220 mg (60%).

Example 17

2-Acetamido-6-chloro-9-[(1-(dimethylphosphonomethoxy)ethoxy)methyl]purine (17)

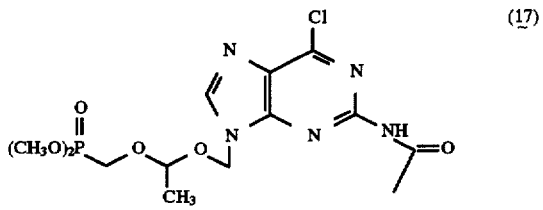

To a solution of 2-acetamido-6-chloro-9-(vinyloxy)purine (2.2 g, 6.0 mmol) and dimethylphosphonomethanol (1.67 g, 12.0 mmol) in chloroform (100 mL) was added 120 mg of methanesulfonic acid. After heating at 60° C. for 2 hr, the solvent was removed in vacuo and the residual oil was chromatographed on silica gel using $CH_2Cl_2$/10% MeOH as eluent to give the title compound as a colorless oil: yield 1.2 g (50%).

$^{13}$C-NMR (75.47 MHz, $CDCl_3$): 18.794, 25.054, 53.064, 53.218, 55.743, 59.056, 68.071, 99.254, 99.502, 127.921, 144.576, 151.598, 152.645, 170.299.

$^1$H-NMR (300 MHz, $CDCl_3$): δ1.347 (d, J=8.1 Hz, 3H), 2.519 (s, 3H), 3.852 (d, J=16.2 Hz, 6H), 5.029 (q, J=8.1 Hz, 1H), 5.648 (d, J=15.6 Hz, 1H), 5.791 (d, J=15.6 Hz, 1H), 7.275 (s, 1H), 8.201 (s, 1H).

Example 18

9-[(1-(Phosphonomethoxyethoxy)methyl]guanine disodium salt (18)

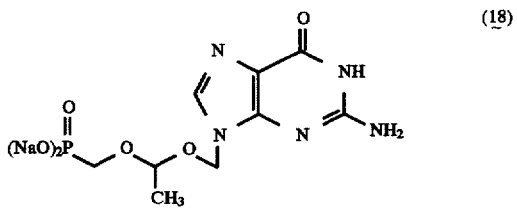

To a solution of 2-acetamido-6-chloro-9-[(1-dimethylphosphonomethoxy)ethoxy)methyl]purine (1.2 g, 2.95 mmol) in methanol (5 mL) was added 1N sodium methoxide in methanol (10 mL). After stirring at 25° C. for 1 hr, water (10 mL) was added and the solution was heated at 90° C. for 1 hr under nitrogen. Volatiles were removed in vacuo and the residual oil was purified by $C_{18}$ reverse phase column chromatography using water as eluent under 8 psi pressure. Each 10 mL fraction was assayed by high pressure liquid chromatography. The combined fractions were lyophilized to give a white solid. This material was dissolved in DMF (20 mL) followed by bromotrimethylsilane (5 mL). After stirring 2 hr at 25° C., volatiles were removed in vacuo and the residue was purified by a $C_{18}$ reverse phase column using water as eluent under 8 psi pressure to give the title compound as white amorphous powder after lyophilization: yield 245 mg (24%).

Analysis: Calcd. for $C_9H_{12}N_5O_6PNa_2 \cdot 4H_2O$: C, 25.78, H, 4.80; N, 16.70. Found: C, 25.93; H, 4.44; N, 16.91.

$UV_{max}$ ($H_2O$): 252 nm (ε=9751).

$^{13}$C-NMR (75.47 MHz, $D_2O$): δ20.859, 64.079, 66.088, 70.423, 102.054, 102.241, 119.11, 140.287, 153.110, 162.211, 168.712.

Analysis: Calcd. for $C_{10}H_{10}N_5O_2Cl$: C, 44.88; H, 3.77; N, 26.17. Found: C, 44.57; H, 3.83; N, 25.82.

$^1$H-NMR (300 MHz, $D_2O$): δ1.195 (d, J=6.3 Hz, 3H), 3.305 (dd, J=8.9, 8.4 Hz, 1H), 3.496 (dd, J=8.9, 8.4 Hz, 1H), 4.874, (q, J=6.3 Hz, 1H), 5.475 (dd, J=14.0, 11.1 Hz, 1H), 5.523 (dd, J=14.0, 11.1 Hz, 1H), 7.790 (s, 1H).

Example 19

1-(5-Methoxytetrahydro-2-furyl) thymine (19)

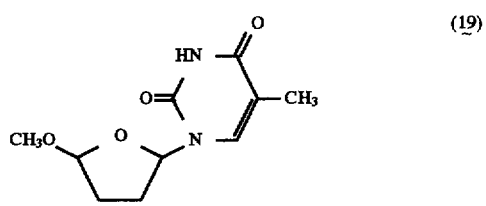

To a suspension of thymine (2.5 g, 20 mmol) in hexamethyldisilazane (30 mL) was added ammonium sulfate (50 mg) and chlorotrimethylsilane (0.5 mL) and the mixture was heated at 145° C. for 4 hr under nitrogen. The excess hexamethyldisilazane was removed at reduced pressure, and the residual oil was dissolved in xylene and evaporated in vacuo to give a colorless viscous oil. To this silylated thymine in dichloroethane (40 mL) was added 2,5-dimethoxytetrahydrofuran (7 mL). After cooling the solution to −30° C., tin tetrachloride (2.3 mL) was added dropwise via a syringe under nitrogen. The mixture was allowed to warm to −10° C. and was then poured into ice cold aqueous sodium bicarbonate (100 mL) and ethyl acetate (150 mL). The mixture was filtered and the organic phase was separated and dried ($MgSO_4$). The solvent was removed under reduced pressure and the residual oil was chromatographed on silica gel using $CH_2Cl_2$/5% MeOH as eluent to give the title compound as a cis/trans mixture in a ratio of 1:1 as shown by analytical HPLC and $^1$H-NMR: yield 3.4 g (75%).

Analysis: Calcd. for $C_{10}H_{14}N_2O_4$: C, 53.08; H, 6.24; N, 12.39. Found: C, 52.81; H, 6.22; N, 12.38.

$UV_{max}$ (EtOH): 266 nm (ε=9076).

$^1$H-NMR (300 MHz, $CDCl_3$): δ1.4–2.1 (m, 7H), 3.40 and 3.425 (two s, 3H), 5.20 and 5.328 (two bs, 1H), 6.208 and 6.417 (two dd, J=3.5, 7.0 Hz and 7.2, 7.2 Hz, 1H), 7.021 and 7.40 (bs, 1H).

The cis/trans (19A/19B) mixture was separated by a careful silica gel column chromatography. Thus, the cis isomer 19A was eluted first with $CH_2Cl_2$/3% MeOH and obtained as a white needle. The X-ray crystallography and the NOE (Nuclear Overhauser Effect) NMR confirmed the cis stereochemical arrangement of 19A. m.p. 153°–154° C.

Analysis: Calcd. for $C_{10}H_{14}N_2O_4$: C, 53.09; H, 6.24; N, 12.38. Found: C, 52.92; H, 6.20; N, 12.10.

$^{13}$C-NMR (75.47 MHz, $CDCl_3$): δ12.634, 29.417, 32.157, 55.202, 105.883, 111.411, 135.952, 139.553, 150.938, 163.906.

$^1$H-NMR (300 MHz, $CDCl_3$): δ1.950 (s, 3H), 1.9–2.3 (m, 4H), 3.40 (s, 3H), 5.20 (t, J=2.9 Hz, 1H), 6.417 (dd, J=4.0, 7.2 Hz, 1H), 7.40 (s, 1H), 8.781 (s, 1H).

Continuing the column with $CH_2Cl_2$/3% MeOH, the trans isomer 19B was eluted after the cis isomer 19A and was obtained as white needles. The NOE observation of 19A was consistent with the assigned structure: m.p. 124°–125° C.

Analysis: Calcd. for $C_{10}H_{14}N_2O_4$: C, 53.09; H, 6.24; N, 12.38. Found: C 53.10; H, 6.10; N, 12.00.

$^1$H-NMR (75.47 MHz, $CDCl_3$): δ1.920 (s, 3H), 2.0–2.5 (m, 4H), 3.425 (s, 3H), 5.328 (dd, J=2.5, 6.0 Hz, 1H), 6.208 (dd, J=3.5, 7.0 Hz, 1H), 7.021 (s, 1H), 8.885 (s, 1H).

Example 20

1-(4-Dimethylphosphonomethoxytetrahydro-2-furyl)thymine (20)

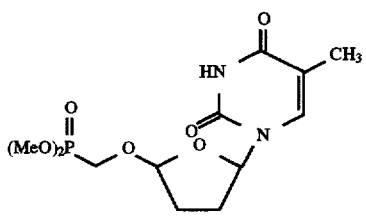

To a solution of 1-(5-methoxytetrahydro-2-furyl)thymine (5.2 g, 23 mmol) and dimethylphosphonomethanol (6.5 g, 44 mmol) in toluene was added acetic acid (5 mL) and p-toluenesulfonic acid monohydrate (500 mg, 2.6 mmol). The solution was heated at 100° C. for 2 hr and the resulting insoluble solid was removed by suction filtration. After removal of the solvent under reduced pressure, the residual oil was chromatographed on silica gel using $CH_2Cl_2/5\%$ MeOH as eluent to give the title compound as a cis/trans mixture (6:4): yield 5.0 g (60%).

$^1$H-NMR (300 MHz, $CDCl_3$): δ1.9–2.2 (m, 10H), 3.8–4.1 (m, 6H), 5.198, 5.445 (bs, 0.6 and 0.4H), 6.250 (dd, J=2.8, 7.5 Hz, 0.4H), 6.437 (t, J=7.4 Hz, 0.6H), 7.052 (s, 0.4H), 7.405 (s, 0.6H), 9.60 (bs, 0.6H), 7.628 (bs, 0.4H).

Example 21

1-(4-Methylphosphonomethoxytetrahydro-2-furyl)thymine sodium salt (21)

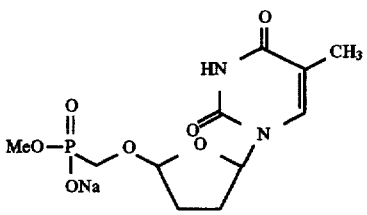

To a solution of 1-(4-dimethylphosphonomethoxytetrahydro-2-furyl)thymine (5 g, 14.6 mmol) in methanol (10 mL) was added 2N sodium hydroxide (20 mL). After stirring 2 hr at 25° C., the reaction was neutralized to pH 8.0 by addition of 3N HCl with stirring. Water was then evaporated in vacuo and the residual oil was purified by a $C_{18}$ reverse phase column using water as eluent to give the title compound as a white powder. This material was shown to be a 1:1 cis/trans (21A/21B) mixture by analytical HPLC and $^1$H-NMR: yield 3.2 g (65%).

Analysis: Calcd. for $C_{11}H_{16}N_2O_7NaP \cdot 2H_2O$: C, 34.92; H, 5.29; N, 7.40. Found: C, 34.93; H, 4.99; N, 7.43.

$UV_{max}$ ($H_2O$): 268 nm (ε=8668).

$^1$H-NMR (300 MHz, $D_2O$): δ1.842 (s, 1.5H), 1.894 (s, 1.5H), 1.9–2.5 (m, 4H), 3.571 (d, J=9.8 Hz, 1H), 3.589 (d, J=9.2 Hz, 1H), 3.59–3.85 (m, 2H), 5.239 (d, J=3.5 Hz, 0.5H), 5.483 (d, J=4.7 Hz, 0.5H), 6.198 (q, J=2.9 Hz, 0.5H), 6.331 (t, J=6.0 Hz, 0.5H), 7.371 (s, 0.5H), 7.561 (s, 0.5H).

The cis/trans mixture was separated by a reverse phase column (100 time weight) using water/3% acetonitrile as eluent under 6 psig pressure. Each 15 mL fraction was assayed by HPLC. The cis isomer 21A was eluted first and obtained as a white powder.

$^1$H-NMR(300 MHz, $D_2O$): δ1.894 (s, 3H), 2.0–2.45 (m, 4H), 3.571 (d, J=9.8 Hz, 2H), 3.595 (dd, J=7.4, 10.0 Hz, 1H), 3.781 (dd, J=7.4, 10.8 Hz, 1H), 5.239 (d, J=3.5 Hz, 1H), 6.331 (t, J=6.0 Hz, 1H), 7.561 (s, 1H).

After cis/trans mixture fractions, the pure trans isomer 21B was also obtained as a white powder.

$^1$H-NMR (300 MHz, $D_2O$): δ1.842 (s, 3H), 2.0–2.5 (m, 4H), 3.589 (d, J=9.2 Hz, 2H), 3.611 (dd, J=9.2, 10.0 Hz, 1H), 3.840 (dd, J=9.2, 10.0 Hz, 1H), 5.483 (d, J=4.3 Hz, 1H), 6.198 (q, J=2.9 Hz, 1H), 7.371 (s, 1H).

The stereochemical assignment of the cis and trans isomers was confirmed by the NOE (Nuclear Overhauser Effect) NMR.

Example 22

1-(4-Phosphonomethoxytetrahydro-2-furyl)thymine disodium salt (22)

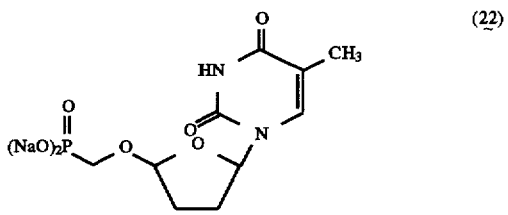

To a solution of 1-(4-methylphosphonotetrahydro-2-furyl)thymine sodium salt (1.2 g, 3.5 mmol) in DMF (15 mL) was added bromotrimethylsilane (10 mL) under nitrogen. After stirring 4 hr at 25° C., the volatiles were removed in vacuo and the residual oil was neutralized to pH 8.0 by the addition of aqueous sodium bicarbonate. Water was then evaporated in vacuo, and the residue was purified by a $C_{18}$ reverse phase column using water as eluent under 8 psi pressure to give the title compound as a white powder: yield 857 mg (70%).

Analysis: Calcd. for $C_{10}H_{13}N_2O_7PNa_2 \cdot 5H_2O$: C, 27.26; H, 5.20; N, 6.36. Found: C, 27.14; H, 5.26; N, 6.03.

$UV_{max}$ ($H_2O$): 268 nm (ε=7.350).

$^1$H-NMR (300 MHz, $D_2O$): δ1.864 (s, 1.5H), 1.928 (s, 1.5H), 1.95–2.90 (m, 4H), 3.4–3.6 (m, 2H), 5.363 (t, J=3.0 Hz, 0.5H), 5.56 (d, J=4.2 Hz, 0.5H), 6.212 (dd, J=2.7, 5.8 Hz, 0.5H), 6.321 (t, J=3.9 Hz, 0.5H), 7.435 (s, 0.5H), 7.679 (s, 0.5H).

Example 23

1-[2,3-Dideoxy-4-β-chloro-3-(phenylselenyl)-β-D-erythrofuranosyl]thymine (23)

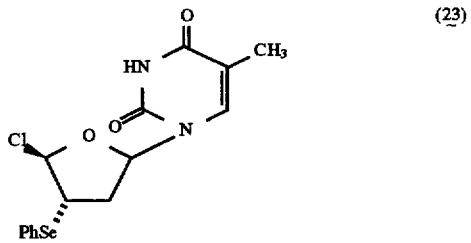

To a solution of 1-(2,3-dideoxy-3,-4-didehydro-β-D-erythrofuranosyl)thymine (1.94 g, 10 mmol) [prepared according to the literature procedure: J. Zemlicka, R. Gasser, J. V. Freisler, J. P. Horwitz, J. Amer. Chem. Soc., 94, 3213 (1972)] in $CH_2Cl_2$ (30 mL) was added at −70° C. dropwise a solution of phenylselenyl chloride (1.92 g, 10 mmol) in $CH_2Cl_2$ (5 mL) under nitrogen. After stirring at −70° C. for 1 hr, the solvent was removed in vacuo to give the title compound as a yellowish oil. This material was used for the next reaction without further purification.

¹H-NMR (300 MHz, CDCl₃): δ1.95 (s, 3H), 2.5–2.8 (m, 2H), 4.18 (d, J=6.5 Hz, 1H), 6.20 (s, 1H), 6.55 (q, J=6.0, 7.5 Hz, 1H), 7.1–7.7 (m, 6H), 9.30 (broad, 1H).

Example 24

1-[2,3-Dideoxy-4-β-(dimethylphosphono)methoxy-3-(phenyselenyl)-β-D-erythrofuranosyl]thymine (24)

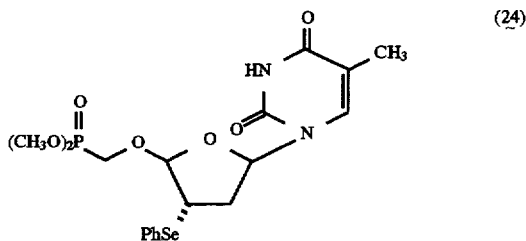

To a solution of 1-[2,3-dideoxy-4-chloro-3-(phenylselenyl)-β-D-erythrofuranosyl]thymine (3.85 g, 10 mmol) and dimethoxyphosphinylmethanol (1.5 g, 11 mmol) in CH₂Cl₂ (20 mL) was added dropwise at −70° C. a solution of silver perchlorate (2.3 g, 11 mmol) in CH₃CN (3 mL) over 3 min under nitrogen. The mixture was allowed to warm to 0° C. and was then poured into aqueous saturated bicarbonate (10 mL)-brine (15 mL). The organic phase was separated after filtration and dried (MgSO₄). The solvents were removed under reduced pressure, and the residual oil was purified by silica gel column chromatography using CH₂Cl₂/5% MeOH as eluent to give the title compound as a colorless oil: yield 1.3 g (31%).

¹H-NMR (300 MHz, CDCl₃): δ1.93 (s, 3H), 2.45 (m, 2H), 3.70 (dd, J=8.4, 8.0 Hz, 1H), 3.75 (d, J=12.0 Hz, 6H), 3.85 (d, J=6.9 Hz, 1H), 3.90 (dd, J=8.4, 8.0 Hz, 1H), 5.10 (s, 1H), 6.52 (s, 1H), 7.35 (s, 1H), 8.86 (bs, 1H).

Example 25

1-[2,3-Dideoxy-2,3-didehydro-4-phosphonomethoxy-β-D-erythrofuranosyl]thymine disodium salt (25)

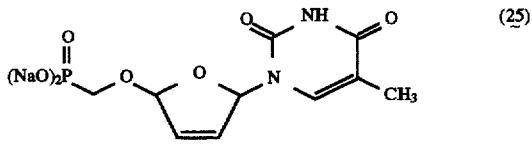

To a solution of 1-[2,3-dideoxy-4-(dimethylphosphono)methoxy-3-(phenylselenyl-β-D-erythrofuranosyl]thymine (1.15 g, 2.76 mmol) in DMF (4 mL) was added at 5° C. bromotrimethylsilane (3 mL) under nitrogen. After stirring for 4 hr at 5° C., volatiles were removed in vacuo and the residue was dissolved in aqueous saturated bicarbonate (3 mL) and evaporated again in vacuo to give a slightly yellow solid.

¹H-NMR (200 MHz, D₂O): δ1.79 (s, 3H), 2.3–2.5 (m, 2H), 3.27 (1, J=7.6, 8.4 Hz, 1H), 3.50 (1, J=7.6, 8.4 Hz, 1H), 3.93 (d, J=6.9 Hz, 1H), 5.23 (s, 1H), 6.0 (t, J=6.9 Hz, 1H), 7.53 (s, 1H).

The reaction product from the above example was dissolved in water (5 mL) followed by sodium periodate (1.7 g, 8.0 mmol). After stirring for 30 min, the reaction mixture was heated at 80° C. for 8 min and then filtered. The filtrate was evaporated to dryness and the residual solid was purified by a C₁₈ reverse phase column chromatography using water as eluent under 8 psi pressure. Each 15 mL fraction was assayed by high pressure liquid chromatography. Lyophilization of combined fractions gave the title compound as a white amorphous solid: yield 538 mg (50%); m.p. 233°–237° C.

Analysis: Calcd. for C₁₀H₁₁N₂O₇Na₂P.H₂O: C, 32.61; H, 3.51; N, 7.61. Found: C, 32.31; H, 3.63; N, 7.35.

¹³C-NMR (50.3 MHz, D₂O): δ13.921, 67.870, 69.848, 89.868, 111.242, 111.364, 113.908, 131.177, 134.655, 39.350.

¹H-NMR (300 MHz, D₂O): δ1.848 (s, 3H), 3.565 (dd, J=8.4, 8.7 Hz, 1H), 3.738 (dd, J=8.4, 8.7 Hz, 1H), 5.987 (s, 1H), 6.180 (d, J=6.0 Hz, 1H), 6.432 (d, J=6.0 Hz, 1H), 6.817 (s, 1H), 7.377 (s, 1H).

UV$_{max}$ (H₂O): 266 nm (ε=10,134).

Example 26

1-[2,3-Dideoxy-2,3-didehydro-4-β-(dimethylphosphono)methoxy-β-D-erythrofuranosyl)thymine (26)

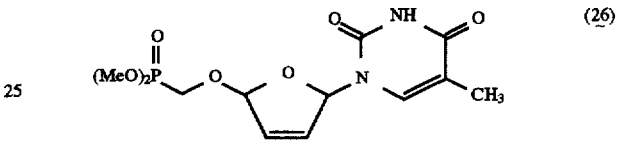

To a solution of 1-(2,3-dideoxy-4-β-(dimethylphosphono)methoxy-3-(phenylselenyl)-β-D-erythrofuranosyl]thymine (6.0 g, 12.2 mmol) in methanol (20 mL) was added dropwise a suspended solution of sodium bicarbonate (1.8 g, 21 mmol) and sodium periodate (3.2 g, 15 mmol) in water (20 mL). After stirring at 25° C. for 1 hr, the mixture was heated at 80° C. for 60 min. Volatiles were removed in vacuo and the residue was suspended in CH₂Cl₂ (120 mL). After removal of insoluble material, the organic phase was dried (MgSO₄) and evaporated in vacuo. The residue was chromatographed on silica gel using CH₂Cl₂/5% MeOH as eluent to give the title compound as a white amorphous powder: yield 3.4 g (85%).

Analysis: Calcd. for C₁₂H₁₇N₂O₇P: C, 43.38; H, 6.16; N, 8.43. Found: C, 43.53; H, 5.20; N, 8.26.

¹³C-NMR (75.47 MHz, CDCl₃): δ12.339, 52.889, 52.976, 53.080, 60.491, 62.738, 87.837, 108.402, 108.569, 111.653, 130.613, 131.675, 135.435, 150.480, 163.503.

¹H-NMR (300 MHz, CDCl₃): δ1.862 (s, 3H), 3.748 (d, J=12.8 Hz, 3H), 3.814 (d, J=12.8 Hz, 1H), 3.826 (dd, J=8.9, 8.4 Hz, 1H), 3.902 (dd, J=8.9, 8.4 Hz, 1H), 5.711 (s, 1H), 6.075 (d, J=5.7 Hz, 1H), 6.233 (d, J=5.7 Hz, 1H), 6.915 (s, 1H), 7.129 (s, 1H), 8.95 (bs, 1H).

Example 27

1-[2,3-Dideoxy-2,3-didehydro-4-β-(methylphosphono)methoxy-β-D-erthyrofuranosyl]thymine sodium salt (27)

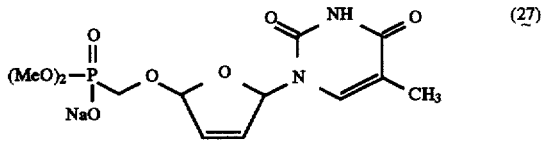

A solution of 1-[2,3-dideoxy-2,3-dihydro-4-β-(dimethylphosphono)methoxy-β-D-2-erythrofuranosyl] thymine (180 mg, 0.54 mmol) in 1N NaOH (2 mL) was stirred at 25° C. for 2 hr. The reaction was carefully neutralized to pH 8.0 by dropwise addition of 1N HCl with good stirring. Water was then evaporated in vacuo and the residue was purified by a $C_{18}$ reverse phase column using water/3% acetonitrile as eluent to give the title compound as a white solid: yield 125 mg (68%).

Analysis: Calcd. for $C_{11}H_{14}N_2O_7PNa.1.5\ H_2O$: C, 34.28; H, 4.93; N, 7.27. Found: C, 34.02; H, 49.4; N, 7.19.

$UV_{max}$ ($H_2O$): 269 nm (ε=8160)

$^1H$-NMR (300 MHz, $D_2O$): δ1.847 (s, 3H), 3.525 (d, J=11.0 Hz, 3H), 3.917 (dd, J=13.6, 17.0 Hz, 1H), 3.765 (dd, J=13.6, 17.0 Hz, 1H), 5.849 (s, 1H), 6.198 (d, J=4.6 Hz, 1H), 6.415 (d, J=4.6 Hz, 1H), 6.847 (s, 1H), 7.374 (s, 1H).

Example 28

1-[2,3-Dideoxy-4-β-(methylphosphono)methoxy-β-D-erythrofuranosyl]thymine sodium salt (28)

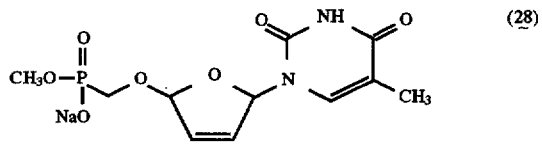

To a solution of 1-[2,3-dideoxy-2,3-didehydro-4-β-(methylphosphono)methoxy-β-D-erythrofuranosyl]thymine sodium salt (300 mg, 0.9 mmol) in water (20 mL) was added 10% palladium on active carbon (200 mg) and hydrogenated for 30 min under 35 psi $H_2$ pressure. The catalyst was filtered and washed with methanol (30 mL). The combined filtrate and wash was evaporated in vacuo and the residue was purified by a $C_{18}$ reverse phase column using water/2% acetonitrile under 8 psi pressure to give the title compound as a white solid: yield 250 mg (84%).

This material showed an identical nmr with compound 21A which was prepared from 2,5-dimethoxytetrahydrofuran and the stereochemical assignment of compound 21A was confirmed by the NOE.

$^1H$-NMR (300 MHz, $D_2O$): δ1.943 (s, 3H), 2.168 (m, 2H), 2.418 (m, 2H), 3.608 (d, J=6.9 Hz, 3H), 3.68 (dd, J=13.5, 18.0 Hz, 1H), 3.85 (dd, J=13.5, 18.0 Hz), 5.303 (s, 1H), 6.390 (d, J=6.3 Hz, 1H), 7.627 (s, 1H).

In a manner similar to the above Example 28, the thymine-containing reactant can be replaced with a corresponding adenine, guanine or cytosine reactant to produce 1-[2,3-dideoxy-2,3-didehydro-4-β-(methylphosphono)methoxy-β-D-erythrofuranosyl]adenine sodium salt, or 1-[2,3-dideoxy-2,3-didehydro-4-β-(methylphosphono)methoxy-β-D-erythrofuranosyl]guanine sodium salt, or 1-[2,3-dideoxy-2,3-didehydro-4-β-(methylphosphono)-methoxy-β-D-erythrofuranosyl cytosine sodium salt.

Example 29

1-[4-β-(Dimethylphosphono)methoxy-β-D-erythrofuranosyl]thymine (29)

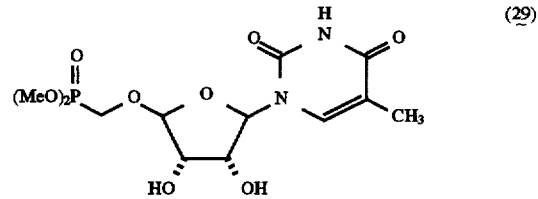

To a solution of 1-[2,3-dideoxy-2,3-didehydro-4-β-(dimethylphosphono)methoxy-β-D-erythro-furanosyl] thymine (3.31 g, 10 mmol ) in pyridine (20 mL) was added osmium tetroxide (2.54 g, 10 mmol) at 0° C. and stirred for 2 hr. The solvent was removed in vacuo. The residue was dissolved in ethyl acetate (100 mL), washed with 10% phosphoric acid (30 mL), water (20 mL), aqueous sodium bicarbonate (20 mL), brine and dried $MgSO_4$). The solvent was removed in vacuo, and the residual oil was chromatographed on silica gel using $CH_2Cl_2$/5% MeOH as eluent to give the title compound as a white powder: yield 2.56 g (70%).

Analysis: Calcd. for $C_{12}H_{19}N_2O_9P$: C, 39.35; H, 5.23; N, 7.65. Found: C, 38.98; H, 5.09; N, 7.42.

$^{13}C$-NMR (75.47 MHz, DMSO-$d_6$): δ11.861, 52.672, 52.797, 59.114, 61.411, 72.608, 73.316, 73.399, 87.419, 107.607, 107.863, 110.810, 135.217, 150.973, 163.581.

$^1H$-NMR (300 MHz, DMSO-$d_6$): δ1.675 (s, 3H), 3.540 (d, J=10.5 Hz, 6H), 3.736 (1, J=4.0 Hz, 1H), 3.817 (d, J=9.6 Hz, 2H), 4.03 (dd, J=6.0, 11.2 Hz, 1H), 4.763 (s, 1H), 5.35 (d, J=4.0 Hz, 1H), 5.45 (d, J=7.0 Hz, 1H), 5.919 (d, J=6.9 Hz, 1H), 7.128 (s, 1H), 11.228 (bs, 1H).

In a manner similar to the above Example 29, the thymine-containing reactant can be replaced with a corresponding adenine, guanine or cytosine reactant to produce 9-[4-β-(dimethylphosphono)methoxy-β-D-erythrofuranosyl]adenine, or 9-[4-β-(dimethylphosphono)methoxy-β-D-erythrofuranosyl]guanine, or 1-[4-β-(dimethylphosphono)methoxy-β-D-erythrofuranosyl] cytosine.

Example 30

1-[4-(Methylphosphono)methoxy-β-D-erythrofuranosyl] thymine sodium salt (30)

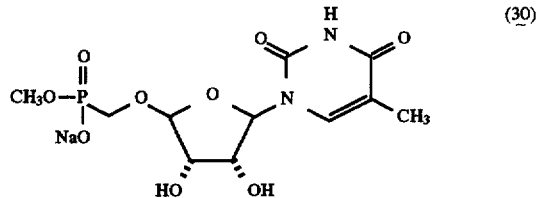

To a solution of 1-[4-β-(dimethylphosphonomethoxy-β-D-erythrofuranosyl]thymine (200 mg, 0.5 mmol) in 1N NaOH (2 mL) was stirred at 25° C. for 2 hr. The reaction was carefully neutralized to pH 9.0 by dropwise addition of 1N HCl with stirring. Water was then evaporated in vacuo and the residual oil was purified by a $C_{18}$ reverse phase column using water/2% acetonitrile as eluent under 8 psi pressure to give the title compound as a white amorphous powder: yield 114 mg (56%).

Analysis Calcd. for $C_{11}H_{15}N_2O_9PNa.2H_2O$: C, 32.27; H, 4.64; N, 6.84. Found: C, 31.94; H, 4.32; N, 6.86.

$UV_{max}$ ($H_2O$): 268 nm (ε=8153).

$^{13}C$-NMR (75.47 MHz, $D_2O$): δ35.644, 35.719, 45.366, 47.479, 57.032, 57.411, 71.915, 92.426, 92.599, 96.463, 120.503, 137.007, 144.422, 151.377.

$^1H$-NMR (300 MHz, $D_2O$): δ1.922 (s, 3H), 3.615 (d, J=10.1 Hz, 3H), 3.687 (dd, J=11.3, 11.1 Hz, 1H), 3.885 (dd, J=11.3, 11.1 Hz, 1H), 4.220 (d, J=4.3 Hz, 1H), 4.574 (dd, J=6.7, 4.3 Hz, 1H), 5.09 (s, 1H), 6.175 (d, J=6.7, Hz, 1H), 7.485 (s, 1H).

In a manner similar to the above Example 30, the thymine-containing reactant can be replaced with a corresponding adenine, guanine or cytosine reactant to produce 1-[4-β-(methylphosphono)methoxy-β-D-erythrofuranosyl] adenine, or 1-[4-β-(methylphosphono)methoxy-β-D- erythrofuranosyl]guanine, or 9-[4-β-(methylphosphono)methoxy-β-D-erythrofuranosyl]cytosine.

Example 31

9-(4-β-Phosphonomethoxy-β-D-erythrofuranosyl)thymine disodium salt (31)

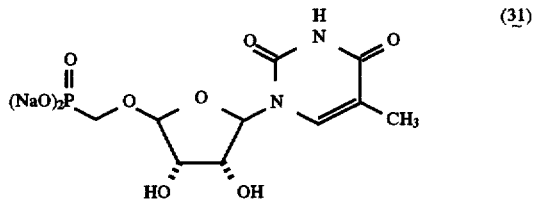

To a solution of 1-[4-β-(dimethylphosphono)methoxy-β-D-erythrofuranosyl]thymine (320 mg, 0.87 mmol) in DMF (2 mL) was added at 0° C. bromotrimethylsilane (1.4 mL) under nitrogen. After stirring 90 min at 0° C., volatiles were removed in vacuo and the residue was neutralized to pH 8.0 by addition of aqueous saturated sodium bicarbonate. Water was then evaporated in vacuo and the residual solid was purified by a $C_{18}$ reverse phase column using water/2% acetonitrile as eluent to give the title compound as a white solid: yield 153 mg (46%), m.p. >250° C. (dec.).

Analysis: Calcd. for $C_{10}H_{13}N_2O_9PNa.2H_2O$: C, 27.52; H, 4.35; N, 6.42. Found: C, 27.05; H, 3.99; N, 6.12.

$UV_{max}$ ($H_2O$): 268 nm (ε=7,568).

$^{13}C$-NMR (75.47 MHz, $D_2O$): δ49.590, 51.582, 57.347, 57.541, 71.861, 93.034, 93.169, 95.541, 121.178, 136.393, 144.222, 150.601.

$^1H$-NMR (300 MHz, $D_2O$): δ1.936 (s, 3H), 3.469 (dd, J=12.3, 12.6 Hz, 1H), 3.756 (dd, J=12.3, 12.6 Hz, 1H), 4.258 (d, J=4.5 Hz, 1H), 4.578 (dd, J=4.5, 6.2 Hz, 1H), 5.175 (s, 1H), 6.182 (d, J=6.2 Hz, 1H), 7.591 (s, 1H).

In a manner similar to the above Example 31, the thymine-containing reactant can be replaced with a corresponding adenine, guanine or cytosine reactant to produce 1-[4-β-phosphonomethoxy-β-D-erythrofuranosyl]adenine disodium salt, or 1-[4-β-phosphonomethoxy-β-D-erythrofuranosyl]guanine disodium salt, or 1-[4-β-phosphonomethoxy-β-D-erythrofuranosyl]cytosine disodium salt.

Example 32

1-[2-Deoxy-4-β-(diethylphosphono)methoxy-β-D-erythrofuranosyl]thymine (32A) and the trans isomer

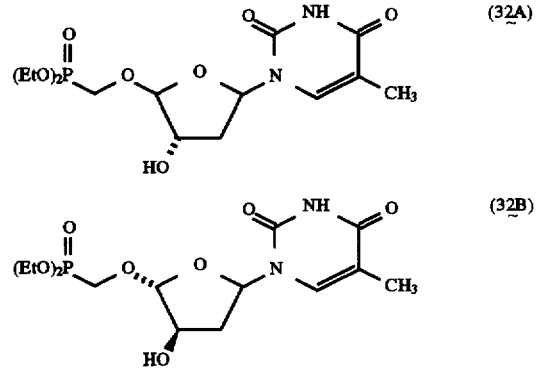

To a solution of 1-(2,3-dideoxy-3,4-didehydro-β-D-erythrofuranosyl)thymine (2.4 g, 12.4 mmol) and diethylphosphonomethanol (17.4 g, 103 mmol) in $CH_2Cl_2$ (2 mL) was added 80–85% 3-chloroperoxybenzoic acid (17.4 g, 13.14 mmol) at 5° C. After stirring for 60 min at 25° C., the reaction mixture was purified by column chromatography on silica gel using $CH_2Cl_2$/3% MeOH to obtain the crude product, which was carefully rechromatographed on silica gel to separate the two isomers. Using $CH_2Cl_2$/1% MeOH, the minor isomer B was first eluted and obtained as a colorless oil: yield 75 mg (1.7%).

$^1H$-NMR (300 MHz, $CDCl_3$) of 32B: δ1.287 (t, J=6.9 Hz, 6H), 1.900 (s, 3H), 1.97–2.58 (m, 2H), 3.807 (dd, J=9.0, 13.8 Hz), 4.016 (dd, J=9.0, 13.8 Hz, 1H), 4.138 (m, 4H), 4.30 (m, 1H), 4.934 (d, J=4.2 Hz, 1H), 6.321 (t, J=6.6 Hz, 1H), 7.417 (s, 1H), 9.80 (bs, 1H).

The silica gel column was continuously eluted with $CH_2Cl_2$/3% MeOH to obtain the major isomer 32A as a colorless oil: yield 735 mg (17%).

$^1H$-NMR (300 MHz, $CDCl_3$) of 32A: δ1.310 (t, J=7.5 Hz, 6H), 1.872 (s, 3H), 1.95 (m, 1H), 2.70 (m, 1H), 3.780 (dd, J=9.3, 13.8 Hz, 1H), 3.928 (dd, J=9.3, 13.8 Hz, 1H), 4.139 (m, 4H), 4.330 (d, J=5.7 Hz, 1H), 5.268 (s, 1H), 6.238 (dd, J=2.7, 8.4 Hz, 1H), 7.624 (s, 1H), 9.176 (bs, 1H).

The stereochemical assignment of 32A and 32B was consistent with nmr NOE observation.

In a manner similar to the above Example 32, 1-(2,3-deoxy-3,4-didehydro-β-D-erythrofuranosyl)thymine can be replaced with a corresponding adenine, guanine or cytosine reactant to produce 9-[2-deoxy-4-β-(diethylphosphono)methoxy-β-D-erythrofuranosyl]adenine, 9-[2-deoxy-4-β-(methylphosphono)methoxy-β-D-erythro-furanosyl]adenine sodium salt, or 1-[2-deoxy-4-β-(diethylphosphono)methoxy-β-D-erythrofuranosyl]guanine, or 1-[2-deoxy-4-β-(diethylphosphono)methoxy-β-D-erythrofuranosyl]cytosine.

Example 33

1-(2-Deoxy-4-β-phosphonomethoxy-β-D-erythrofuranosyl)thymine disodium salt (33)

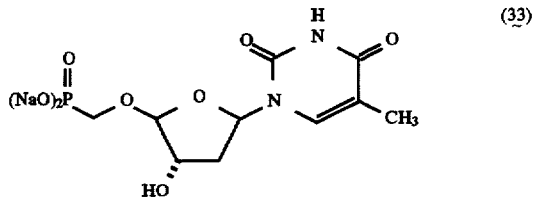

To a solution of 1-[2-deoxy-4-(diethylphosphono)methoxy-β-D-erythrofuranosyl]thymine (480 mg, 1.3 mmol) in DMF (2 mL) was added bromotrimethylsilane (2 mL) under nitrogen. After stirring 3 hr at 25° C., volatiles were removed in vacuo and the residue was carefully neutralized to pH 8.5 by addition of aqueous saturated sodium bicarbonate. Water was evaporated to dryness and the residual solid was purified by a $C_{18}$ reverse phase column using water/3% acetonitrile as a eluent to give the title compound as a white powder: yield 165 mg (40%).

Analysis: Calcd. for $C_{10}H_{13}N_2O_8PNa_2.3H_2O$: C, 28.57; H, 4.52; N, 6.67. Found: C, 28,48; H, 4.49; N, 6.52.

$UV_{max}$ ($H_2O$): 268 nm (ε=7,602).

$^{13}C$-NMR (75.47 MHz, $D_2O$): δ20.803, 48.289, 50.291, 56.714, 69.570, 94.015, 94.157, 94.994, 122.321, 135.750, 150.715.

$^1H$-NMR (300 MHz, $D_2O$): δ1.853 (s, 3H), 1.924 (dd, J=2.6, 13.4 Hz, 1H), 2.8–2.85 (dd, J=2.6, 5.3, 8.0 Hz, 1H), 3.415 (dd, J=8.9, 12.4 Hz, 1H), 3.669 (dd, J=8.9, 12.4 Hz,

1H), 4.372 (d, J=5.3 Hz, 1H), 4.372 (d, J=5.3 Hz, 1H), 4.372 (d, J=5.3 Hz, 1H), 5.310 (s, 1H), 6.285 (dd, J=2.6, 8.0 Hz, 1H), 7.776 (s, 1H).

In a manner similar to the above Example 33, the thymine-containing reactant can be replaced with a corresponding adenine, guanine or cytosine reactant to produce 9-(2-deoxy-4-β-phosphonomethoxy-β-D-erythrofuranosyl)adenine disodium salt, or D-(2-deoxy-4-β-phosphonomethoxy-β-D-erythrofuranosyl)guanine disodium salt, or 1-(2-deoxy-4-β-phosphonomethoxy-β-D-erythrofuranosyl)cytosine disodium salt.

Example 34

2-Acetamido-6-diphenylcarbamoyloxy-9-[2-(phenylselenyl)ethoxymethyl]purine (34)

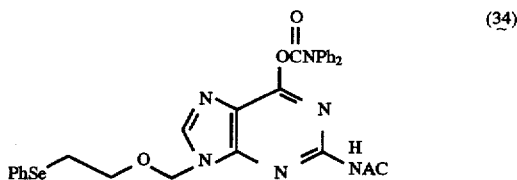
(34)

A mixture of 2-acetamido-6-diphenylcarbamoylpurine (36.7 g, 94.6 mmol) [prepared according to the following literature procedure: R. Zou and M. J. Ropbins, Can. J. Chem., 65, No. 6, 1436 (1987)] and N,O-bis-(trimethylsilyl) acetamide (47.6 mL, 193 mmol) in dry dichloroethane (700 mL) was heated at 80° C. for 60 min. Volatiles were removed in vacuo and the residue was evaporated with toluene twice. The silylated purine and mercuric cyanide (29.6 g, 117 mmol) in benzene (800 mL) was heated at reflux for 60 min, then a solution of 2-(phenylselenyl)-ethoxymethyl chloride (24 g, 94.5 mmol) in benzene (100 mL) was added dropwise. The mixture was refluxed for 4 hr and then allowed to stir for 15 hr at 25° C. The reaction was diluted with $CH_2Cl_2$ (500 mL) and quenched with aqueous saturated bicarbonate (1 L). The organic phase was washed with 2N potassium iodide (200 mL), dried ($MgSO_4$) and the solvents were removed in vacuo. The residual oil was chromatographed on silica gel using $CH_2Cl_2$/5% MeOH as eluent to provide the title compound as a slightly yellow powder: yield 22 g (39%).

Analysis: Calcd. for $C_{29}H_{25}N_6O_4Se$: C, 57.91, H, 4.36; N, 13.98. Found: C, 57.76; H, 4.46; N, 13.48.

$^1$H-NMR (300 MHz, $CDCl_3$): δ2.459 (s, 3H), 2.951 (t, J=6.9 Hz, 2H), 3.714 (t, J=6.9 Hz, 2H), 5.477 (s, 2H), 7.07–7.7 (m, 15H), 8.001 (s, 1H), 8.171 (s, 1H).

$^{13}$C-NMR (75.45 MHz; $CDCl_3$): δ25.133, 26.196, 69.192, 72.602, 120.363, 126.970, 127.014, 129.174, 141.686, 143.734, 150.247, 152.487, 155.232, 156.247, 156.297, 170.793.

Example 35

2-Acetamido-6-diphenylcarbamoyl-9-vinyloxymethyl)purine (35)

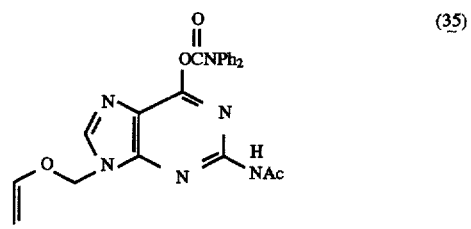
(35)

To a solution of 2-acetamido-6-diphenylcarbamoyl-9-[2-(phenylselenyl)ethoxymethyl]purine (4.92 g, 8.16 mmol) in dioxane (80 mL) was added 30% $H_2O_2$ (4 mL, 35 mmol) and sodium bicarbonate (2.1 g, 24.5 mmol). The mixture was heated at 60° C. for 20 min. The reaction was then concentrated to about 10 mL, diluted with ethyl acetate (100 mL), dried ($MgSO_4$) and the solvents were removed in vacuo. The residue was dissolved in dioxane (40 mL), diisopropylethylamine (1.27 g, 10 mmol) was added and the solution was heated at 80° C. for 30 min under nitrogen. The solvent was evaporated in vacuo and the residual oil was chromatographed on silica gel using $CH_2Cl_2$-ethyl acetate (1:1) as eluent to give the title compound as a yellowish powder: yield 2.3 g (65%).

Analysis: Calcd. for $C_{23}H_{20}N_6O_4.5H_2O$: C, 60.98; H, 4.67; N, 18.55. Found: C, 61.20; H, 4.76; N, 18.84.

$^1$H-NMR (300 MHz, $CDCl_3$): δ2.485 (s, 3H), 4.170 (dd, J=2.7, 6.6 Hz, 1H), 44.473 (dd, J=2.7, 14.1 Hz, 1H), 6.395 (dd, J=6.6, 14.1 Hz, 1H), 7.0–7.5 (m, 10H), 7.961 (s, 1H), 7.996 (s, 1H).

$^{13}$C-NMR (75.47 MHz, $CDCl_3$): δ25.121, 70.572, 92.427, 126.272, 126.344, 126.443, 126.496, 126.566, 126.644, 141.628, 143.226, 148.925, 152.552, 170.505.

Example 36

2-Acetamido-6-diphenylcarbamoyloxy-9-[(2-hydroxy-1-dimethylphosphonomethoxy)ethoxymethyl]purine (36)

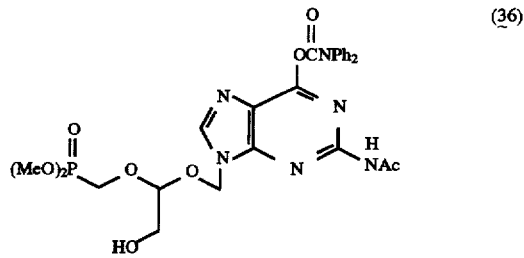
(36)

To a suspension of 2-acetamido-6-diphenyl-carbamoyloxy-9-(vinyloxymethyl)purine (1.0 g, 2.25 mmol) and dimethylphosphonomethanol (6 mL) in $CH_2Cl_2$ (6 mL) was added 80–85% m-chloroperbenzoic acid (611 mg, 3 mmol). After stirring for 18 hr at 25° C., the clear solution was diluted with $CH_2Cl_2$ (100 mL) and washed with ice cold 1N NaOH (4 mL) and brine (20 mL). The organic phase was washed again with brine (20 ML), dried ($MgSO_4$) and the solvent was removed in vacuo. The residual oil was chromatographed on silica gel using using $CH_2Cl_2$/5% MeOH as eluent to give the title compound as a colorless oil: yield 360 mg (27%).

Analysis: Calcd. for $C_{26}H_{29}N_6O_9P.0.5CH_2Cl_2$: C, 49.22; H, 4.64; N, 13.00. Found: C, 49.89; H, 4.47; N, 12.76.

$^1$H-NMR (300 MHz, $CDCl_3$): δ2.384 (s, 3H), 3.582 (dd, J=4.5, 12.5 Hz, 1H), 3.722 (dd, J=4.5, 12.5 Hz, 1H), 3.768 (dd, J=2.9, 10.7 Hz, 6H), 3.798 (dd, J=8.9, 14.0 Hz, 1H), 3.994 (dd, J=8.9, 14.0 Hz, 1H), 4.910 (t, J=4.9 Hz, 1H), 5.649 (d, J=10.8 Hz, 1H), 5.723 (d, J=10.8 Hz, 1H), 7.0–7.4 (m, 10H), 8.032 (s, 1H), 8.662 (s, 1H).

Example 37

9-[(2-Hydroxy-1-(methylphosphonomethoxyethoxymethyl] guanine ammonium salt (37)

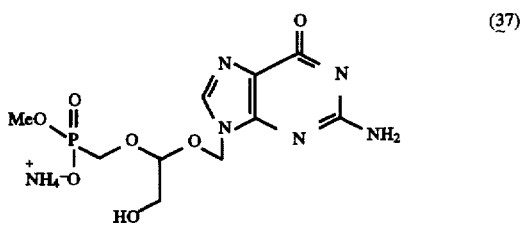

A solution of 2-acetamido-6-diphenylcarbamoyloxy-9-[(2-hydroxy-1-(dimethylphosphonomethoxy)ethoxy)methyl] guanine (2.9 g, 4.8 mmol) in methanol (300 mL) and 28% $NH_4OH$ (300 mL) was heated at 60° C. for 90 min The solution was concentrated in vacuo and the residual oil was purified by $C_{18}$ reverse phase column chromatography using water as eluent under 8 psi pressure. The fractions having ultraviolet fractions were checked with HPLC, combined and lyophilized to give the title compound as a white powder: yield 1.15 g (65%).

Analysis: Calcd. for $C_{10}H_{19}N_6O_7P \cdot H_2O$: C, 31.26; H, 5.51; N, 21.87. Found: C, 31.63; H, 5.43; N, 21.72.

$^1$H-NMR (300 MHz, $D_2O$): δ3.549 (d, J=10.5 Hz, 3H), 3.571 (dd, J=4.8, 13.2 Hz, 1H), 3.675 (dd, J=9.3, 13.2 Hz, 1H), 3.4–3.6 (m, 2H), 4.844 (t, J=3.9 Hz, 1H), 5.573 (d, J=11.4 Hz, 1H), 5.638 (d, J=11.4 Hz, 1H), 7.934 (s, 1H).

$UV_{max}$ ($H_2O$): 252 nm (ε=13,871).

Example 38

9-[(2-Hydroxy-1-(phosphonomethoxy)ethoxy)methyl] quanine disodium salt (38)

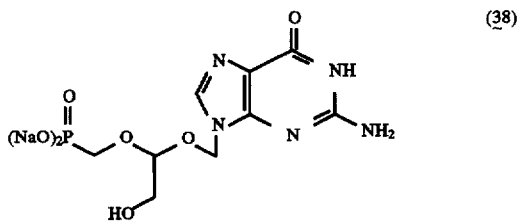

To a solution of 9-[2-hydroxy-1-(methylphosphonomethoxy)ethoxy)methyl]guanine ammonium salt (780 mg, 2.0 mmol) in dry DMF (20 mL) was added at 5° C. bromotrimethysilyl (8 mL, 60 mmol) under nitrogen. After stirring for 3 hr at 5° C., volatiles were removed in vacuo and the residue was dissolved in aqueous saturated bicarbonate and re-evaporated in vacuo to a solid. Purification of this material by $C_{18}$ reverse phase column chromatography using water as eluent under 8 psi pressure and lyophilization of combined fractions gave the title compound as a white powder: yield 520 mg (62%).

Analysis: Calcd. for $C_9H_{12}N_5O_7PNa_2 \cdot 2H_2O$: C, 26.04; H, 3.89; N, 16.87; Found: C, 26.25; H, 4.05; N, 16.89.

$UV_{max}$ ($H_2O$): 252 nm (ε=15,150).

$^1$H-NMR (300 MHz, $D_2O$): δ3.40–3.50 (m, 2H), 3.605 (dd, J=5.4, 11.6 Hz, 1H), 3.698 (dd, J =9.0, 11.6 Hz, 1H), 4.877 (t, J=4.5 Hz, 1H), 5.665 (d, J=11.3 Hz, 1H), 5.725 (d, J=11.3 Hz, 1H), 7.999 (s, 1H).

$^{13}$C-NMR (75.47 MHz, $D_2O$): δ63.268, 65.832, 7.834, 71.636, 104.561, 104.712, 117.980, 141.823, 53.521, 156.320, 161.129.

Example 39

1-(4-Methoxytetrahydro-2-furyl) thymine (3A)

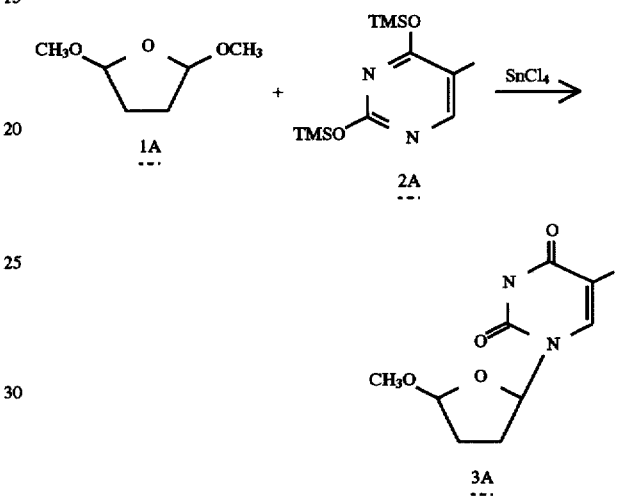

To a suspension of 2.5 g (20 mmol) of dry, powdered thymine in 30 mL of hexamethyldisilazane was added 50 mg of ammonium sulfate and 0.5 mL of trimethylsilyl chloride. The mixture was heated at 140°–145° for 4 hr to obtain a clear solution. The excess hexamethyldisilazane was removed at reduced pressure, then the residual white oil was dissolved in xylene and evaporated in high vacuum to give a colorless viscous oil. The crude silylated thymine was dissolved in 40 mL of dichloroethane and cooled to –30° C., followed by 7.8 g (60 mmol) of 2,5-dimethoxytetrahydrofuran. To this solution was added 2.3 mL of tin tetrachloride via a syringe over 2 min, then stirred for 10 min under nitrogen. The mixture reaction was poured into ice-cold aqueous $NaHCO_3$ (100 mL)-ethyl acetate (100 mL). The milky solution was filtered through celite and the organic layer was separated and dried over $MgSO_4$. Evaporation of the dried solvents gave a yellow oil which was chromatographed on $SiO_2$ ($CH_2Cl_2$/MeOH) to give 4.3 g (95%) of 3A as a colorless oil. This oil was a mixture of the two isomers (cis/trans) in a ratio of 1:1 as seen by analytical HPLC and $^1$H-NMR.

$^1$H-NMR ($CDCl_3$) δ1.4–2.2 (m, 7H), 3.40 and 3.42 (two s, 3H), 5.2 and 5.25 (two bs, 1H), 6.20 and 6.41 (two q, 1H, J=3.5, 7.0 Hz, and 4.0, 7.2 Hz), 7.02 and 7.40 (two s, 1H).

Example 40

1-(5-Diethylphosphonomethoxytetrahydro-2-furyl)thymine

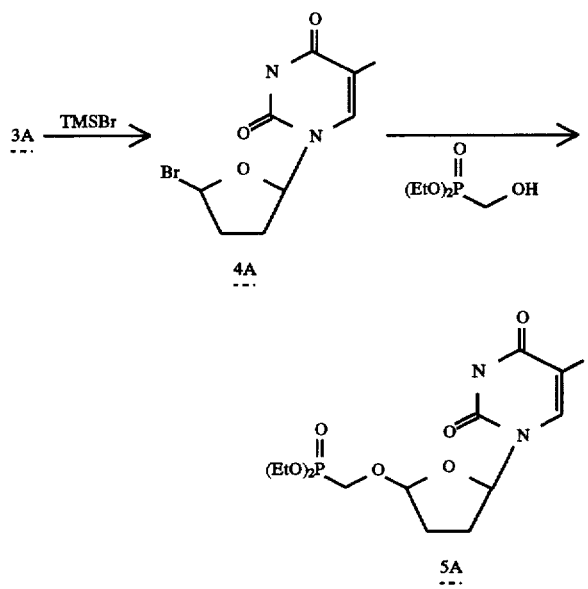

To a solution of 600 mg (2.65 mmol) of 3A (Example 39) in 15 mL of methylene chloride was added 0.6 mL of trimethylsilyl bromide and heated at 40°–45° C. for 10 min under nitrogen. The reaction was evaporated in vacuo to give 4A as a yellow oil which was dissolved in 20 mL of methylene chloride followed by 440 mg (2.60 mmol) of diethylphosphonomethyl alcohol. This solution was cooled to −10° C. followed by 0.6 mL of triethylamine and stirred for 15 min without the cooling bath. After dilution with 40 mL of ethyl acetate, the reaction was washed with water and brine. Evaporation of the dried (MgSO$_4$) solvent gave a yellow oil which was chromatographed over SiO$_2$ (CH$_2$Cl$_2$/ MeOH) to give 180 mg (18.5%) of 5A as a white oil. This oil was a mixture of the two isomers cis/trans in a ratio of 1:1, as seen by analytical HPLC and $^1$H-NMR; $^1$H-NMR (CDCl$_3$) δ1.25 (t, 6H, J=7.0 Hz), 1.95 and 2.0 (two s, 3H), 3.8–4.0 (m, 2H), 4.04–4.2 (m, 4H), 5.2 and 5.3 (two bs, 1H), 6.2 and 6.42 (q,q, 1H, J =3.5, 7.0 Hz and 4.0, 7.2 Hz), 7.0 and 7.4 (two s, 1H).

Example 41

Testing and evaluation of compounds against herpes virus
A. Plaque Reduction Assay Herpes simplex virus (HSV) strains were grown and titered at 37° C. in vero cells (African Green Monkey Kidney cells) and used for virus work before the tenth passage.

Cells were grown and maintained in Earle's Minimum Essential Medium (EMEM), Gibco Laboratories, supplemented with 0.75% sodium bicarbonate, 2 mM 1-glutamine, Pen-strep. and 5–10% fetal calf serum.

The titer of HSV strains is determined by a plaque titration method (Roizman and Roane, *Virology*, 115:75–79, 1961). Tissue culture 24-well petri dishes are seeded with cells and used for assays when approximately 75% monolayer. Volumes (0.1 mL) of logarithmic dilutions of the virus strain are inoculated onto each of triplicate wells, and absorbed for one hr with intermittent shaking. The inoculum thereafter is removed, and 1 mL of 5–10% EMEM containing 0.3% human immune serum globulin is added. After a 48 hr incubation period at 37° C. in a 5%CO$_2$ atmosphere, the overlay medium is removed and the cell sheets stained with Giemsa stain. The number of plaques is counted, the triplicate is averaged, and the number of plaque-forming units per mL is calculated.

The compounds are tested for activity against the herpes simplex stains using a stock solution of each compound freshly prepared. Appropriate dilution of each compound are made in 10% EMEM before usage. The antiviral efficacy of each compound is determined using the plaque reduction assay described above. Briefly, tissue culture 24-well plates, with approximately 50 plaque forming units of HSV per 0.1 mL, and the virus absorbed for 1 hr, with intermittent shaking. After removal of the inoculum, 1 mL of 10% EMEM containing two-fold dilutions of the appropriate drug are added in triplicates. Triplicate wells/plate receives no drug and are used as a virus control. After a 48-hr incubation period, at 37° C. in a 5% CO$_2$ atmosphere, the overlay medium is removed, the cells are stained as described above, and plaques are counted. The counts of triplicate wells are averaged, and the number of plaques in the presence of each drug dilution are calculated.

The antiviral potency of the drug is determined by ID$_{50}$, the drug concentration necessary to reduce the number of plaques by 50% of those in the virus control cultures.

The results are shown below in Table 1:

TABLE 1

Antiviral Test Results of Compound 8 (see Example 8) against HSV-1 and HSV-2

| Compound | ID$_{50}$ (µg/mL) | |
|---|---|---|
| | HSV-1 | HSV-2 |
| ACV (Acyclovir) | 0.5 | 0.5 |
| Compound 8 | 2.6 | 11 |

Example 42

Comparison of Compound 8 and Acyclovir (ACV) In Vivo

Groups of ten mice were inoculated intraperitoneally with from 200 to 600 PFU/0.2 mL of Herpes simplex virus-1 (HL-34 strain). Different doses of test compound were administered to separate groups of animals on a BID basis for five consecutive days commencing three hr after inoculation. Treatment was by an intraperitoneal route. The experiment was terminated 21 days post inoculation and the number of survivals in each group was counted. The mean survival time (MST, days) was calculated.

The results are shown in Table 2. Compound 8 is equally as active as ACV.

TABLE 2

Antiviral Effect of Compound 8 Against HSV-1 Systemic Infection in Mice

| Compound | Dose (mg/kg/d) | Route | Survival |
|---|---|---|---|
| Compound 8 | 300 | i.p. | 10/10 |
| | 100 | i.p. | 9/10 |
| | 10 | i.p. | 3/10 |
| ACV | 200 | i.p. | 6/7 |
| | 100 | i.p | 7/10 |

Treatment was initiated 3 hr post-infection and was given BID for 5 consecutive days.

Example 43

Testing and evaluating of compounds against Murine Retroviruses

The compounds were evaluated for antiviral activity against murine leukemia virus (MuLV) strains using the UV-XC plaque assay (Rowe, et al., *Virology*, 42:1136, 1970).

The MuLV strains were grown in fetal mouse cells (SC-1) and used for antiviral tests using the UV-XC plaque assay. Briefly, SC-1 cells are grown as monolayers in 4-well tissue culture plates and inoculated with approximately 50–100 plaque forming units of MuLV in 0.5 mL of 5% EMEM containing 20 µg/mL DEAE/Dextran. After 1 hr adsorption, the inoculum is removed and 5 mL of 5% EMEM containing three-fold. dilutions of the appropriate drug are added. Five days later, the cultures are UV-irradiated with an ultraviolet lamp and rat XC sarcoma cells are added to the cultures. Three-four days after UV-irradiation, the cell cultures are stained with Giemsa stain and the plaques are enumerated. Antiviral activity is expressed in terms of the reduction in the mean number of UX-XC plaques counted in the drug treated, virus-infected cultures compared with mean number of plaques counted in untreated, virus-infected control cultures.

Example 44

In Vitro Evaluation Against HIV

The following HIV in vitro assay was used: The anti-HIV/LAV activity is measured in cultures of CEM-F cells. The CEM cells are infected with approximately 30 TCID$_{50}$ (50% tissue culture infectious dose of HIV (LAV strain). The cells are then incubated for 45 min at 37° C. The test compounds in culture medium are added at various concentrations to the infected cells and then incubated for a further 8 days. After 8 days the antiviral activity was evaluated in the culture media supernatant for p24 gag protein by an enzyme capture assay (ELISA). The antiviral activity was expressed as the dose that inhibits 50% of the virus expression (ID$_{50}$ in µg/mL) as detected by the assay described.

TABLE 3

Antiviral Test Results of Compound 25 (see Example 25) against Retroviruses

| Compound | ID$_{50}$ (µg/ml) | |
|---|---|---|
|  | R-MuLV | HIV |
| AZT | 0.05 | 0.1 |
| Compound 25 | 0.3 | 1.8 |

Example 45

6-N-Pivaloyl-9-(2,3-dideoxy-3,4-dihydro-β-D-erythrofuranosyl)adenine

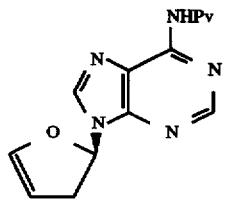

To a solution of 9-(2,3-dideoxy-3,4-dihydro-β-D-erythrofuranosyl)adenine (2.0 g, 10 mmol ) [prepared according to the literature procedure: J. Zemlicka, R. Gasser, J. V. Freisler, J. P. Horwitz, *J. Amer. Chem. Soc.*, 94, 3213 (1972)] in 1,2-dichloroethane (10 mL) was added pyridine (1 mL), dimethylaminopyridine (170 mg) and pivaloyl chloride (1.5 g, 12 mmol). The resulting solution was heated at 55°–60° C. for 6 hr under nitrogen. The mixture was then concentrated in vacuo, taken up in CH$_2$Cl$_2$ and washed with water, 20% H$_3$PO$_4$ and brine, dried over MgSO$_4$, and evaporated in vacuo. The residual oil was chromatographed on silica gel using CH$_2$Cl$_2$/3% MeOH as eluent to give the product (2.45 g, 85%) as a white powder.

$^1$H-NMR (CDCl$_3$) δ1.24 (s, 9H), 2.29 (ddd, J=3.5, 5.0, 17.1 Hz, 1H), 3.33 (dddd, J=2.4, 5.0, 9.4, 17.1 Hz, 1H), 5.24 (dd, J=2.4, 5.0 Hz, 1H), 6.41 (dd, J=3.5, 9.4 Hz, 1H), 6.48 (dd, J=2.4, 5.0 Hz, 1H), 8.18 (s, 1H), 8.73 (s, 1H).

Example 46

6-N-Pivaloyl-9-[2,3-dideoxy-4-β-chloro-3-α-(phenylselenyl)-β-D-erythrofuranosyl]adenine

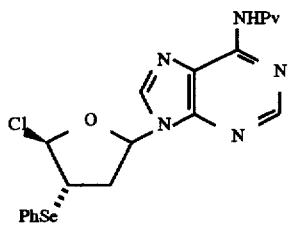

To a solution of the product of Example 45 (3.5 g, 12.2 mmol) in CH$_2$Cl$_2$ (40 mL) was added at –25° C. a solution of phenylselenyl chloride (2.7 g, 14.0 mmol) in CH$_2$Cl$_2$ (7 mL) over 5 min under nitrogen. After stirring for 30 min at –25° C., the solvent was removed in vacuo to give the product as a yellow oil. This material was used promptly for the next reaction:

$^1$H-NMR (CDCl$_3$) δ1.41 (s, 9H), 2.88 (m, 1H), 3.23 (m, 1H), 4.36 (d, J=6.3 Hz, 1H), 6.29 (s, 1H), 6.80 (dd, J=6.6, 8.4 Hz, 1H), 8.53 (s, 1H), 8.77 (s, 1H).

Example 47

6-N-Pivaloyl-9-[2,3-dideoxy-4-β-dimethylphosphonomethoxy-3-α-(phenylselenyl-β-α-D-erythrofuranosyl]adenine

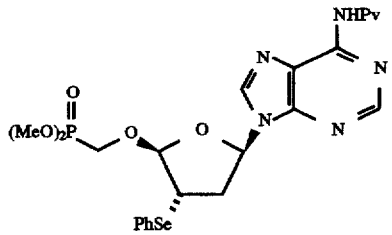

To a solution of the product of Example 46 (approximately 12 mmol) and dimethylhydroxymethylphosphonate (16.8 g, 120 mmol) [prepared according to the literature procedure: D. P. Philion and S. S. Andres, *Tetrahedron Lett.* 27, 1477 (1986)] in CH$_2$Cl$_2$ (15 mL) was added at –25° C. a suspended solution of silver perchlorate (4.0 g, 20 mmol) in CH$_2$Cl$_2$ (10 mL) and dimethyl hydroxymethylphosphonate (5 mL) over 5 min under nitrogen. The mixture was allowed to warm to 0° C., stirred for 60 min and was then poured into CH$_2$Cl$_2$ (100 mL)-aqueous bicarbonate (100 mL)-brine (50 mL). The organic phase was separated after filtration, dried over MgSO$_4$ and evaporated. The residual oil was chromatographed on silica gel using CH$_2$Cl$_2$/5% MeOH as eluent to give the product (3.2 g, 45%) as a colorless oil:

$^1$H-NMR (CDCl$_3$) δ1.25 (s, 9H), 2.61 (ddd, J=2.7, 6.6, 14.4 Hz, 1H), 2.96 (ddd, J=6.6, 7.5, 14.4 Hz, 1H), 3.68 (d, J=11 Hz, 6H), 3.7–4.0 (m, 3H), 5.24 (s, 1H), 8.27 (s, 1H), 8.67 (s, 1H).

Example 48

6-N-Pivaloyl-9-[2,3-dideoxy-2,3-dihydro-4-β-(dimethylphosphono)methoxy-β-D-erythrofuranosyl]adenine

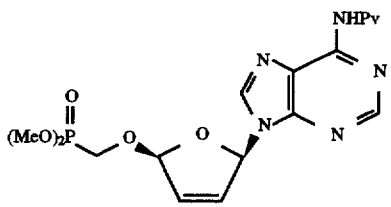

To a solution of the product of Example 47 (3.3 g, 5.6 mmol) in dioxane (30 mL) was added a solution of sodium periodate (6.3 g, 30 mmol) in water (30 mL) and the resulting solution was stirred at 23° C. for 4 hr. CH$_2$Cl$_2$ (200 mL) was added and the mixture was filtered through Celite. The organic phase was washed with water, brine, dried over MgSO$_4$ and evaporated in vacuo. The residual oil was chromatographed on silica gel using CH$_2$Cl$_2$/5% MeOH as eluent to give the product (1.4 g, 57%) as a colorless oil:

$^1$H-NMR (CDCl$_3$) δ1.31 (s, 6H), 3.64 (d, J=10.8 Hz, 3H), 3.71 (d, J=10.8 Hz, 3H), 3.84 (dd, J=8.7, 9.9 Hz, 1H), 5.87 (s, 1H), 6.27 (d, J=6.0 Hz, 1H), 6.34 (dd, J=1.5, 6.0 Hz, 1H), 7.00 (d, J=1.5 Hz, 1H), 8.04 (s, 1H), 8.66 (s, 1H);

$^{13}$C-NMR (CDCl$_3$) δ27.524, 40.607, 53.318 (d, J=6.2 Hz), 61.598 (d, J-165 Hz), 86.247, 109.202, 123.406, 130.657, 132.679, 141.966, 150.205, 152.056, 176.547.

Example 49

9-[2,3-Dideoxy-2,3-didehydro-4-β-(methylphosphono)methoxy-β-D-erythrofuranosyl]adenine ammonium salt

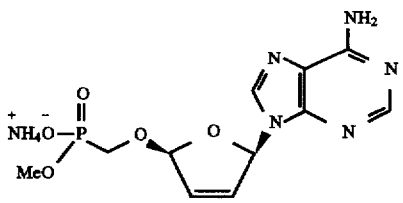

A solution of the product of Example 48 (330 mg, 0.78 mmol) and sodium methoxide (250 mg, 4.6 mmol) in methanol (10 mL) was stirred at 23° C. for 18 hr. The reaction was carefully neutralized to pH 5.0 by dropwise addition of 2N HCl in an ice bath. The pH of the solution was readjusted to 8.0 by concentrated NH$_4$OH and volatiles were removed in vacuo. The solid residue was purified by C$_{18}$ reverse-phase column using water as eluent under 8 psi pressure to give the product (141 mg, 49%) as a white amorphous powder:

$^1$H-NMR (D$_2$O) δ3.34 (d, J=10.5 Hz, 3H), 3.65 (dd, J=9.2, 13.2 Hz, 1H), 3.80 (dd, J=9.2, 13.2 Hz, 1H), 5.99 (s, 1H), 6.57 (s, 2H), 6.83 (s, 1H), 8.11 (s, 1H), 8.14 (s, 1H);

$^{13}$C-NMR (D$_2$O) 58.542 (d, J=3.0 Hz), 68.483 (d, J=150 Hz), 92.797, 116.319, 125.121, 136.147, 139.719, 147.131, 155.275, 159.781, 162.359;

UV$_{max}$ (H$_2$O) 260 nm (ε12,964).

Example 50

9-[2,3-Dideoxy-2,3-dihydro-4-β-phosphonomethoxy-β-D-erythrofuranosyl]adenine ammonium salt

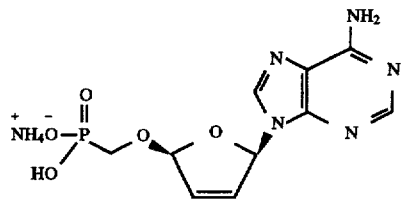

A solution of the product of Example 49 (310 mg, 0.9 mmol) and trimethylsilylbromide (1.0 mL) in DMF (4 mL) was stirred at 0° C. for 3 hr under nitrogen. Volatiles were removed in vacuo and the residue was dissolved in concentrated NH$_4$OH (2 mL). Water was evaporated in vacuo and the residual solid was purified by C$_{18}$ reverse-phase column using water as eluent under 8 psi pressure to give the product (128 mg, 43%) as a white amorphous powder.

UV$_{max}$ (H$_2$O) 260 nm (ε14,982);

$^1$H-NMR (D$_2$O) δ3.59 (dd, J=9.3, 22.2 Hz, 1H), 3.69 (dd, J=9.3, 22.2 Hz, 1H), 5.99 (s, 1H), 6.46 (d, J=6.0 Hz, 1H), 6.50 (d, J=6.0 Hz, 1H), 6.83 (s, 1H), 7.87 (s, 1H), 8.13 (s, 1H);

$^{13}$C-NMR (D$_2$O) δ70.756 (d, J=150 Hz), 93.065, 116.510, 122.434, 136.579, 139.835, 147.763, 155.424, 158.990, 161.809.

Anal. Calcd. for C$_{10}$H$_{15}$N$_6$O$_5$P·3H$_2$O: C, 31.25; H, 5.46; N, 21.87. Found: C, 31.32; H, 5.85; N, 22.15.

This compound was evaluated for anti-retroviral activity by the methods described in Examples 43 and 44. The results are shown in Table IV. AZT controls were run simultaneously to confirm the validity of the test.

TABLE IV

| Virus | Cell-line | Cell-tox. | ID$_{50}$ |
| --- | --- | --- | --- |
| HIV | CEM | >100 μm | 45 μm |
| HIV | MT-4 | >500 μm | 1.5 μm |
| R-MuLV | SC-1 | >100 μm | 0.01 μm |

Example 51

6-N-Pivaloyl-9-[2,3-dideoxy-4-β-(dimethylphosphonomethoxy-3-α-iodo-β-D-erythrofuranosyl]adenine

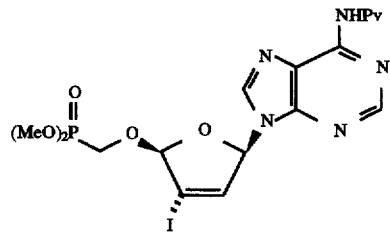

To a solution of the product of Example 45 (3.5 g, 12.2 mmol) and dimethyl hydroxymethylphosphonate (16.8 g, 120 mmol) in CH$_2$Cl$_2$ (40 mL) was added portionwise at 0° C. N-iodosuccinimide (2.75 g, 12.2 mmol) and the mixture was stirred for 2 hr at 0° C. The reaction was diluted with CH₂Cl₂ (50 mL), washed with water, brine, and dried over MgSO₄. The residual oil was chromatographed on silica gel using CH₂Cl₂/3% MeOH as eluent to give the product (4.9 g, 72%) as a slightly yellow oil.

¹H-NMR (CDCl₃) δ1.36 (s, 9H), 2.89 (dd, J=6.3, 9.7 Hz, 1H), 3.20 (dd, J=6.3, 10.3 Hz, 1H), 3.7–3.9 (m, 8H), 4.49 (d, J=5.4 Hz, 1H), 5.50 (s, 1H), 6.86 (t, J=7.2 Hz, 1H), 8.29 (s, 1H), 8.50 (bs, 1H), 8.74 (s, 1H).

Example 52

6-N-Pivaloyl-9-[2,3-dideoxy-2-3-dihydro-4-β-(dimethylphosphono)methoxy-β-D-erythrofuranosyl]adenine

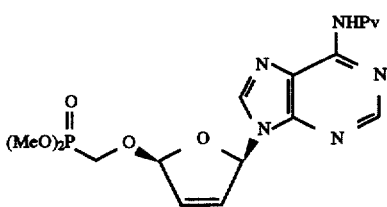

A solution of the product of Example 51 (1.7 g, 3.0 mmol) and 1,8-diazabicyclo[5.4.0]undec-7-ene (912 mg, 6.0 mmol) in CHCl₃ (20 mL) was heated at 65° C. for 2 hr. The reaction was washed with ice-cold 20% H₃PO₄, brine, dried over MgSO₄ and evaporated in vacuo. The residual oil was purified on silica gel using CH₂Cl₂/3% MeOH as eluent to give the product (1.2 g, 90%) as a colorless oil. This material was identical with the product of Example 48.

Example 53

1-[2,3-Dideoxy-4-β-(phosphonomethoxy)-β-D-erythrofuranosyl]thymine disodium salt

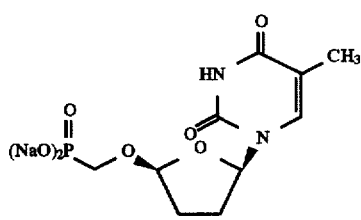

A mixture of the product of Example 25 (200 mg, 0.57 mmol) and 10% palladium on active carbon (180 mg) in water (20 mL) was hydrogenated for 30 min under 30 psi H₂ pressure in the Parr hydrogenator. The catalyst was filtered through Celite with the aid of a water wash. Water was removed by lyophilization to give the desired product (205 mg, 100%) as a white amorphous powder:

UV$_{max}$ (H₂O) 268 nm (ε8844);

¹H-NMR (D₂O) δ1.86 (s, 3H), 2.0–2.4 (m, 4H), 3.41 (dd, J=8.1, 12.9 Hz, 1H), 3.62 (dd, J=8.1, 12.9 Hz, 1H), 5.32 (t, J=2.7 Hz, 1H), 6.24 (t, J=7.0 Hz, 1H), 7.60 (s, 1H);

¹³C-NMR (D₂O) δ18.496, 35.384, 38.041, 72.628, (d, J=150 Hz), 93:249, 113.423, 118.884, 159.494, 174.169,

Anal. Calcd. for C₁₀H₁₃N₂O₇PNa₂.1 1/2 H₂O: C, 31.83; H, 4.24; N, 7.42. Found: C, 31.62; H, 3.95; N, 7.28

54

6-N-Pivaloyl-9-[4-β-(dimethylphosphono)methoxy-β-D-erythrofuranosyl]adenine

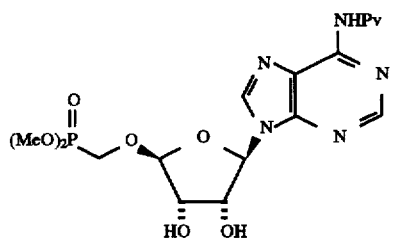

To a solution of phenylboric acid (860 mg, 7.0 mmol) and 4-methylmorpholine N-oxide (900 mg, 7.5 mmol) in CH₂Cl₂ (20 mL) was added, at 23° C., osmium tetroxide (25 mg) followed by the product of Example 52 (2.75 g, 6.4 mmol) in CH₂Cl₂ (10 mL). The mixture was stirred for 2 hr and 10% aqueous sodium bisulfite (4 mL) was added. After stirring for 1 hr, the CH₂Cl₂ was separated, washed with brine and dried over MgSO₄. Evaporation of solvent gave a white oil which was dissolved in acetone (15 mL) and 1,3-dipropanol (760 mg, 10 mmol ). All volatiles were removed in vacuo and the resulting oil was chromatographed over silica gel using CH₂Cl₂/7% MeOH as eluent to give the above-named compound (2.3 g, 76%) as a white foam:

¹H-NMR (CDCl₃) δ1.28 (s, 9H), 3.7 (d, J=10.5 Hz, 6H), 3.73 (dd, J=10.6, 13.5 Hz, 1H), 3.95 (d, J=10.6, 13.5 Hz, 1H) 4.91 (dd,J=4.5, 6.3 Hz, 1H), 4.33 (d, J=4.5 Hz, 1H), 5.09 (s, 1H), 6.38 (d, J=6.3 Hz, 1H), 8.35 (s, 1H), 8.49 (s, 1H), 8.83 (bs, 1H).

Example 55

9-[4-β-(Methoxyhydroxyphosphinyl)methoxy-β-D-erythrofuranosyl]adenine ammonium salt

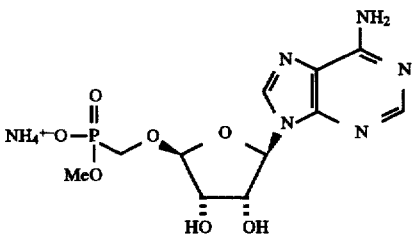

A solution of the product of Example 54 (2.2 g, 4.8 mmol) and sodium methoxide (1.49, 26 mmol) in methanol (50 mL) was stirred at 23° C. for 7 hr under nitrogen. Volatiles were removed in vacuo and the residual oil was dissolved in water (20 mL). The aqueous solution was heated at 35° C. for 10 hr. The reaction was carefully neutralized to pH 5.0 by dropwise addition of 2N HCl in an ice bath. The solution was then readjusted to pH 8.0 with concentrated NH₄OH and volatiles were removed in vacuo. The solid residue was purified by C₁₈ reverse-phase column using water/5% CH₃Cl as eluent under 8 psi pressure to give the product (1.3 g, 75%):

UV$_{max}$ (H₂O) 260 nm (ε10,019);

¹H-NMR (D₂O) δ3.56 (d, J=10.5 Hz, 3H), 3.61 (dd, J=10, 12.9 Hz, 1H), 3.83 (dd, J=10, 12.9 Hz, 1H), 4.38 (d, J=11.0 Hz, 1H), 5.0 (dd, J=6.2, 11.0 Hz, 1H), 5.19 (s, 1H);

¹³C-NMR (D₂O) δ53.897 (d, J=6.0 Hz), 64.192 (d, J=150 Hz), 75.589, 75,909, 111.096, 141,824, 151.079, 154.785, 157.354.

Example 56

9-[4-β-(phosphonomethoxy)methoxy-β-D-erythrofuranosyl]adenine ammonium salt

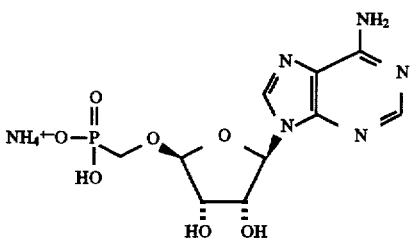

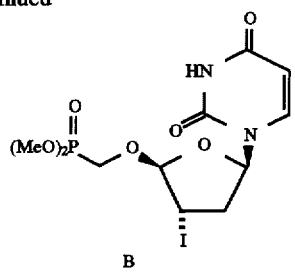

B

A solution of the product of Example 55 (1.5 g, 4.1 mmol) and trimethylsilyl bromide (7 mL) in DMF (30 mL) was stirred at 23° C. for 6 hr under nitrogen. The volatiles were removed in vacuo and the residue was dissolved in concentrated $NH_4OH$ (3 mL). Water was evaporated in vacuo and the residual solid was purified by $C_{18}$ reverse-phase column using water as eluent to give 12 (600 mg, 40%) as a white amorphous powder:

$UV_{max}$ ($H_2O$) 262 nm ($\epsilon$12,640);

$^1$H-NMR ($D_2O$) δ3.56 (dd, J=10.0, 12.9 Hz, 1H), 3.79 (dd, J=10.0, 12.9 Hz, 1H), 4.31 (d, J=11.0 Hz, 1H), 4.92 (dd, J=6.0, 11.0 Hz, 1H), 5.17 (s, 1H), 6.08 (d, J=10 Hz, 1H), 8.24 (s, 1H), 8.25 (s, 1H).

$^{13}$C-NMR ($D_2O$) δ66.296 (d, J=157 Hz), 75.881, 76.967, 88.982, 111.148, 119.927, 142.208, 150.689, 153.560, 156.330.

Anal. Calcd. for $C_{10}H_{17}N_6O_7P\cdot H_2O$: C, 30.05; H, 5.26; N, 21.03. Found: C, 30.09; H, 5.06; N, 20.38

Example 57

(2R,5R)-1-[2,5-Dihydro-5-(dimethoxyphosphinyl)methoxy-2-furanyl]uracil

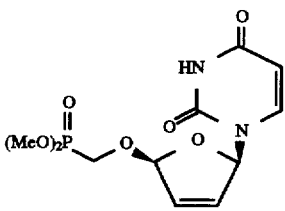

A. (2R,4S,5S)-1-[Tetrahydro-4-iodo-5-(dimethoxyphosphinyl)methoxy)methoxy-2-furanyl]uracil

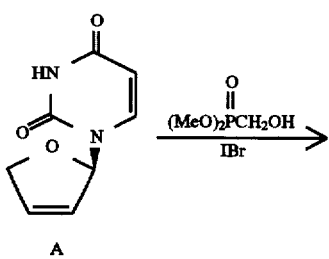

To a solution of the glycal A (1.0 g, 5.5 mmol) [prepared according to the literature procedure: Zemlicka, J.; Gasser, R.; Friesler, J. V.; Horwitz, J. P., J. Am. Chem. Soc. (1972) 94, 3213] and dimethyl (hydroxymethyl)phosphonate (7.8 g, 55 mmol) in $CH_2Cl_2$ (10 mL) at −78° C. was added a solution of iodine bromide (2.3 g, 11 mmol) in $CH_2Cl_2$ (10 mL over a period of 15 min. After being stirred at −78° C. for 90 min, the mixture was diluted with $CH_2Cl_2$ (50 mL) and aqueous $NaHCO_3$. The organic phase was washed with aqueous sodium bisulfite, dried over $MgSO_4$, and evaporated in vacuo. The residual oil was chromatographed on silica gel using $CH_2Cl_2$/5% MeOH as eluent to give the noted product B (1.3 g, 50%) as a colorless oil:

$^1$H-NMR (CDCl$_3$) δ2.5–2.7 (m, 2H), 3.7–4.05 (m, 8H), 4.29 (d, J=4.9 Hz, 1H), 5.33 (s, 1H), 5.77 (d, J=8.2 Hz, 1H), 6.73 (t, J=7.1 Hz, 1H), 7.56 (d, J=8.2 Hz, 1H), 9.83 (br s, 1H);

$^{13}$C-NMR (CDCl$_3$) δ20.21, 40.31, 53.68, 60.92 (d, J=172 Hz), 86.57, 104.56, 112.25 (d, J=13 Hz), 140.6, 151.28, 163.95.

B. To a solution of product B from part A (1.2 g, 2.7 mmol) in MeOH (5 mL) at 0° C. was added 25% sodium methoxide in MeOH (3 mL). After being stirred at 25° C. for 16 hr, the reaction mixture was neutralized to pH 8.0 by dropwise addition of 2N HCl in an ice bath. Volatiles were removed in vacuo to dryness and the residue was chromatographed on silica gel using $CH_2Cl_2$/7% MeOH as eluent to give the final product (500 mg, 62%) as a colorless oil:

$^1$H-NMR (CDCl$_3$) δ3.72 (d, J=6 Hz, 3H), 3.75 (d, J=5 Hz, 3H), 3.88 (dd, J=8.7, 13.8 Hz, 1H), 4.05 (dd, J=9.9, 13.8 Hz, 1H), 5.68 (d, J=8.1 Hz, 1H), 5.73 (s, 1H), 6.06 (d, J=5.4 Hz, 1H), 6.26 (d, J=5.4 Hz, 1H), 6.93 (s, 1H), 7.34 (d, J=8.1 Hz, 1H).

Anal. Calcd. for $C_{11}H_{15}N_2O_7P$: C, 41.51; H, 4.72; N, 8.81. Found: C, 41.91; H, 5.05; N, 8.42.

Example 58

(2R,5R)-1-[2,5-Dihydro-5-(dimethoxyphosphinyl)methoxy-2-furanyl]-5-chlorouracil

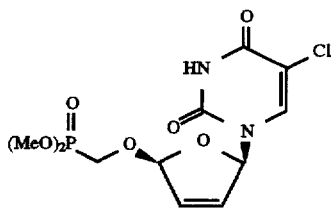

To a solution of the product of Example 57 (400 mg, 1.3 mmol) in pyridine (15 mL) was added N-chlorosuccinimide (200 mg, 1.5 mmol) and the solution was heated at 90°–95° C. for 30 min under nitrogen. All volatiles were removed in vacuo and the oily residue was chromatographed on silica gel using CH₂Cl₂/3% MeOH as eluent to give the product (390 mg, 87%) as a colorless oil:

¹H-NMR (CDCl₃) δ3.73 (d, J=6.9 Hz, 3H), 3.78 (d, J=6.9 Hz, 3H), 3.93 (dd, J=7.5, 13.8 Hz, 3H), 3.78 (d, J=6.9 Hz, 3H), 3.93 (dd, J=7.5, 13.8 Hz, 1H), 4.09 (dd, J=10.2, 13.8 Hz, 1H), 5.73 (s, 1H), 6.09 (d, J=6 Hz, 1H), 6.28 (d, J=6 Hz, 1H), 6.89 (s, 1H), 7.49 (s, 1H), 9.35 (br s, 1H).

Anal Calcd. for C₁₁H₁₄N₂O₇ClP: C, 37.45; H, 3.97; N, 7.94. Found: C, 37.15; H, 4.28; N, 7.59.

Example 59

(2R,5R)-1-[2,5-Dihydro-5-(phosphonomethoxy)-2-furanyl]-5-chlorouracil

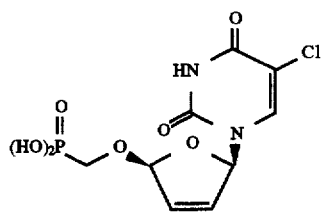

To a solution of the product of Example 58 (380 mg, 1.1 mmol) in DMF (3 mL) at 0° C. was added freshly distilled bromotrimethylsilane (2 mL). After the mixture was stirred at 25° C. for 2 hr, the volatiles were removed in vacuo and the residue was dissolved in concentrated NH₄OH (3 mL) and cooled in the ice bath. The white precipitate was collected by filtration and washed with water, and air dried to give the product (145 mg, 43%) as a white powder: m.p. 105°–106° C.; UV$_{max}$ (EtOH) 276 nm (ε8052);

¹H-NMR (DMSO-d₆) δ3.68 (dd, J=3.9, 13 Hz, 1H), 3.71 (dd, J=4.8, 13 Hz, 1H), 5.81 (s, 1H), 6.26 (d, J=6 Hz, 1H), 6.41 (d, J=6 Hz, 1H), 6.71 (s, 1H), 7.48 (s, 1H);

¹³C-NMR (DMSO-d₆) δ63.42 (d, J=162 Hz), 87.78, 108.21 (d, J=15 Hz), 108.36, 130.41, 132.28, 136.97, 149.63, 158.99.

Anal. Calcd. for C₉H₁₀N₂O₇ClP.H₂O: C, 31.55; H, 3.53; N, 8.12: Cl, 10.35. Found: C, 31.22; H, 3.52: N, 7.97; Cl, 9.81.

Example 60

(2R,4S,5R)-1-[[tetrahydro-4-(phenylselenyl)-5-[(dimethoxyphosphinyl)methoxy]-2-furanyl]5-iodouracil

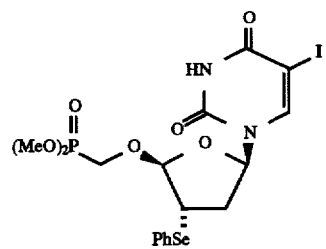

A. 2'-Deoxy-5-iodouridine-5'-carboxylic acid

The platinum-catalyzed oxidation of 2'-deoxy-5-iodouridine followed the literature procedure [Moss, G. P.; Reese, C. B.; Schofield, K.; Shapiro, R.; Todd, A. R., *J. Chem. Soc.* (1963), 1149] to give the product in 35% yield: m.p. >200° C. (dec.);

NMR (D₂O) δ2.2–2.4 (m, 2H), 4.57 (d, J=2.1 Hz, 1H), 6.36 (dd, J=6.3, 8.1 Hz, 1H), 8.68 (s, 1H), one proton at the D₂O (H₂O) region (4.7–4.9).

Anal. Calcd. for C₉H₉N₂O₆I.H₂O: C, 28.00; H, 2.87; N, 7.26. Found: C, 27.93; H, 2.74; N, 6.98.

B. A solution of the product of Part A (800 mg, 2.2 mmol) and dimethylformamide dineopentylacetal (4 mL) in DMF (30 mL) was heated for 6 hr at 110° C. under N₂. After cooling, the reaction mixture was evaporated in vacuo and the resulting residual oil was chromatographed on silica gel using CH₂Cl₂/5% MeOH as eluent to give the product (501 mg, 79%) as a white crystal: m.p. 182° C.;

NMR (CDCl₃) δ2.4–2.6 (m, 1H), 3.1–3.3 (m, 1H), 5.13 (dd, J=2.4,5.1 Hz, 1H), 6.45 (dd, J=2.4,4.8 Hz, 1H), 6.57 (dd, J=3.9,6.5 Hz, 1H), 7.57 (s, 1H), 8.31 (br s, 1H).

Anal. Calcd. for C₈H₇N₂O₃I: C, 31.40; H, 2.31; N, 9.16. Found: C, 31.61; H, 2.31; N, 8.98.

C. To a-solution of the glycal prepared in Part B (1.8 g, 6.1 mmol) and dimethyl(hydroxymethyl)phosphonate (8.3 g, 59 mmol) in 1,2-dichloroethane (20 mL) was added N-(phenylseleno)phthalimide (3.7 g, 12.2 mmol) and the solution was heated at 80° C. for 2 hr. After cooling, the reaction was diluted with CH₂Cl₂ (100 mL) and washed with water (10 mL×4) and brine, dried over MgSO₄, and concentrated in vacuo. The residual oil was chromatographed over silica gel using CH₂Cl₂/5% MeOH as eluent to give the product (2.2 g, 60%) as a colorless oil:

¹H-NMR (CDCl₃) δ2.4–25 (m, 2H), 3.75 (d, J=10.8 Hz, 6H), 3.78 (m, 1H), 3.88 (dd, J=4.2, 14.1 Hz, 1H), 3.94 (dd, J=8.5, 14.1 Hz, 1H), 5.17 (s, 1H), 6.37 (t, J=6.6 Hz, 1H), 7.3–7.6 (m, 5H), 7.86 (s, 1H), 9.35 (s, 1H).

Example 61

(2R,5R)-1-[[2,5-Dihydro-5-[dimethoxyphosphinyl)methoxy]-2-furanyl]-5-ioduracil

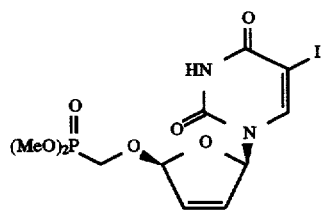

A solution of the product of Example 60 (440 mg, 0.73 mmol), NaHCO₃ (250 mg) and 30% H₂O₂ (0.3 mL) in 1,4-dioxane-water (2:1, 8 mL) was stirred at 25° C. for 4 hr. All volatiles were removed in vacuo and the residue was extracted with CH₂Cl₂ (30 mL). The CH₂Cl₂ was dried (MgSO₄) and evaporated in vacuo. The residual oil was chromatographed on silica gel using CH₂Cl₂/5% MeOH as eluent to give the product (233 mg, 70%) as a white crystal: m.p. 192° C. (dec.);

¹H-NMR (CDCl₃) δ3.58 (d, J=10.8 Hz, 1H), 3.62 (d, J=10.8 Hz, 1H), 3.83 (dd, J=9.6, 13.8 Hz, 1H), 3.983 (dd, J=9.3, 13.8 Hz, 1H), 5.58 (s, 1H), 6.01 (d, J=7.2 Hz, 1H), 6.19 (d, J=7.2 Hz, 1H), 6.24 (s, 1H), 7.50 (s, 1H).

Anal. Calcd. for C₁₁H₁₄N₂O₇PI: C, 29.75; H, 3.18; N, 6.31. Found: C, 29.79; H, 3.15; N, 5.99.

Example 62

(2R,5R)-1-[2,5-Dihydro-5-(phosphonomethoxy)-2-furanyl]-5-ioduracil monoammonium salt

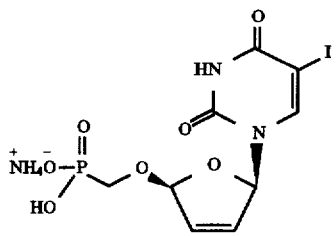

To a solution of the product of Example 61 (150 mg, 0.34 mmol) in dry DMF (4 mL) was added freshly distilled bromotrimethylsilane (2 mL). After the mixture was stirred at 0° C. for 2 hr, the volatiles were removed in vacuo and the residue was dissolved in concentrated NH$_4$OH (10 mL) and then evaporated in vacuo to dryness. The residual solid was purified by C$_{18}$ reverse-phase column chromatography under 8 psi of pressure using water as eluent to give the product (74 mg, 50%) as an amorphous powder: UV$_{max}$ (H$_2$O) 286 nm (ε8323); $^{13}$C-NMR (D$_2$O) δ67.38 (d, J=157 Hz), 90.90, 111.86 (d, J=11 Hz), 131.95, 135.59, 149.09, 154.33, 161.42, 165.78.

Anal. Calcd. for C$_9$H$_{13}$N$_3$O$_7$P LH$_2$O: C, 24.16; H, 3.32; N, 9.31. Found: C, 24.50; H, 2.99, N, 9.73.

Example 63

(2'R,5'R)-9-[2,5-Dihydro-5-(dimethoxyphosphinyl)methoxy-2-furanyl]adenine

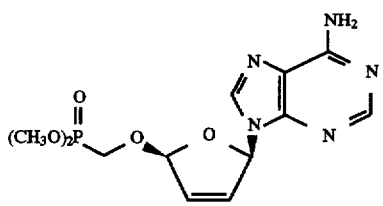

To a solution of the product of Example 48 or 52 (5.7 g, 13.3 mmol) in MeOH (50 mL) at 23° C. was added sodium methoxide (3.0 g, 65 mmol). After being stirred at 23° C. for 5 hr, the solution was cooled to 0° C. and the pH was adjusted to 7-8 by addition of 6N HCl. All volatiles were removed in vacuo and the residue was dissolved in CH$_2$Cl$_2$/3% MeOH and dried over MgSO$_4$ and then evaporated in vacuo to dryness. The residual oil was chromatographed on silica gel using CH$_2$Cl$_2$/5% MeOH as eluent to give the product (2.8 g, 80%) as a white solid: m.p. 146°-149° C.;

$^1$H-NMR (CDCl$_3$) δ3.70 (d, J=10.8 Hz, 3H), 3.76 (d, J=10.78 Hz, 3H), 3.86 (dd, J=8.7, 13.8 Hz), 4.03 (dd, J=9.9, 13.8 Hz, 1H), 5.85 (s, 1H), 5.91 (br s, 1H), 6.29 (d, J=5.7 Hz, 1H), 6.39 (d, J=5.7 Hz, 1H), 6.99 (s, 1H), 7.94 (s, 1H), 8.36 (s, 1H).

$^{13}$C-NMR (CDCl$_3$) δ61.49 (d, J=170 Hz), 86.29, 108.99, 109.16, 119.93, 131.04, 132.33, 139.56, 150.23, 154.07, 156.51.

Example 64

(2'R,5'R)-9-[2,5-Dihydro-5-(dimethoxyphosphinyl)methoxy-2-furanyl]adenine 1-N-oxide

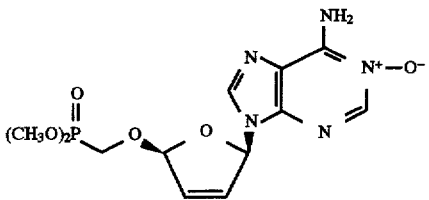

To a solution of the product of Example 63 (1.62 g, 4.75 mmol) in CH$_2$Cl$_2$ (50 mL) was added 80–85% 3-chloroperoxybenzoic acid (1.0 g, ca. 0.5 mmol) and the resulting yellow solution was stirred at 23° C. for 3 hr. After evaporation of CH$_2$Cl$_2$, the residue was triturated with ether/hexane (1:9, 100 mL) to obtain 1.68 g (98%) of the product as an amorphous powder:

UV$_{max}$ (EtOH) 236 nm (ε3976);

$^1$H-NMR (DMSO-d$_6$) δ3.58 (d, J=10.6 Hz, 3H), 3.62 (d, J=10.6 Hz, 3H), 3.95 (d, J=9.5 Hz, 2H), 4.1 (br s, 2H), 5.95 (s, 1H) 6.48 (d, J=5.9 Hz, 1H), 6.61 (d, J=5.9 Hz, 1H), 6.84 (s, 1H), 8.11 (s, 1H), 8.68 (s, 1H);

$^{13}$C-NMR (DMSO-d$_6$) 53.45 (d, J=6.5 Hz), 61.68 (d, J=171 Hz), 86.34, 109.25, 119.30, 130.92, 132.50, 142.26, 142.95, 145.21, 149.41.

Anal. Calcd. for C$_{12}$H$_{15}$N$_5$O$_6$P·H$_2$O: C, 38.29; H, 3.9: N, 18.61. Found: C, 38.43; H, 4.04; N, 18.89.

Example 65

(2'R,5'R)-2,6-Diamino-9-[2,5-dihydro-5-(dimethoxyphosphinyl)methoxy-2-furanyl]purine

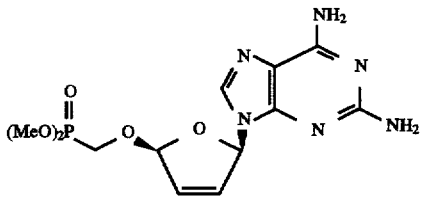

A. 2-Imino-7-(2R,5R)-2,5-dihydro-5-(dimethoxyphosphinyl)methoxy-2-furanyl]-[1,2,4-oxadiazolo-(3,2-i)purine]hydrobromide

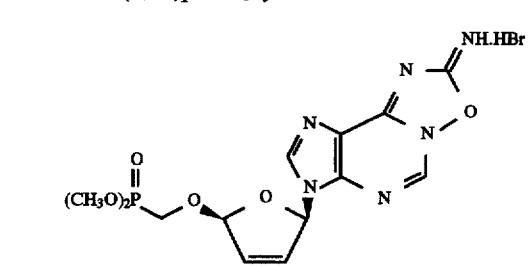

To a solution of the product of Example 64 (1.62 g, 4.53 mmol) in MeOH was added cyanogen bromide (530 mg, 5.0 mmol). After 2 hr at 23° C., the MeOH was evaporated in vacuo to give a colorless oil, which was triturated with ether/hexane (1:9) to give the product (1.89 g, 90%) as an amorphous powder: UV$_{max}$ (EtOH) 222 nm (ε15325), 282 nm (ε11682);

$^1$H-NMR (CH$_3$OD) δ3.47 (d, J=10.8 Hz, 3H), 3.52 (d, J=10.8 Hz, 3H), 3.82 (d, J=9.6 Hz, 2H), 5.75 (s, 1H) 6.35 (s, 2H), 6.93 (s, 1H), 8.34 (s, 1H), 9.54 (s, 1H).

Anal. Calcd. for C$_{13}$H$_{16}$N$_6$O$_6$PBr: C, 33.69; H, 3.45; N, 18.14. Found: C, 33.29; H, 3.64: N, 17.90.

47

B. (2'R,5'R) -2-Amino-6-methoxy-9-[2,5-dihydro-5-dimethoxyphosphinyl)methoxy-2-furanyl]adenine

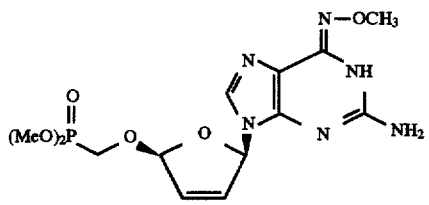

To a solution of the product of part A (3.2 g, 6.9 mmol) in DMF (50 mL) at 23° C. was added TEA (1.5 mL) followed by iodomethane (2 mL) followed by iodomethane (2 mL). After being stirred for 5 hr, all volatiles were removed in vacuo. The resulting oil was chromatographed on silica gel using $CH_2Cl_2$/7% MeOH as eluent to give the intermediate product (2.1 g, 81%) as a slightly yellow oil:

$^1$H-NMR (CD$_3$OD) δ3.58 (d, J=10.7 Hz, 3H), 3.62 (d, J=10.7 Hz, 3H), 3.85 (dd, J=9.2, 13.9 Hz, 1H), 3.88 (dd, J=9.2, 13.9 Hz, 1H), 3.88 (dd, J=9.2, 13.9 Hz, 1H), 4.07 (s, 3H), 5.81 (s, 1H), 6.38 (d, J=4.8 Hz, 1H), 6.42 (d, J=4.8 Hz, 1H), 6.80 (s, 1H), 7.95 (s, 1H), 8.59 (s, 1H);

IR Film (cm$^{-1}$) 2180, 1630.

A solution of the intermediate (1.3 g, 3.3 mmol) in 0.05N NaOH (80 mL) was stirred at 23° C. for 45 min The pH of the solution was adjusted to 7.5 with 1N HCl and the resulting solution was heated at 70°–75° C. for 2 hr. After cooling, all volatiles were removed in vacuo. The crude residue was chromatographed on silica gel using $CH_2Cl_2$/10% MeOH as eluent to give the product (70 mg, 56%) as a colorless oil: UV$_{max}$ (EtOH) 214 nm (ε13471), 280 nm (ε11927);

$^1$H-NMR (CD$_3$OD) δ3.60 (d, J=11.1 Hz, 3H), 3.65 (d, J=11.1 Hz, 3H), 3.79 (dd, J=9.2, 13.5 Hz, 1H), 3.94 (dd, J=11.0, 13.5 Hz, 1H), 5.72 (s, 1H), 6.23 (s, 2H) 6.63 (s, 1H) 7.41 (s, 1H).

Anal. Calcd. for $C_{13}H_{19}N_6O_6P$: C, 40.41; H, 4.92; N, 21.76. Found: C, 39.98; H, 4.86; N, 21.69.

C. To a solution of the product of part B (1.5 g, 3.8 mmol) in tetrahydrofuran-water (9:1, 150 mL) at 23° C. was added 2.1 g of Al—Hg strips (5 mm×40 mm, prepared from aluminum foil and 2% HgCl$_2$). After being stirred at 23° C. for 30 min, the mixture was heated at 70° C. for 60 min. The mixture was filtered through a pad of Celite and washed with tetrahydrofuran. The combined solvents were removed in vacuo. The residual oil was chromatographed on silica gel using $CH_2Cl_2$/10% MeOH as eluent to give the final product (540 mg, 40%) as a colorless oil:

$^1$H-NMR (CD$_3$OD) δ3.43 (d, J=10.5 Hz, 3H), 3.49 (d, J=10.8 Hz, 3H), 3.73 (dd, J=10.2, 12.3 Hz, 1H), 3.83 (dd, J=10.2, 12.3 Hz, 1H), 5.63 (s, 1H) 6.19 (d, J=6 Hz, 1H), 6.21 (d, J=6 Hz, 1H), 6.53 (s, 1H), 7.45 (s, 1H):

$^{13}$C-NMR (CD$_3$OD) δ53.87 (d, J=25 Hz), 60.93 (d, J=163 Hz), 87.14, 110.28, 114.10, 132.85, 133.20, 136.87, 152.59, 157.63, 162.09.

Anal. Calcd. for $C_{12}H_{17}N_6O_5P$: C, 40.49; H, 4.82; N, 23.59. Found: C, 40.07; H, 4.63; N, 23.86.

Example 66

(2'R,5'R)-2,6-Diamino-9-(2,5-dihydro-5-phosphonomethoxy-2-furanyl)purine

48

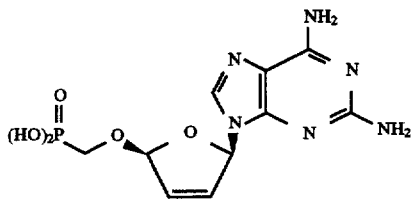

To a solution of the product of Example 65, (380 mg, 1.07 mmol) in DMF (4 mL) at 0° C. was added 2,6-lutidine (400 mg, 3.7 mmol) and freshly distilled bromotrimethylsilane (2 mL). After being stirred at 23° C. for 18 hr, all volatiles were removed in vacuo and the pH was adjusted to 11.0 by addition of ice cooled 10% NH$_4$OH. After evaporation of water, the residue was purified by C$_{18}$ reverse-phase column chromatography using water as eluent under 8 psi pressure to give the product (275 mg, 55%) as a white powder: m.p. 146°–152° C.; UV$_{max}$ (H$_2$O) 256 nm (ε8406), 280 nm (ε9044);

$^1$H-NMR (D$_2$O) δ3.34 (dd, J=8.9, 21.5 Hz, 1H), 3.52 (dd, J=10.5, 21.5 Hz, 1H), 5.98 (s, 1H), 6.35 (d, J=6 Hz, 1H), 6.42 (d, J=6Hz, 1H), 6.63 (s, 1H), 7.82 (s, 1H);

$^{13}$C-NMR (D$_2$O) δ68.05 (d, J=149 Hz), 88.01, 112.20 (d, J=10.6 Hz), 115.69, 131.47, 135.57, 140.63, 153.51, 156.67, 161.09.

Example 67

(2R,5R)-1-[2,5-Dihydro-5-(phosphonomethoxy)-2-furanyl] uracil ammonium salt

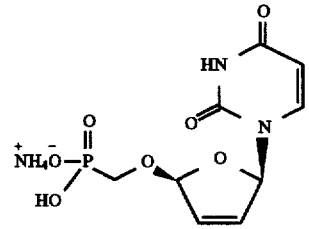

To a solution of the product of Example 57 (500 mg, 1.65 mmol) in DMF (3 mL) at 0° C. was added freshly distilled bromotrimethylsilane (3 mL). After being stirred at 0° C. for 2 hr, the volatiles were removed in vacuo and the residue was dissolved in concentrated NH$_4$OH (5 mL) and re-evaporated in vacuo. The residual oil was purified by C$_{18}$ reverse-phase column under 8 psi of pressure using water as eluent to give the product (300 mg, 56%) as a white amorphous solid: m.p. 140° C. (dec.); UV$_{max}$ (H$_2$O) 262 nm (ε9097);

$^1$H-NMR (D$_2$O) δ3.55 (dd, J=9.3, 12.6 Hz, 1H), 3.71 (dd, J=9.3, 12.6 Hz, 1H), 5.79 (d, J=8.1 Hz, 1H), 5.86 (s, 1H), 6.15 (d, J=6.0 Hz, 1H), 6.36 (d, J=6.0 Hz, 1H), 6.76 (s, 1H), 7.57 (d, J=8.1 Hz, 1H).

$^{13}$C-NMR (D$_2$O) 72.38 (d, J=155 Hz), 94.92, 109.62, 116.25 (d, J=12 Hz), 136.22, 139.74, 149.46, 158.97, 173.49.

Example 68

(2R,5R)-1-[2,3,4,5-Tetrahydro-5-(phosphonomethoxy)-2-furanyl]uracil ammonium salt

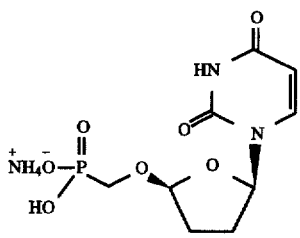

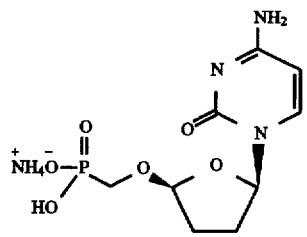

A solution of the product of Example 67 (100 mg, 0.3 mmol) in EtOH-water (4:1) (10 mL) was hydrogenated in the presence of 10% Pd/C (100 mg) at 5 psi for 2 hr. The mixture was filtered through Celite, and the filtrate was concentrated in vacuo. The residue was purified by $C_{18}$ reverse-phase column under 8 psi of pressure using water as eluent to give the product (65 mg, 63%) as a white solid: m.p. 134° C.; $UV_{max}$ ($H_2O$) 261 nm (ε9115);

$^1$H-NMR ($D_2O$) δ2.1–2.4 (m, 4H), 3.56 (dd, J=9.6, 13.0 Hz, 1H), 3.76 (dd, J=9.9, 13.0 Hz, 1H), 5.26 (d, J=3.0 Hz, 1H), 5.89 (d, J=8.3 Hz, 1H), 6.34 (t, J=6.6 Hz, 1H), 7.88 (d, J=8.3 Hz, 1H);

$^{13}$C-NMR ($D_2O$) δ35.30, 38.08, 70.72 (d, J=159 Hz), 93.56, 109.78, 113.43 (d,J=12 Hz), 149.72, 159.15, 173.50.

Anal. Calcd. for $C_9H_{16}N_3O_7P\cdot2H_2O$: C, 31.32; H, 5.84; N, 12.17. Found: C, 31.59; H, 5.60; N, 11.96.

Example 69

(2R,5R)-1-[2,5-dihydro-5-(phosphonomethoxy)-2-furanyl]cytosine ammonium salt

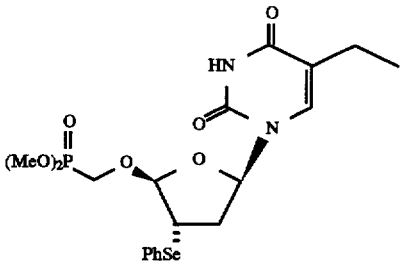

To a solution of the product of Example 57 (550 mg, 17.3 mmol) in pyridine (16 mL) was added 2-chlorophenyl dichlorophosphate (0.8 mL, 4.8 mmol) and 1,2,4-triazole (760 mg, 11 mmol). After being stirred at 23° C. for 15 hr, concentrated ammonium hydroxide (3 mL) was added to the reaction mixture and the resulting yellow solution was kept at 23° C. for 2 hr. All volatiles were removed in vacuo and the residual mixture was passed through a silica gel pad using $CH_2Cl_2$/10% MeOH as eluent. The filtrate was evaporated in vacuo and the residual oil was dissolved in DMF (4 mL). To this solution, freshly distilled bromotrimethylsilane (4 mL) was added at 0° C. After being stirred at 0° C. for 2 hr, all volatiles were removed in vacuo and the residual oil was purified by $C_{18}$ reverse-phase column under 8 psi of pressure using water/10% MeOH as eluent to give the product (130 mg, 24%) as a white powder. $UV_{max}$ ($H_2O$) 270 nm (ε6268);

$^1$H-NMR ($D_2O$) δ3.72 (dd, J=9.3, 12.3 Hz, 1H), 3.84 (dd, J=9.3, 13.2 Hz, 1H), 5.89 (s, 1H), 6.17 (d, J=7.8 Hz, 1H), 6.22 (d, J=6 Hz, 1H), 6.41 (d, J=6 Hz, 1H), 6.83 (s, 1H), 7.80 (d, J=7.8 Hz, 1H).

Anal. Calcd. for $C_9H_{15}N_4O_6P\cdot H_2O$: C, 33.24; H, 4.96; N, 12.92. Found: C, 32.95; H, 4.61; N, 13.20.

Example 70

(2R,5R)-1-[2,3,4,5-tetrahydro-5-(phosphonomethoxy)-2-furanyl]cytosine ammonium salt A solution of the product from Example 69 (100 mg, 0.33 mmol) in water-EtOH (1:4) (10 mL) was hydrogenated in the presence of Pd/C (100 mg) at 5 psi for 2 hr. The mixture was filtered through Celite, and the filtrate was concentrated in vacuo. The residual oil was purified on a $C_{18}$ reverse phase column under 8 psi of pressure using water as eluent to give the product (20 mg, 20%) as a white powder: $UV_{max}$ ($H_2O$) 272 nm (ε7200);

$^1$H-NMR ($D_2O$) δ2.1–2.5 (m, 4H), 3.54 (dd, J=9.9, 12.9 Hz, 1H), 3.77 (dd, J=9.0, 12.9 Hz, 1H), 5.29 (d, J=3.0 Hz, 1H), 6.09 (d, J=7.5 Hz, 1H), 6.35 (t, J=6.6 Hz, 1H), 7.91 (d, J=7.5 Hz, 1H);

$^{13}$C-NMR ($D_2O$) δ35.98, 37.97, 71.05, (d, J=158 Hz), 94.36, 103.77, 113.70 (d, J=13 Hz), 143.68, 149.52, 164.87, 173.11.

Example 71

(2R,4S,5R)-1-[Tetrahydro-4-phenylselenyl)-5-(dimethoxyphosphinyl)methoxy-2-furanyl]-5-ethyluracil A. 2'-Deoxy-5-ethyluridine-5'-carboxylic acid The platinum-catalyzed oxidation of 2'-deoxy-5-ethyluridine was accomplished by following the literature procedure (Moss, G. P.; Reese, C. B.; Schofield, K.; Shapiro, R.; Todd, A. R., *J. Chem. Soc.* (1963) 1149) to give the noted product in 75% yield as an amorphous powder:

$^1$H-NMR ($D_2O$) δ1.07 (t, J=7.5 Hz, 3H), 2.2–2.5 (m, 4H), 4.68 (s, 1H), 6.43 (t, J=7.5 Hz, 1H), 7.92 (s, 1H).

Anal. Calcd. for $C_{11}H_{14}N_2O_6$: C, 48.90; H, 5.23; N, 10.37. Found: C, 48.70; H, 5.22; N, 10.02.

B. A solution of the product of part A (7.9 g, 29 mmol) and dimethylformamide dineopentylacetal (32 mL) in DMF (100 mL) was heated at 110° C. for 6 hr. After cooling, the reaction mixture was evaporated in vacuo. The resulting residual oil was chromatographed on silica gel using $CH_2Cl_2$/5% MeOH as eluent to give the intermediate product (5.3 g, 86%) as a white amorphous powder.

$^1$H-NMR ($CDCl_3$) δ1.08 (t, J=7.5 Hz, 3H), 2.28 (q, J=7.5 Hz, 2H), 2.5–2.65 (m, 1H), 3.1–3.2 (m, 1H), 5.11 (dd, J=2.7, 5.4 Hz, 1H), 6.45 (dd, J=2.7, 4.8 Hz, 1H), 6.68 (dd, J=4.5, 10.8 Hz, 1H), 6.96 (s, 1H), 8.39 (br s, 1H).

Anal. Calcd. for $C_{10}H_{12}N_2O_3$: C, 57.69; H, 5.81; N, 13.46. Found: C, 57.67; H, 5.79; N, 13.33.

C. To a solution of the glycal product of Step B (2.0 g, 9.6 mmol) and dimethyl (hydroxymethyl) phosphonate (9.4 g, 70 mmol) in CH$_2$Cl$_2$ (20 mL) at 23° C. was added N-(phenylseleno)phthalimide (6.1 g, 20 mmol) and the mixture was heated at 85° C. for 2 hr. After cooling, the reaction was diluted with CH$_2$Cl$_2$ (300 mL) washed with water and brine, dried over MgSO$_4$, and concentrated in vacuo. The residual oil was chromatographed on silica gel using CH$_2$Cl$_2$/5% MeOH as eluent to give the final product (3.5 g, 72%) as a hard oil:

$^1$H-NMR (CDCl$_3$) 1.08 (t, J=7.4 Hz, 3H), 2.3–2.5 (m, 3H), 3.75 (d, J=10.8 Hz, 6H), 3.7–3.9 (m, 3H), 5.13 (s, 1H), 6.53 (t, J=7.1 Hz, 1H), 7.2–7.6 (m, 5H).

Anal. Calcd. for C$_{19}$H$_{25}$O$_7$PSe.H$_2$O: C, 43.73; H, 5.18; N, 5.37. Found: C, 43.29; H, 5.30; N, 5.02.

Example 72

(2R,5R) -1-[2-5-Dihydro-5-(dimethylphosphinyl)methoxy-2-furanyl]-5-ethyluracil

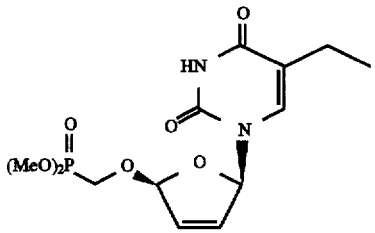

A solution of the product of Example 71 (3.5 g, 6.9 mmol), NaHCO$_3$ (2.3 g, 27 mmol) and 30% H$_2$O$_2$ (2.9 mL) in 1,4-dioxane-water (2:1, 50 mL) was stirred at 23° C. for 2 hr. All volatiles were removed in vacuo and the residue was extracted with CH$_2$Cl$_2$ (100 mL). The CH$_2$Cl$_2$ was evaporated to dryness, and the residual oil was chromatographed on silica gel using CH$_2$Cl$_2$/5% MeOH as eluent to give the product (1.8 g, 75%) as a colorless oil;

$^1$H-NMR (CDCl$_3$) δ0.87 (t, J=7.5 Hz, 3H), 2.05 (q, J=7.5 Hz, 2H), 3.52 (d, J=10.8 Hz, 3H), 3.56 (d, J=10.8 Hz, 3H), 3.87 (dd, J=9.3, 12.3 Hz, 1H), 3.95 (dd, J=9.3, 12.3 Hz, 1H), 5.58 (s, 1H), 6.0 (d, J=4.5 Hz, 1H), 6.14 (d, J=4.5 Hz, 1H), 6.67 (s, 1H), 6.98 (s, 1H).

Anal. Calcd. for C$_{13}$H$_{19}$N$_2$OP: C, 45.10; H, 5.54; N, 8.10. Found: C, 45.14; H, 5.50; N, 7.96.

Example 73

(2R, 5R)-1-[2,5-Dihydro-5-(phosphonomethoxy)-2-furanyl]-5-ethyluracil ammonium salt

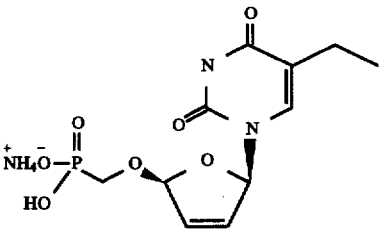

To a solution of the product of Example 72 (300 mg, 0.87 mmol) in DMF (8 mL) at 0° C. was added freshly distilled bromotrimethylsilane (3 mL). After being stirred at 0° C. for 2 hr, the volatiles were removed in vacuo to dryness. The residue was dissolved in concentrated NH$_4$OH (3 mL) and then evaporated in vacuo to dryness. The residue was purified by C$_{18}$ reverse phase column under 8 psi of pressure using water as eluent to give the product (146 mg, 50%) as a white powder: UV$_{max}$ (H$_2$O) 266 nm (ε8710);

$^1$H-NMR (D$_2$O) δ1.02 (t, J=7.4 Hz, 3H), 2.24 (q, J=7.4 Hz, 2H), 3.69 (dd, J=9.3, 12.8 Hz, 1H), 5.89 (s, 1H), 6.19 (d, J=7.2 Hz, 1H), 6.38 (d, J=7.2 Hz, 1H), 6.83 (s, 1H) 7.31 (s, 1H);

$^{13}$C-NMR (D$_2$O) δ18.78, 26.19, 71.52 (d, J=157 Hz), 94.82, 116.09 (d, J=11 Hz), 124.42, 136.48, 139.53, 143.98, 158.93, 173.24.

Anal. Calcd. for C$_{11}$H$_{18}$N$_3$O$_7$P.H$_2$O: C, 37.04; H, 5.71; N, 11.90. Found: C, 37.27, H, 5.49, N, 11.57.

Example 74

(2R,5R)-1-[2,5-Dihydro-5-(phosphonomethoxy)-2-furanyl-5-ethylcytosine ammonium salt

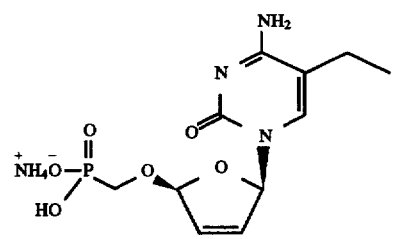

The product was prepared in 50% yield in a manner analogous to that described in Example 69 except the product of Example 72 was used as the starting material. The product was obtained as a white amorphous powder with the following spectral characteristics: UV$_{max}$ (H$_2$O) 276 nm (ε7425);

$^1$H-NMR (D$_2$O) δ1.04 (t, J=7.5 Hz, 3H), 2.26 (q, J=7.5 Hz, 2H), 3.55 (dd, J=8.3, 12.9 Hz, 1H), 3.62 (dd, J=8.4, 12.9 Hz, 1H), 5.96 (s, 1H), 6.14 (d, J=6.1 Hz, 1H), 6.35 (d, J=6.1 Hz, 1H), 6.78 (s, 1H) 7.31 (s, 1H);

$^{13}$C-NMR (D$_2$O) δ18.17, 26.47, 72.55 (d, J=155 Hz), 95.83, 116.15 (d, J=12 Hz), 117.71, 137.03, 139.07, 145.11, 164.62, 172.69.

Anal. Calcd. for C$_{11}$H$_{19}$N$_4$O$_6$P.H$_2$O: C, 35.48; H, 6.16: N, 16.42. Found: C, 35.79; H, 6.36; N, 16.58.

Example 75

(2R,5R)-1-[2,5-Dihydro-5-(phosphonomethoxy)-2-furanyl]-5-iodocytosine

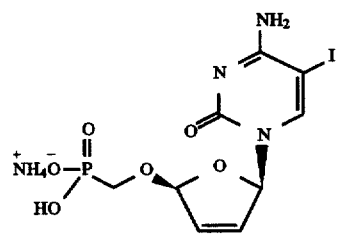

The product was prepared in 25% yield in a manner analogous to that described in Example 69 except that the product of Example 61 was used as the starting material. The product was obtained as a white amorphous powder having the following spectral characteristics:

UV$_{max}$ (H$_2$O) 286 nm (ε8350); NMR (D$_2$O) δ3.65 (dd, J=9.3, 11.1 Hz, 1H), 3.81 (dd, J=8.9, 11.1 Hz, 1H), 5.87 (s, 1H), 6.18 (d, J=5.9 Hz, 1H), 6.38 (d, J=5.9 Hz, 1H), 6.76 (s, 1H), 7.82 (s, 1H), 8.29 (br s, 1H).

Anal. Calcd. for C$_9$H$_{14}$N$_4$O$_6$PI.2H$_2$O: C, 23.09; H, 3.85; N, 11.96. Found: C, 22.85; H, 3.99; N, 11.69.

Example 76

(2R, 5R)-1-[2,5-Dihydro-5-(dimethoxyphosphinyl)methoxy-2-furanyl]-5-vinyl uracil

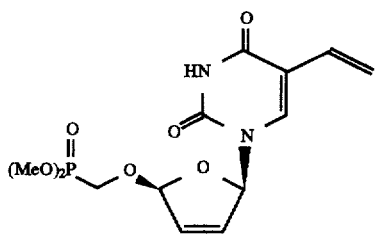

To a solution of the product of Example 61 (260 mg, 0.59 mmol) in N-methylpyrrolidinone (2 mL) at 23° C. was added tri-(2-furyl)phosphine (5.4 mg) and tris(dibenzylideneacetone)dipalladium (5.4 mg). After being stirred for 15 min, vinyltributyltin (200 mg) was added and the mixture was stirred at 23° C. for 30 hr. All volatiles were removed in vacuo and the residual oil was chromatographed on silica gel using $CH_2Cl_2$/5% MeOH as eluent to give the product (120 mg, 60%) as a colorless oil:

$^1$H-NMR (CDCl$_3$) δ3.49 (d, J=6.9 Hz, 3H), 3.54 (d, J=6.9 Hz, 3H), 3.83 (dd, J=8.7, 13.2 Hz, 1H), 3.93 (dd, J=8.9, 13.2 Hz, 1H), 4.95 (dd, J=1.5, 11 Hz, 1H), 5.68 (s, 1H), 5.75 (dd, J=1.5, 15.1 Hz, 1H), 6.12 (d, J=6.0 Hz, 1H), 6.16 (d, J=6.0 Hz, 1H), 6.19 (dd, J=11, 15.1 Hz, 1H), 6.70 (s, 1H), 7.24 (s, 1H).

Anal. Calcd. for $C_{13}H_{17}O_7P \cdot H_2O$: C, 44.20; H, 5.14; N, 7.94. Found: C, 43.91; H, 5.01: N, 7.68.

Example 77

(2R, 5R)-1-[2,5-Dihydro-5-(phosphonomethoxy)-2-furanyl]-5-vinyluracil ammonium salt

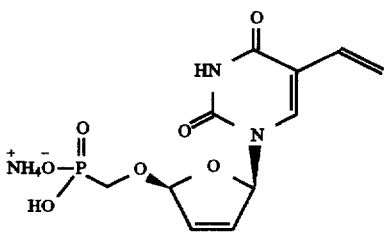

To a solution of the product of Example 76 (100 mg, 0.32 mmol) in DMF (4 mL) at 0° C. was added freshly distilled bromotrimethylsilane (2 mL). After being stirred at 23° C. for 2 hr, all volatiles were removed in vacuo. The residue was dissolved in concentrated NH$_4$OH (5 mL) and then evaporated to dryness. The residual solid was purified by C$_{18}$ reverse phase column chromatography under 8 psi of pressure using water as eluent to give the product (45 mg, 42%) as a white solid: m.p. 132° C. (dec.); UV$_{max}$ (H$_2$O) 284 nm (ϵ7016);

$^1$H-NMR (D$_2$O) δ3.64 (dd, J=9.5, 13.2 Hz, 1H), 6.19 (d, J=6.0 Hz, 1H), 6.37 (d, 1H), 5.88 (s, 1H), 6.19 (d, J=6.0 Hz, 1H), 6.37 (d, J=6.0 Hz, 1H), 6.39 (dd, J=11.4, 15.2 Hz, 1H), 6.85 (s, 1H), 7.59 (s, 1H).

Anal. Calcd. for $C_{11}H_{16}N_3O_7P \cdot H_2O$: C, 37.61; H, 5.12: N, 11.96. Found: C, 37.35; H, 4.95; N, 11.69.

Example 78

9-[2,3-Dideoxy-2,3-dihydro-4-β-phosphonomethoxy-β-D-erythrofuranosyl]adenine disodium salt The following is a preferred method for the large scale preparation of the corresponding disodium salt of the compound of Example 50:

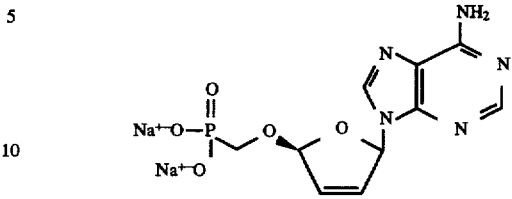

A. [2S-(2-a,3-b,5-a)]-5-(6-Amino-9H-purin-9-yl)tetrahydro-3-hydroxy-2-furancarboxylic acid To a 12 liter reaction flask was added water (6 liters) and potassium hydroxide (240 g of 85% (by assay) potassium hydroxide, 3.6 mole, 3 equiv). The solution reached an internal temperature of 35° C., and 2'-desoxyadenosine (300 g, 1.2 moles, Cruachem Ltd., Glasgow, Scotland, UK) was added in one portion. The 2-desoxy-adenosine dissolved in about 15 min. The reaction mixture was cooled to 10°–15° C. and potassium permanganate (750 g, 4.7 mole, 4 equivs.) was added portionwise, over 2–2.5 hr. The solution became a dark brown suspension.

After the addition was complete, the reaction was stirred for 1 hr, then checked by TLC (ethyl acetate:methanol:acetic acid (20:4:4), R$_f$ (product) 0.3) which showed no starting material remained. Excess permanganate was quenched by the dropwise addition to the suspension of 30% hydrogen peroxide. The reaction mixture was then filtered through a bed of Celite, and the filtrate concentrated to about 1.5 liters in volume. This solution was then cooled to 10° C., and the pH slowly lowered stepwise from 13.8 to 8.0 by the dropwise addition of concentrated hydrochloric acid. The mixture was filtered, the filtrate was recooled and the pH was lowered slowly from 8.0 to 4.2 as before. The product precipitated, and was collected by filtration and washed with water, then dried in vacuo overnight. After the above procedure was repeated six times, approximately 500 g of the product were obtained which after isolation and drying was about a 22% yield.

B. (R)-9-(2,3-Dihydro-2-furanyl)-N-[(dimethylamino)methyl]-9H-purin-6-amine

A suspension of the product of Part A (250 g, 0.94 mole) in dry dimethylformamide (1 liter) was heated to 120° C. To the suspension was added dimethylformamide dineopentylacetal (920 mL, 764 g, 3.3 mole, 3.5 equiv.) in a steady stream over 1 hr. The reaction was maintained at a temperature of 120° C. Heating at 120° C. was continued for 9 hr, then the reaction mixture was allowed to cool to 20°–25° C. Analysis by TLC (methylene chloride:methanol (90:10), R$_f$ (product) 0.6) indicated that the reaction was complete.

The reaction mixture was filtered, removing approximately 60 grams of an insoluble solid by-product. The filtrate was concentrated under high vacuum to a brown oil, which separated into 2 phases. The lower phase was drawn off and stored at 0°–5° C.

A second identical run of the above procedure was performed, and the crude products were combined. The product was partially crystallized, and was collected by filtration and washed with diethyl ether. Approximately 170 grams of product were obtained. The filtrate and diethyl ether washings were combined and reconcentrated, and the residue chromatographed in several runs using methylene chloride:methanol (97:3) as eluent at a flow rate of approximately 100 mL/min (20 psi). Product-containing fractions were combined and concentrated in vacuo. The residue was triturated with diethyl ether, and the product combined with the product isolated above. Approximately 313 g of the desired product (68% yield) were isolated.

C. (R)-9-(2,3-Dihydro-2-furanyl)-9H-purin-6-amine

To a suspension of the product of Step B (164 g, 0.65 mole) in methanol (400 mL) was added, in a steady stream over approximately 30 min, 30% ammonium hydroxide (400 mL). The reaction mixture became endothermic, with the internal temperature dropping to 16° C. A clear light orange colored solution was obtained after approximately 50% of the ammonium hydroxide had been added. The reaction mixture was stirred for 16 hr, becoming a white suspension. Analysis by TLC (methylene chloride:methanol (90:10), $R_f$ (product) 0.5) indicated the reaction was complete. The reaction mixture was cooled to 0°–5° C., and the product was collected by filtration, washed with water (100 mL) then twice suspended in toluene and concentrated to dryness.

A second run on 103 g of the product of Step B was performed. The products of both runs were combined, weighing 196 g for a 90% yield.

D. (R)-N-[9-(2,3-Dihydro-2-furanyl)-9H-purin-6-yl]-2,2-dimethyl]propanamide

To a suspension of the product of Step C (196 g, 0.97 mole), 4-dimethylaminopyridine (5.9 g, 0.048 mole) in dry pyridine (970 mL) at 26° C. was added dropwise over 1 hr trimethylacetylchloride (145 mL, 142.1 g, 1.18 mole, 1.2 equiv.). A slight 3° C. exotherm was noted. The reaction mixture was then heated to 55° C. for 4 hr becoming a pale yellow-orange solution. Analysis by TLC (methylene chloride: methanol (90:10), $R_f$ (product) 0.75) showed the reaction was complete. The reaction solution was cooled to 25° C. and methanol (40 mL) was slowly added. The reaction solution was then stirred for 30 min, then concentrated in vacuo to a thick orange syrup. The residue was dissolved in methylene chloride (1.5 liters) and washed with 0.5N sodium bisulfate (3×500 mL), 1N sodium bisulfate (2×500 mL), then brine (1×500 mL). All aqueous washes were combined and extracted with methylene chloride (1×500 mL). All methylene chloride extracts were combined and dried over anhydrous sodium sulfate, then filtered and concentrated in vacuo to a light orange oil. The oil was suspended in toluene (200 mL) and concentrated in vacuo. The product solidified to a pale yellow solid weighing 262 g for a yield of 94%.

E. (Hydroxymethyl)phosphonic acid, dimethyl ester

To a suspension of paraformaldehyde (173 g, 5.76 mole, 1.3 equiv.) in tetrahydrofuran (1200 mL) was added triethylamine (65 mL, 47.2 g, 0.47 mole, 0.1 equiv.). The mixture was stirred and heated to 65° C., and dimethylphosphite (500 g, 4.54 mole) was added dropwise at a rate to maintain the temperature between 65° C. and 70° C. The addition was completed in approximately 50 min. The reaction mixture was maintained at 70° C. for 2 hr, then allowed to cool to 25° C., standing overnight.

The reaction mixture was filtered through Celite, then concentrated in vacuo to a cloudy, colorless oil, weighing approximately 600 g. The oil was triturated with diethyl ether (4×500 mL), and toluene (3×1 liter). The crude product then was dissolved in methylene chloride and applied to a silica gel (3 Kg) column. The product was eluted with methylene chloride:methanol (97:3). After approximately 12 liters of eluent had been collected, the desired product was detected by TLC (methylene chloride: isopropanol (90:10), $R_f$ (product) 0.4–0.5, visualized with alkaline potassium permaganate spray). Product containing fractions were combined and concentrated to a colorless oil weighing approximately 340 g for a 52% yield.

F. [2S-(2-a,3-b,5-a)]-[[[5-[6-[2,2-Dimethyl-1-oxopropyl)amino]-9H-purin-9-yl]-2,5-dihydro-3-iodo-2-furanyl]oxy]methyl]phosphonic acid, dimethyl ester A solution of the products of Step D (48 g, 0.167 mole) and Step E (233 g, 1.67 mole, 10 equiv.) in methylene chloride (500 mL) was cooled to –75° C. At least a 10-fold excess of the product of Step E to the product of Step D is preferred for obtaining maximum yields. To this solution was added iodine monobromide (1M in methylene chloride, 320 mL, 2 equiv.) over approx 15 min. A 7° C. exotherm (–75° C. to –67° C.) was noted, but subsided when approximately 50% of the iodine monobromide was added. The reaction mixture was brought to –25° C., over 1 hr, and held at this temperature for 4 hr, then checked by TLC (methylene chloride: methanol (95:5), $R_f$ 0.6 for the product), and stirred an additional 2 hr at –25° C.

The reaction mixture was slowly added to a biphasic mixture of methylene chloride (1000 mL), saturated sodium bicarbonate (1000 mL), and aqueous 10% sodium bisulfite (250 mL). The methylene chloride layer was washed with a 10:3 mixture of saturated sodium bicarbonate and 10% sodium bisulfite (2×300 mL) and brine (1×300 mL). Excess iodine monobromide is quenched by addition of further sodium bisulfite, if needed, and solid sodium bicarbonate is added, as necessary to maintain the pH above 7. The methylene chloride layer was dried over sodium sulfate, then concentrated in vacuo to give a yellow foam weighing 88 g.

The above procedure was repeated on 2×43 portions of the compound of Step D. The combined crude product (approximately 250 g) was dissolved in methylene chloride:ethanol (96:4) and chromatographed in 2 runs on silica gel columns (3.5 Kg) under 20 psi pressure at a flow rate of approximately 150 mL/min. Product-containing fractions were combined and concentrated to give a yellow foam weighing 144 g over both runs for a combined yield of 55%.

G. (2S-cis)-[[[5-(6-Amino-9H-purin-9-yl)-2,5-dihydro-2-furanyl]oxy]-methyl]phosphonic acid, dimethyl ester A solution of the product of Step F (70 g, 0.127 mole) in dry methanol (500 mL) was made and cooled to –10° C., then sodium methoxide (180 mL of 25 wt. % in methanol, 4.4M) was added dropwise over 45 min, keeping the temperature below 0° C. The yellow reaction solution was stirred 16 hr (overnight) then checked by TLC (methylene chloride:methanol (90:10), $R_f$ (product) 0.25) which showed the reaction was partially complete. The reaction solution was slowly warmed to 20°–25° C. and monitored by TLC. After 6–7 hr, the reaction appeared complete by TLC. A polar by-product ($R_f$ 0.1) was observed as the reaction proceeds. This product may be partially suppressed by running the reaction at 0° C. to 5° C. followed by warming the reaction to ambient temperature.

The reaction solution was cooled to 0°–5° C., and a freshly prepared solution of hydrogen chloride in methanol was added dropwise until the reaction solution was neutral to moist litmus paper. Over-acidification of the reaction mixture should be avoided. The reaction solution was then concentrated in vacuo to an oily brown semi-solid residue.

The crude product was suspended in methylene chloride:ethanol (90:10), and applied to a silica gel (3.5 Kg) column, and eluted with this solvent mixture under pressure (20 psi, flow rate approximately 100 mL/min). After collecting approximately 20 liters of eluent the desired product eluted from the column. Product-containing fractions were combined and concentrated to an off-white solid, which then was dried azeotropically from toluene. The solid isolated weighed 27.7 g for a yield of 64%.

H. (2S-cis)-[[[5-(6-Amino-9H-purin-9-yl)-2,5-dihydro-2-furanyl]oxy]methyl]phosphonic acid, disodium salt To a suspension of the product of Step G (27.7 g, 0.081 mole), in methylene chloride (170 mL), was added N-methyl-N-trimethylsilyltrifluoroacetamide (60 mL, 64.7 g, 0.325 mole, 4 equiv.) The suspension was stirred for 15 min at 25° C., showing no physical change. The reaction mixture was then cooled to −5° C., and trimethylsilylbromide (32 mL, 37.12 g, 0.242 mole, 3 equiv.) was added in a steady stream over 1–2 min. A slight 2° C. exotherm was noted. After the addition was complete, cooking was removed and the reaction mixture was allowed to warm to 25° C. In approximately 10 min, a clear, pale yellow solution was obtained. The reaction solution was stirred 2 hr at 25° C., then checked by NMR and TLC (Merck Reverse Phase $CN^-$ plates, acetonitrile: $H_2O$ (50:50), $R_f$ (product) >0.9), which showed the reaction to be complete.

The reaction solution was rapidly added to a stirred mixture of 30% aqueous ammonium hydroxide (250 mL) and ice (250 g). The aqueous pH was 11–11.5 after completing the addition. The mixture was then extracted with methylene chloride (6×500 mL) then aqueous 1N sodium hydroxide was added. The aqueous solution was then placed under high vacuum for 1 hr, after which the pH measured approximately 9. The aqueous solution was then frozen and lyophilized to give approximately 40 g of a pinkish-white solid.

The solid was redissolved in water and the pH was checked. The pH should be maintained above 7 by addition of 1N sodium hydroxide. The solution then was applied to a 3 liter column of HP-20 resin. The column was eluted with water at a flow rate of approximately 9–10 mL/min (gravity driven only), collecting 50 mL fractions, which were analyzed by UV visualization and for halide with aqueous silver nitrate. Fractions testing positive for UV activity and negative for halide were combined and lyophilized to give a total of approximately 27.5 g of white solid. NMR analysis showed that the isolated solid was the desired compound contaminated with N-methyl-N-trimethylsilyltrifluoroacetamide. The solid was dissolved in water (approximately 150 mL), filtered through a 0.2 micron filter, stirred, and then 95% ethanol (1.5 liters) was rapidly added. The product precipitated as a thick white solid which was filtered and washed with ethanol. The solid was again filtered, and dissolved in water and lyophilized to give 20.5 g of product, for a yield of 71%. Spectral data indicated that the product was the desired product, m.p. 283°–287° C. (dec.) Analysis by HPLC indicated a purity of >99%.

$^1$H-NMR (300 MHz, $D_2O$): δ8.0 (1H, s); 7.9 (1H, s); 6.7 (1H, s); 6.5 (1H, d); 6.4 (1H, d); 6.0 (1H, s); 3.6–3.4 (2H, m).

$^{13}$C-NMR ($D_2O$): 156.0; 153.5; 149.0; 141.1; 134.0; 129.7; 119.0; (110.0; 110.6 (d)); 86.8; (67.8; 65.6 (d)).

BIOLOGICAL ACTIVITIES

The following assays were performed in cell culture systems to determine the concentrations of compounds that are effective in preventing several kinds of viral infections. The results are presented in Table V.

The following are abbreviations used in the description of the assay protocols:

HSV-1 (herpes simplex virus type 1, strain Schooler), HSV-2 (herpes simplex virus type 2, strain 186), VZV (varicella zoster virus, strain ELLEN), HCMV (human cytomegalovirus, strain AD 169), HIV (human immunodeficiency virus, strain HTLV-IIIB).

Cell Culture Assays

HSV-1, HSV-2, HCMV, and VZV antiviral assays:

Virus was adsorbed to WI-38 cell culture monolayers in 6 well culture plates (Costar, Cambridge, Mass.) for 1 hr prior to addition of maintenance medium containing duplicate dilutions of the test compound. Inhibition of plaque development was evaluated on fixed and strained monolayers after 4 days incubation at 37° C. for HSV-1 and HSV-2 and after 6–7 days incubation at 37° C. for HCMV and VZV. $IC_{50}$ values were determined from the drug concentration which conferred at least 50% plaque reduction compared to virus controls.

HIV antiviral assay (A) Suspensions of CEM (Nara and Fishchinger, *Nature*, 332:469, 1988) cells were infected at a multiplicity of infection (e.g. virus/cell) of 0.12 with HIV (strain HTLV-IIIB). After adsorption for 1–2 hr at 37° C., infected cells were diluted in growth medium (RPMI 1640 containing the antibiotics penicillin plus streptomycin and 10% fetal calf serum) to a final cell concentration of $1 \times 10^4$ viable cells/culture well in the presence of serial dilutions of the test compound, starting at 100 µg/mL. Triplicate samples at each drug concentration were used. Cultures of uninfected CEM cells were similarly prepared and incubated with serial dilutions of test compound in duplicate. All assays were performed in 96 well disposable cell culture plates. Untreated (infected and uninfected) cells were included as controls. All cultures were incubated for 7 days at 37° C. in a humidified atmosphere containing 5% $CO_2$. Following incubation, viable cell numbers were counted in each well using a colorimetric assay following incubation of cells with XTT-PMS solution (XTT tetrazolium reagent plus phenazine methosulfate PMS).

Percent reduction of viral cytopathic effect (CPE) in drug treated compared to untreated virus infected cells, and percent reductions of cell viability in drug treated uninfected cells compared to untreated controls were calculated and plotted versus the drug concentrations tested. From these plots, the $IC_{50}$ (the minimum drug concentration that inhibits CPE by 50%) and $TC_{50}$ (the minimum drug concentration that reduces cell viability by 50% in drug treated, uninfected cells) for each drug was calculated.

(B) Suspensions of MT-2 cells (S. Harada, et al., *Science*, 229, 563 (1985)) were infected at a multiplicity of infection of 0.03 $TLID_{50}$/cell with HIV (strain HTLV-III B). After adsorption for 1–2 hr at 37° C., infected cells were diluted in growth medium (RPMI 1640 containing the antibiotics penicillin plus streptomycin and 10% fetal calf serum) to give a final cell concentration of $1 \times 10^4$ viable cells/culture well in the presence of serial dilutions of the test compound, starting at 100 µg/mL. Triplicate samples at each drug concentration were used. Cultures of uninfected MT-2 cells were similarly prepared and incubated with serial dilutions of test compound in duplicate. All assays were performed in 96 well disposable cell culture plates. Untreated (infected and uninfected) cells were included as controls. All cultures were incubated for 7 days at 37° C. in a humidified atmosphere containing 5% $CO_2$. Following incubation, viable cell numbers were counted in each well using a colorimetric assay following incubation of cells with XTT-PMS solution (XTT tetrazolium reagent plus phenazine methosulfate PMS).

Percent reduction of viral cytopathic effect (CPE) in drug treated uninfected cells compared to untreated controls were calculated and plotted versus the drug concentrations tested. From these plots, the $IC_{50}$ (the minimum drug concentration that inhibits CPE by 50%) and $TC_{50}$ (the minimum drug concentration that reduces cell viability by 50% in drug treated uninfected cells) for each drug was calculated. 2',3'-

Dideoxycytidine and 3'-azido-3'-deoxythymidine were used as a positive drug control.

TABLE V

IN VITRO ANTIVIRAL ACTIVITY
$IC_{50}/TC_{50}(\mu g/mL)$

| Cmpd. of Example | HIV-1 | |
|---|---|---|
| | MT-2 cells | CEM cells |
| 73 | >100/>100 | >100/>100 |
| 74 | >100/>100 | >100/>100 |
| 77 | >100/76 | >100/96 |
| 75 | >100/>100 | >100[1]/>100 |
| 62 | >100/>100 | 39 −>100/>100 |
| 59 | 13–27/>100 | 10–24/>100 |
| 25 | 85/>100 | 29/>100 |
| 66 | 68/>100 | 18/>100 |
| ddc | 0.13–0.79/>10 | <0.03/2.5–5.1 |
| AZT | <0.03–0.15/>10 | >0.03/6.4 −>10 |

[1]39% reduction in viral cytopathic effect at 100 µg/mL.

What is claimed is:

1. A compound of formula (V)

wherein B is cytosine, 5-ethylcytosine, 5-methylcytosine, thymine, uracil, 5-chlorouracil, 5-bromouracil, 5-ethyluracil, 5-iodouracil, 5-propyluracil, 5-vinyluracil, hypoxanthine, xanthine, guanine, 8-bromoguanine, 8-chloroguanine, 8-methylguanine, 8-thioguanine, 3-deazaguanine, purine, 2-aminopurine, 2,6-diaminopurine, adenine, 3-deazaadenine, 8-aminoguanine, 8-hydrazinoguanine, 8-hydroxyguanine, or 2-acetamido-6-diphenylcarbamoylpurine;

and the pharmaceutically acceptable salts thereof.

2. The compound of claim 1 wherein B is hypoxanthine, xanthine, guanine, 8-bromoguanine, 8-chloroguanine, 8-methylguanine, 8-thioguanine, 3-deazaguanine, purine, 2-aminopurine, 2,6-diaminopurine, adenine, 3-deazaadenine, 8-aminoguanine, 8-hydrazinoguanine or 8-hydroxyguanine.

3. The compound of claim 2 wherein B is substituted at its 9-position.

4. The compound of claim 1 wherein B is cytosine, 5-ethylcytosine, 5-methylcytosine, thymine, uracil, 5-chlorouracil, 5-bromouracil, 5-ethyluracil, 5-iodouracil, 5-propyluracil or 5-vinyluracil.

5. The compound of claim 4 wherein B is substituted at its 1-position.

* * * * *